US010443052B2

(12) United States Patent
Freier

(10) Patent No.: US 10,443,052 B2
(45) Date of Patent: Oct. 15, 2019

(54) COMPOSITIONS FOR MODULATING C9ORF72 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 14/436,024

(22) PCT Filed: Oct. 15, 2013

(86) PCT No.: PCT/US2013/065073
§ 371 (c)(1),
(2) Date: Apr. 15, 2015

(87) PCT Pub. No.: WO2014/062691
PCT Pub. Date: Apr. 24, 2014

(65) Prior Publication Data
US 2015/0259679 A1     Sep. 17, 2015

Related U.S. Application Data

(60) Provisional application No. 61/714,132, filed on Oct. 15, 2012.

(51) Int. Cl.
*C12N 15/113*     (2010.01)
*C07H 21/02*      (2006.01)
*C07H 21/04*      (2006.01)
*C12N 5/00*       (2006.01)

(52) U.S. Cl.
CPC ........ *C12N 15/113* (2013.01); *C12N 2310/11* (2013.01); *C12N 2310/313* (2013.01); *C12N 2310/315* (2013.01); *C12N 2310/322* (2013.01); *C12N 2310/3233* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,801,154 A | 9/1998 | Baracchini et al. | |
| 5,998,148 A | 12/1999 | Bennett et al. | |
| 6,268,490 B1 | 7/2001 | Imanishi et al. | |
| 6,525,191 B1 | 2/2003 | Ramasamy | |
| 6,582,908 B2 | 6/2003 | Fodor et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,696,345 B2 | 4/2010 | Allerson et al. | |
| 7,759,478 B1 | 7/2010 | Bentwich et al. | |
| 8,501,805 B2 | 8/2013 | Seth et al. | |
| 8,530,640 B2 | 9/2013 | Seth et al. | |
| 8,546,556 B2 | 10/2013 | Seth et al. | |
| 9,012,421 B2 | 4/2015 | Migawa et al. | |
| 9,605,263 B2 | 3/2017 | Rigo | |
| 9,896,729 B2 | 2/2018 | Pickering-Brown et al. | |
| 9,963,699 B2 | 5/2018 | Bennett et al. | |
| 10,138,482 B2 | 11/2018 | Rigo | |
| 10,221,414 B2 | 3/2019 | Freier et al. | |
| 2001/0053519 A1 | 12/2001 | Fodor et al. | |
| 2003/0228597 A1 | 12/2003 | Cowsert et al. | |
| 2004/0038274 A1 | 2/2004 | Cook et al. | |
| 2004/0171570 A1 | 9/2004 | Allerson et al. | |
| 2004/0181048 A1 | 9/2004 | Wang | |
| 2005/0130923 A1 | 6/2005 | Bhat et al. | |
| 2006/0003322 A1 | 1/2006 | Bentwich et al. | |
| 2007/0031844 A1 | 2/2007 | Khvorova et al. | |
| 2008/0039618 A1 | 2/2008 | Allerson et al. | |
| 2009/0012281 A1 | 1/2009 | Swayze et al. | |

(Continued)

FOREIGN PATENT DOCUMENTS

EP    1752536    2/2007
WO    1996014329    5/1996
(Continued)

OTHER PUBLICATIONS

Bennett et al. Biochimica et Biophysica Acta vol. 1489:19-30, 1999.*
"The ALS Association and the Packard Center Partner to Develop Animal Model Systems for Most Common Cause of Familial ALS", http://www.alsa.org/news/archive/new-animal-model-systems.html (printed Oct. 23, 2015).
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals" Chimia. (1996) 50(4):168-176.

(Continued)

*Primary Examiner* — Sean McGarry
(74) *Attorney, Agent, or Firm* — McNeill Baur PLLC

(57) ABSTRACT

Disclosed herein are compositions and methods for reducing expression of C9ORF72 mRNA and protein in an animal with C9ORF72 specific inhibitors. Such methods are useful to treat, prevent, or ameliorate neurodegenerative diseases in an individual in need thereof. Such C9ORF72 specific inhibitors include antisense compounds. Examples of neurodegenerative diseases that can be treated, prevented, and ameliorated with the administration C9ORF72 specific inhibitors include amyotrophic lateral sclerosis (ALS), frontotemporal dementia (FTD), corticalbasal degeneration syndrome (CBD), atypical Parkinsonian syndrome, and olivopontocerellar degeneration (OPCD).

82 Claims, No Drawings
Specification includes a Sequence Listing.

(56) References Cited

U.S. PATENT DOCUMENTS

| | | | |
|---|---|---|---|
| 2010/0216864 A1 | 8/2010 | Staarup et al. | |
| 2012/0149757 A1 | 6/2012 | Krainer et al. | |
| 2012/0214865 A1 | 8/2012 | Bennett et al. | |
| 2013/0035366 A1 | 2/2013 | Swayze et al. | |
| 2014/0255936 A1* | 9/2014 | Rademakers | C12Q 1/6883 435/6.11 |
| 2014/0303238 A1* | 10/2014 | Linsley | C07H 21/04 514/44 A |
| 2015/0148404 A1* | 5/2015 | de Visser | C12N 15/113 514/44 A |
| 2015/0251655 A1 | 9/2015 | Lakehal-Ayat et al. | |
| 2015/0267197 A1 | 9/2015 | Bennett et al. | |
| 2016/0024496 A1 | 1/2016 | Bennett et al. | |
| 2016/0108396 A1 | 4/2016 | Jensen et al. | |
| 2016/0251655 A1 | 9/2016 | Freier et al. | |
| 2016/0304871 A1 | 10/2016 | Rigo | |
| 2017/0349897 A1 | 12/2017 | Rigo | |
| 2018/0318330 A1 | 11/2018 | Prakash et al. | |

FOREIGN PATENT DOCUMENTS

| | | |
|---|---|---|
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/113016 | 12/2005 |
| WO | WO 2005/121368 | 12/2005 |
| WO | WO 2007/056113 | 5/2007 |
| WO | 2007089584 | 8/2007 |
| WO | 2007131237 | 11/2007 |
| WO | WO 2007/134181 | 11/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | 2009007855 | 1/2009 |
| WO | WO 2009/006478 | 1/2009 |
| WO | WO 2009/049166 | 4/2009 |
| WO | WO 2009/060124 | 5/2009 |
| WO | WO 2011/005793 | 1/2011 |
| WO | WO 2011/135396 | 11/2011 |
| WO | 2012005898 | 1/2012 |
| WO | 2012012443 | 1/2012 |
| WO | WO 2012/012467 | 1/2012 |
| WO | 2012087983 | 6/2012 |
| WO | WO 2012/092367 | 7/2012 |
| WO | WO 2012/135736 | 10/2012 |
| WO | 2013036833 | 3/2013 |
| WO | WO 2013/030588 | 3/2013 |
| WO | WO 2013/075079 | 5/2013 |
| WO | WO 2013/082548 | 6/2013 |
| WO | WO 2013/086207 | 6/2013 |
| WO | WO 2013/173608 | 11/2013 |
| WO | WO 2014/062686 | 4/2014 |
| WO | WO 2014/062691 | 4/2014 |
| WO | WO 2014/062736 | 4/2014 |
| WO | WO 2014/114660 | 7/2014 |
| WO | WO 2015/054676 | 4/2015 |
| WO | WO 2016/024205 | 2/2016 |
| WO | WO 2016/050822 | 4/2016 |
| WO | WO 2016/060919 | 4/2016 |
| WO | WO 2016/168592 | 10/2016 |
| WO | WO 2017/079291 | 5/2017 |
| WO | WO 2017/180835 | 10/2017 |
| WO | WO 2018/064600 | 4/2018 |
| WO | WO-2019092618 A2 * | 5/2019 |

OTHER PUBLICATIONS

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chio et al., "Prevalence of SOD1 mutations in the Italian ALS population" Neurology (2008) 70:533-537.

Crooke et al., "Basic Principles of Antisense Therapeutics" Antisense Research and Application (1998) Chapter 1:1-50.

Dejesus-Hernandez et al., "Expanded GGGGCC hexanucleotide repeat in noncoding region of C9ORF72 causes chromosome 9p-linked FTD and ALS" Neuron (2011) 72:245-256.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a novel bcl-2/bcl-xLbispecific antisense oligonucleotide against tumors of diverse histologic origins" J. Natl. Cancer Inst. (2001) 93:463-471.

Hirtz et al., "How common are the "common" neurologic disorders?" Neurology (2007) 68:326-337.

International Search Report for application No. PCT/US2013/065073 dated Apr. 22, 2014.

Johnson et al., "Exome sequencing reveals VCP mutations as a cause of familial ALS" Neuron (2010) 68:857-864.

Jones et al., "RNA quantitation by fluorescence-based solution assay: RiboGreen reagent characterization" Analytical Biochemistry (1998) 265(2):368-374.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Kwiatkowski et al., "Mutations in the FUS/TLS gene on chromosome 16 cause familial amyotrophic lateral sclerosis" Science (2009) 323:1205-1208.

Laaksovirta et al, "Chromosome 9p21 in amyotrophic lateral sclerosis in Finland: a genome-wide association study" Lancet Neurol. (2010) 9:978-985.

Lagier-Tourenne et al., "Targeted Degradation of Sense and Antisense C9ORF72 RNA Foci as Therapy for ALS and Frontotemporal Degeneration" PNAS (2013) 1-10.

Leumann et al., "DNA Analogues: From Supramolecular Principles to Biological Properties" Bioorganic & Medicinal Chemistry (2002) 10:841-854.

Lillo et al., "Frontotemporal dementia and motor neurone disease: overlapping clinic-pathological disorders" J. Clin. Neurosci. (2009) 16:1131-1135.

Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.

(56) References Cited

OTHER PUBLICATIONS

Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Hely. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Neumann et al., "Ubiquitinated TDP-43 in frontotemporal lobar degeneration and amyotrophic lateral sclerosis" Science (2006) 314:130-133.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Pearson et al., "Familial frontotemporal dementia with amyotrophic lateral sclerosis and a shared haplotype on chromosome 9p" J. Nerol. (2011) 258:647-655.
Renton et al., "A Hexanucleotide Repeat Expansion in C9ORF72 Is the Cause of Chromosome 9p21-Linked ASL-FTD" Neuron (2011) 72:257-268.
Reynolds et al., "Rational siRNA design for RNA interference" Nature Biotechnology (2004) 22(3):326-330.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sanghvi et al., "Heterocyclic Base Modifications in Nucleic Acids and Their Applications in Antisense Oligonucleotides" Antisense Research and Applications (1993) pp. 273-288.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of biosequences" Adv. Appl. Math. (1981) 2(4):482-489.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Natl. Acad. Sci. USA (2000) 97: 5633-5638.
Woolf et al., "Specificity of antisense oligonucleotides in vivo" PNAS (1992) 89: 7305-7309.
Zhang et al., "PowerBLAST: A New Network Blast Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for Application No. PCT/US2016/027747 dated Sep. 30, 2016, 12 pages.
"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).

Baughn et al, "Sense and Anti-Sense RNA Foci in c9ALS/FTD: More Light in a House of Mirrors" Annals of Neurology (Oct. 14, 2013) 74(17): pS60.
File History of U.S. Appl. No. 15/028,626, filed Apr. 11, 2016.
File History of U.S. Appl. No. 15/130,818, filed Apr. 15, 2016.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=1&satkey=24474174).
International Search Report for application on. PCT/US2014/060194 dated Apr. 14, 2015.
Madson, "Antisense Against C9ORF72", http://alsn.mda.org/article/antisense-against-c90rf72 Jul. 1, 2012 (printed Oct. 28, 2015).
Nelson et al., "The unstable repeats—three evolving faces of neurological disease." Neuron (2013) 77(5):825-43.
Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.
Baloh, R.H., "Targeting RNA foci shows a therapeutic effect in iPSC-derived motor neurons from C9orf72 repeat patients" ALSMND meeting, Milan, Dec. 6, 2013.
Baloh, R.H., "Induced Pluripotent stem cell models from C9orf72 patients." Oral presentation, California ALS PAC10 Research Summit, Los Angeles, CA, Nov. 11, 2012.
Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.
Baughn et al, "Sense and Anti-Sense RNA Foci in c9ALS/FTD: More Light in a House of Mirrors" Annals of Neurology (Dec. 2013) 74(17): pS60.
Bieniek et al., "Tau pathology in frontotemporal lobar degeneration with C9ORF72 hexanucleotide repeat expansion" Acta Neuropathol (2013) 125(2):289-302.
Brettschneider et al., "Microglial activation correlates with disease progression and upper motor neuron clinical symptoms in Amyotrophic Lateral Sclerosis", Plos ONE (2012) 7:e39216.
Donnelly et al., "Limited availability of ZBP1 restricts axonal mRNA localization and nerve regeneration capacity" EMBO J. (2011) 30:4665-4677.
Donnelly et al., "RNA toxicity from the ALS/FTD C9ORF72 expansion is mitigated by antisense intervention" Neuron (2013) 80(2):415-428.
Donnelly et al., "Development of C9orf72 ALS Biomarkers and Therapeutics" Annals of Neuology (Oct. 10, 2012) 72(16):S67-S68.
Donnelly et al., "Development of a C9ORF72 ALS antisense therapyy and a therapeutic biomarker" Abstracts of the Society for Neuroscience, Washington, DC, US, Oct. 16, 2012, Retrieved from the Internet Aug. 15, 2016: http://www.abstractsonline.com/Plan/ViewAbstract.aspx?sKey=c4cccfd5-5e4c-4d1e-9569-9a1b1eb21d80&cKey=c5c69155-5d2b-467c-8d1f-87299c514c7f&mKey=%7b70007181-01C9-4DE9-A0A2-EEBFA14CD9F1%7d.
Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.
Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.
European Search Report for application No. 13847957.1 dated Jul. 13, 2016.
European Search Report for application No. 13846313.8 dated May 11, 2016.
European Search Report for application No. 13847099.2 dated May 25, 2016.
Ganesalingam et al., "Combination of neurofilament heavy chain and complement C3 as CSF biomarkers for ALS" Journal of Neurochemistry (2011) 117: 528-537.

(56) References Cited

OTHER PUBLICATIONS

Ince et al., "Molecular pathology and genetic advances in amyotrophic lateral sclerosis: an emerging molecular pathway and the significance of glial pathology," Acta Neuro. (2011) 122:657-671.
International Search Report for application PCT/US13/65067 dated Jan. 24, 2014.
International Search Report for application PCT/US2013/065131 dated Feb. 14, 2014.
Jiang et al., "Antisense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.
Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.
Jeong et al., "Rapid Identification of Monospecific Monoclonal Antibodies Using a Human Proteome Microarray." Mol. Cell. Proteomics (2012) 11(6): O111.016253-1 to O111.016253-10.
Klein et al., "Gain of RNA function in pathological cases: Focus on myotonic dystrophy" Biochimie (2011) 93(11):2006-2012.
Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.
Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.
Lagier-Tourenne, C. "Therapy Development for ALS/MND and Frontotemporal Dementia with C9orf72 Expansion: Antisense Oligonucletide Mediated Reduction in Nuclear RNA Foci." ALS FD (Nov. 4, 2013) 14(sup2): p. 17.
Lindquist et al, "Corticobasal and ataxia syndromes widen the spectrum of C9ORF72 hexanucleotide expansion disease." Clin Genet (2013) 83:279-283.
Madson, "Antisense Against C9ORF72", http://alsn.mda.org/article/antisense-against-c9Orf72 (printed Oct. 28, 2015).
Mulders et al., "Triplet-repeat oligonucleotide-mediated reversal of RNA toxicity in myotonic dystrophy" PNAS (2009) 106(33):13915-13920.
O'Rourke et al., "C9orf72 BAC Transgenic Mice Display Typical Pathologic Features of ALS/FTD." Neuron (2015) 88(5):892-901.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Rabin et al., "Sporadic ALS has compartment-specific aberrant exon splicing and altered cell-matrix adhesion biology" Hum Mol Genet. (2010) 19(2):313-328.
Ravits, J., "Expanding Neurodegenerations: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Riboldi et al., "Antisense Oligonucleotide Therapy for the Treatment of C90RF72 ALS/FTD Diseses." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 11-14, 2015.
Sareen, et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Simon-Sanchez et al., "The clinical and pathological phenoype of C9OFR72 hexanucleotide repeat expansions", Brain: Journal of Neurology (2012) 135:723-735.
Todd et al. "RNA mediated neurodegeneration in repeat expansion disorders," Annals of Neruology (2009) 67(3):291-300.
Wojciechowska et al., "Cellular toxicity of expanded RNA repeats: focus on RNA foci" Human Molecular Genetics (2011) 1-11.
Zhang et al., "The C9orf72 repeat expansion disrupts nucleocytoplasmic transport." Nature (2015) 525(7567):56-61.
File History of U.S. Appl. No. 14/436,030, filed Apr. 15, 2016.
File History of U.S. Appl. No. 14/436,039, filed Apr. 15, 2015.
Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.
Donnelly et al., "Development of C9ORF72 ALS Biomarkers and Therapeutics American Neurological Association 2012 Annual Meeting, Poster Presentation, Boston, MA Oct. 10, 2012.".
Ash et al., "Unconventional Translation of C9ORF72 GGGGCC Expansion Generates Insoluble Ploypeptides Specific to c9FTD/ALS" Neuron (2013) 77(4): 639-646.
Extended European Search Report for application No. 14852924.1 dated Jun. 20, 2017, 13 pages.
Fernandes et al., "Oligonucleotide-Based Therapy for FTD/ALS Caused by the C9orf72 Repeat Expansion: A Perspective" Journal of Nucleic Acids (2013) :1-11.
Gendron et al., "Poly(GP) proteins area useful pharmacodynamic marker for C9ORF72-associated amyotrophic lateral sclerosis" Sci Tran Med (2017) 9(383):1-12.
GenBank: Accession No. NT_008413, dated Jul. 24, 2012, 5 pages.
International Search Report for application in PCT/US2017/027355 dated Jul. 26, 2017, 11 pages.
International Search Report for application in PCT/US2016/060106 dated Feb. 1, 2017, 10 pages.
Lee et al., "Antisense Therapy in Neurology" Journal of Personalized Medicine (2013) 3(3): 144-176.
Mahoney et al., "Frontotemporal Dementia with the C9ORF72 Hexanucleotide Repeat Expansion: Clinical, Neuroanatomical and Neuropathological Features," Brain, 2012, 135:736-750.
Sha et al., "Treatment implications of C9ORF72" Alzheimers Res Ther (2012) 4(6): 46.
Thomsen, "Dramatically improved RNA in 1-15 situ hybridization signals using LNA-modified probes" RNA (2005) 11(11): 1745-1748.
Watts et al., "Gene silencing by siRNAs and antisense oligonucleotides in the laboratory and the clinic," J Pathol., 226(2): pp. 365-379 (Jan. 2012).
Kurreck, "Antisense technologies. Improvement through novel chemical modifications," Eur J Biochem, 2003, 270:1628-1644.

* cited by examiner

COMPOSITIONS FOR MODULATING C9ORF72 EXPRESSION

SEQUENCE LISTING

The present application is being filed along with a Sequence Listing in electronic format. The Sequence Listing is provided as a file entitled BIOL0211USASEQ_ST25.txt created Apr. 15, 2015, which is 196 Kb in size. The information in the electronic format of the sequence listing is incorporated herein by reference in its entirety.

FIELD

Provided are compositions and methods for reducing expression of C9ORF72 mRNA and protein in an animal. Such methods are useful to treat, prevent, or ameliorate neurodegenerative diseases, including amyotrophic lateral sclerosis (ALS), frontotemporal dementia (FTD), cortical-basal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hintz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The chromosome 9p21ALS-FTD locus in the last major autosomal-dominant gene whose mutation is causative of ALS. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Provided herein are compositions and methods for modulating levels of C9ORF72 mRNA and protein in cells, tissues, and animals. In certain embodiments, C9ORF72 specific inhibitors modulate expression of C9ORF72 mRNA and protein. In certain embodiments, C9ORF72 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 mRNA levels are reduced. In certain embodiments, C9ORF72 protein levels are reduced. In certain embodiments, certain C9ORF72 mRNA variants are preferentially reduced. In certain embodiments, the C9ORF72 mRNA variants preferentially reduced are variants containing intron 1. In certain embodiments, intron 1 contains a hexanucleotide repeat expansion. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats. In certain embodiments, the hexanucleotide repeat expansion is associated with nuclear foci. In certain embodiments, the compositions and methods described herein are useful for reducing C9ORF72 mRNA levels, C9ORF72 protein levels, and nuclear foci. Such reduction can occur in a time-dependent manner or in a dose-dependent manner.

Also provided are methods useful for preventing, treating, and ameliorating diseases, disorders, and conditions associated with C9ORF72. In certain embodiments, such diseases, disorders, and conditions associated with C9ORF72 are neurodegenerative diseases. In certain embodiments, the neurodegenerative disease is amyotrophic lateral sclerosis (ALS), frontotemporal dementia (FTD), corticalbasal degeneration syndrome (CBD), atypical Parkinsonian syndrome, and olivopontocerellar degeneration (OPCD).

Such diseases, disorders, and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 specific inhibitor to an individual in need thereof. In certain embodiments, the C9ORF72 specific inhibitor is a nucleic acid. In certain embodiments, the nucleic acid is an antisense compound. In certain embodiments, the antisense compound is a single-stranded antisense oligonucleotide. In certain embodiments, the single-stranded antisense oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl group" (also 2'-MOE and 2'-OCH$_2$CH$_2$—OCH$_3$ and MOE) refers to an O-methoxyethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-O-methoxyethyl group.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of C9ORF72", it is implied that the C9ORF72 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds. Antisense mechanisms include, without limitation, RNase H mediated antisense; RNAi mechanisms, which utilize the RISC pathway and include, without limitation, siRNA, ssRNA and microRNA mechanisms; and occupancy based mechanisms, including, without limitiation uniform modified oligonucleotides. Certain antisense compounds may act through more than one such mechanism and/or through additional mechanisms.

"Antisense inhibition" means reduction of target nucleic acid levels or target protein levels in the presence of an antisense compound complementary to a target nucleic acid compared to target nucleic acid levels or target protein levels in the absence of the antisense compound Inhibition may be any means including RNase H degradation, such as with a gapmer, and steric blockage, such as with a uniformly modified oligonucleotide.

"Antisense oligonucleotide" means a single-stranded oligonucleotide having a nucleobase sequence that permits hybridization to a corresponding segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 associated disease" means any disease associated with any C9ORF72 nucleic acid or expression product thereof. Such diseases may include a neurodegenerative disease. Such neurodegenerative diseases may include ALS and FTD.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise GGGGCC, GGGGGG, GGGGGC, or GGGGCG repeated at least 30 times. Such diseases may include a neurodegenerative disease. Such neurodegenerative diseases may include ALS and FTD.

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 (including genomic DNA comprising introns and exons), and an mRNA sequence encoding C9ORF72. "C9ORF72 mRNA" means an mRNA encoding a C9ORF72 protein.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of pharmaceutical agent sufficient to effectuate a desired physiological outcome in an individual in need of the pharmaceutical agent. The effective amount may vary among individuals depending on the health and physical condition of the individual to be treated, the taxonomic group of the individuals to be treated, the formulation of the composition, assessment of the individual's medical condition, and other relevant factors.

"Expression" means conversion of the information from a C9ORF72 gene into mRNA via transcription and then to protein via translation. Expression may result in a phenotypic manifestation of the C9ORF72 gene.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include an antisense compound and a target nucleic acid.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing expression of C9ORF72 mRNA and/or protein levels in the presence of a C9ORF72 specific inhibitor, including a C9ORF72 antisense oligonucleotide, as compared to expression of C9ORF72 mRNA and/or protein levels in the absence of a C9ORF72 specific inhibitor, such as a C9ORF72 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical agent" means the substance or substances in a pharmaceutical composition that provide a therapeutic benefit when administered to an individual. For example, in certain embodiments an antisense oligonucleotide targeted to C9ORF72 is a pharmaceutical agent.

"Pharmaceutical composition" means a mixture of substances suitable for administering to an individual. For example, a pharmaceutical composition may comprise one or more pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid.

In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods for decreasing C9ORF72 mRNA and protein expression.

Certain embodiments provide methods for the treatment, prevention, or amelioration of diseases, disorders, and conditions associated with C9ORF72 in an individual in need thereof. Also contemplated are methods for the preparation of a medicament for the treatment, prevention, or amelioration of a disease, disorder, or condition associated with C9ORF72. C9ORF72 associated diseases, disorders, and conditions include neurodegenerative diseases. In certain embodiments, the neurodegenerative disease may be ALS or FTD. In certain embodiments, the neurodegenerative disease may be familial or sporadic.

Certain embodiments provide for the use of a C9ORF72 specific inhibitor for treating, preventing, or ameliorating a C9ORF72 associated disease. Certain embodiments provide for the use of a C9ORF72 specific inhibitor for treating, preventing, or ameliorating a C9ORF72 hexanucleotide repeat expansion associated disease. In certain embodiments, the hexanucleotide repeat expansion may comprise GGGGCC, GGGGGG, GGGGGC, or GGGGCG. In certain embodiments, C9ORF72 specific inhibitors are nucleic acids (including antisense compounds), peptides, antibodies, small molecules, and other agents capable of inhibiting the expression of C9ORF72 mRNA and/or C9ORF72 protein.

Described herein are compounds comprising a single-stranded antisense oligonucleotide complementary to a C9ORF72 nucleic acid or a C9ORF72 homolog nucleic acid.

In certain embodiments, the C9ORF72 nucleic acid is a human C9ORF72 nucleic acid.

In certain embodiments, the C9ORF72 nucleic acid contains a hexanucleotide repeat expansion.

In certain embodiments, the C9ORF72 nucleic acid does not contain a hexanucleotide repeat expansion.

In certain embodiments, the single-stranded antisense oligonucleotide is specifically hybridizable to a human C9ORF72 nucleic acid.

In certain embodiments, the single-stranded antisense oligonucleotide is at least 75%, at least 80%, at least 85%, at least 90%, at least 95%, or 100% complementary to an equal length portion of a human C9ORF72 nucleic acid.

In certain embodiments, the single-stranded antisense oligonucleotide is complementary to any of exon, an intron, the 5' UTR, the 3' UTR, a repeat region, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a human C9ORF72 nucleic acid.

Described herein are compounds comprising a single-stranded antisense oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 contiguous nucleobases of SEQ ID NO: 30-369.

In certain embodiments, the single-stranded antisense oligonucleotide comprises at least one modification.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the single-stranded antisense oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-$(CH_2)_n$—O-2' bridge, wherein n is 1 or 2; and 4'-$CH_2$—O—$CH_2$-2'.

In certain embodiments, the bicyclic sugar comprises a 4'-$CH(CH_3)$—O-2' bridge.

In certain embodiments, the at least one modified nucleoside having a modified sugar comprises a non-bicyclic 2'—modified modified sugar moiety.

In certain embodiments, the 2'—modified sugar moiety comprises a 2'-O-methoxyethyl group.

In certain embodiments, the 2'—modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:

a gap segment consisting of linked deoxynucleosides;

a 5' wing segment consisting of linked nucleosides;
a 3' wing segment consisting of linked nucleosides;
wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15 linked nucleosides.

In certain embodiments, the single-stranded antisense oligonucleotide consists of 16 linked nucleosides.

In certain embodiments, the single-stranded antisense oligonucleotide consists of 17 linked nucleosides.

In certain embodiments, the single-stranded antisense oligonucleotide consists of 18 linked nucleosides.

In certain embodiments, the single-stranded antisense oligonucleotide consists of 19 linked nucleosides.

In certain embodiments, the single-stranded antisense oligonucleotide consists of 20 linked nucleosides.

In certain embodiments, the single-stranded antisense oligonucleotide consists of 21 linked nucleosides.

In certain embodiments, the single-stranded antisense oligonucleotide consists of 22 linked nucleosides.

In certain embodiments, the single-stranded antisense oligonucleotide consists of 23 linked nucleosides.

In certain embodiments, the single-stranded antisense oligonucleotide consists of 24 linked nucleosides.

In certain embodiments, the single-stranded antisense oligonucleotide consists of 25 linked nucleosides.

Described herein are uses of the compound for the manufacture of a medicament for treating a neurodegenerative disease.

Provided herein are methods of preferentially inhibiting expression of mRNA transcripts containing a hexanucleotide repeat expansion by contacting a cell with an antisense oligonucleotide targeting upstream of exon 1B.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-10-4 gapmer motif.

In certain embodiments, antisense compounds targeted to a C9ORF72 nucleic acid possess a 4-10-4 gapmer motif.

In certain embodiments, antisense compounds targeted to a C9ORF72 nucleic acid possess a 4-10-3 gapmer motif.

In certain embodiments, antisense compounds targeted to a C9ORF72 nucleic acid possess a 5-9-5 gapmer motif.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$—O-2' bridge, wherein n is 1 or 2; and 4'-CH$_2$—O—CH$_2$-2'. In certain embodiments, the bicyclic sugar is comprises a 4'-CH (CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a C9ORF72 nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleosides is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group. In certain embodiments, uniformly modified antisense compounds may target C9ORF72, or any portion thereof, such as a hexanucleotide repeat expansion. In certain embodiments, targeting the hexanucleotide repeat expansion with a unformily modified antisense compound reduces the repeat RNA by blocking the interaction with RNA binding proteins. In certain embodiments, this results in the toxic RNA being absent from foci and benig degraded instead.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain emodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 epxression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2; 4'-($CH_2$)$_2$—O-2' (ENA); 4'-$CH(CH_3)$—O-2' and 4'-CH($CH_2OCH_3$)—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

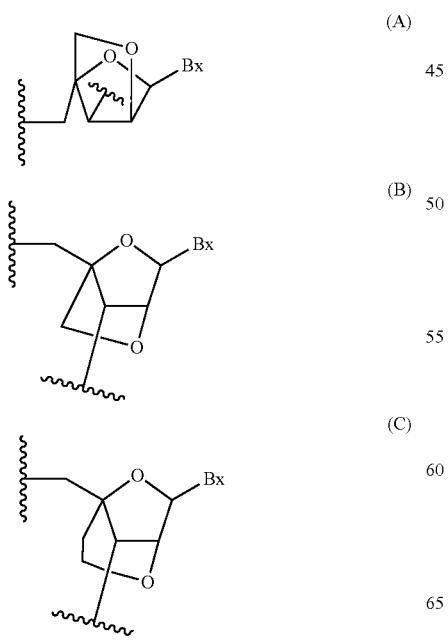

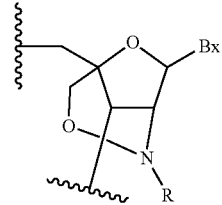

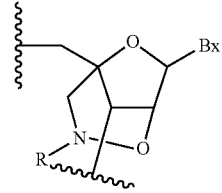

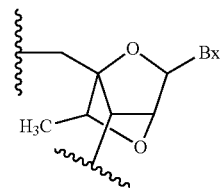

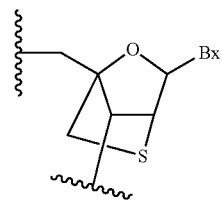

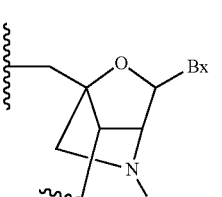

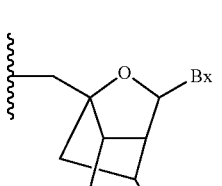

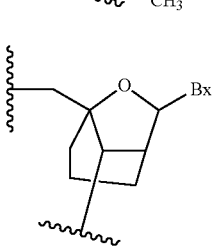

wherein Bx is the base moiety and R is independently H, a protecting group or $C_1$-$C_{12}$ alkyl.

In certain embodiments, bicyclic nucleosides are provided having Formula I:

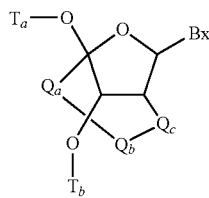

I wherein:
Bx is a heterocyclic base moiety;
$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;
$R_c$ is $C_1-C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

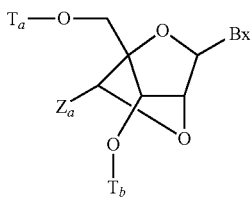

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1-C_6$ alkyl, or substituted $C_1-C_6$ alkyl and X is O or $NJ_c$.

In certain embodiments, bicyclic nucleosides are provided having Formula III:

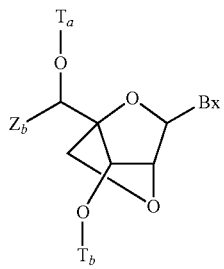

III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl or substituted acyl (C(=O)—).

In certain embodiments, bicyclic nucleosides are provided having Formula IV:

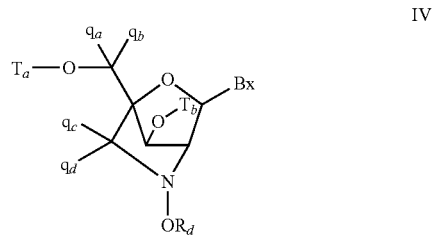

IV wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl;
each $q_a$, $q_b$, $q_c$ and $q_d$ is, independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl, $C_1-C_6$ alkoxyl, substituted $C_1-C_6$ alkoxyl, acyl, substituted acyl, $C_1-C_6$ aminoalkyl or substituted $C_1-C_6$ aminoalkyl;

In certain embodiments, bicyclic nucleosides are provided having Formula V:

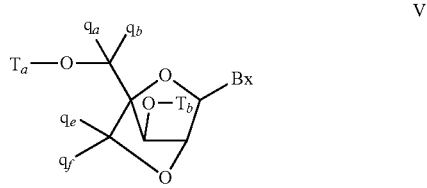

V wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl, $C_1-C_{12}$ alkoxy, substituted $C_1-C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;
or $q_e$ and $q_f$ together are $=C(q_g)(q_h)$;
$q_g$ and $q_h$ are each, independently, H, halogen, $C_1-C_{12}$ alkyl or substituted $C_1-C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

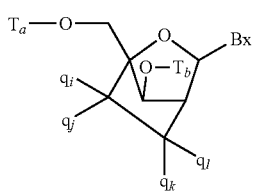

VI wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

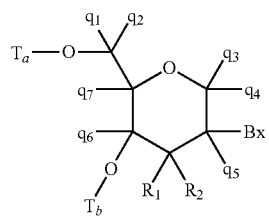

VII wherein independently for each of said at least one tetrahydropyran nucleoside analog of Formula VII:
Bx is a heterocyclic base moiety;
$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C$(=O)$—$N(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of certain variants of C9ORF72. In certain embodiments, the antisense oligonucleotides described herein preferentially inhibit expression of variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Based on earlier studies directed to repeat expansions, it is not possible to predict if antisense oligonucleotides targeting C9ORF72 outside of the hexanucleotide repeat expansion would successfully inhibit expression of C9ORF72 for two reasons. First, the C9ORF72 repeat expansion is located in an intron and it is not known if the RNA in the foci contains only the repeats or also the flanking intronic sequence. For example, an earlier study on myotonic dystrophy type 2 (DM2), which is a disease caused by a CCTG expansion mutation in intron 1 of the ZNF9 gene, determined that large DM2 expansions did not prevent allele-specific pre-mRNA splicing, nuclear export of the transcripts, or steady-state mRNA or protein levels. The study further demonstrated that the ribonuclear inclusions found associated with the disease are enriched for the CCUG expansion, but not the flanking intronic sequences. These data suggest that the downstream molecular effects of the DM2 mutation may be triggered by the accumulation of CCUG repeat tract alone. Therefore, this study implies that targeting the CCUG repeat expansion alone would lead to amelioration of the disease, since targeting the flanking sequences, especially the region downstream of the repeat expansion, would not affect the formation of ribonuclear inclusions (Margolis et al. Hum. Mol. Genet., 2006, 15:1808-1815). Second, it is not known how fast intron 1 of C9ORF72, which contains the repeats, is excised and accumulates in foci. Thus, it is not possible to predict if targeting the pre-mRNA would result in elimination of the repeat RNA and foci.

C9OFF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

EXAMPLES

Non-limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human C9ORF72 in HepG2 Cells

Antisense oligonucleotides were designed targeting a C9ORF72 nucleic acid and were tested for their effects on C9ORF72 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 7,000 nM antisense oligonucleotide. After a treatment period of approximately 24 hours, RNA was isolated from the cells and C9ORF72 mRNA levels were measured by quantitative real-time PCR. Human primer probe set RTS3750 (forward sequence TGTGACAGTTGGAATGCAGTGA, designated herein as SEQ ID NO: 15; reverse sequence GCCACTTAAAGCAATCTCTGTCTTG, designated as SEQ ID NO: 16; probe sequence TCGACTCTTTGCCCACCGCCA, designated herein as SEQ ID NO: 17) was used to measure mRNA levels. C9ORF72 mRNA levels were adjusted according to total RNA content, as measured by RIBOGREEN®. Results are presented as percent inhibition of C9ORF72, relative to untreated control cells.

The antisense oligonucleotides in Tables 6-10 were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages throughout each gapmer are phosphorothioate linkages. All cytosine residues throughout each gapmer are 5-methylcytosines. "Start site" indicates the 5'-most nucleoside to which the antisense oligonucleotide is targeted in the human gene sequence. "Stop site" indicates the 3'-most nucleoside to which the antisense oligonucleotide is targeted human gene sequence. Each antisense oligonucleotide listed in Tables 6-9 is targeted to the either human C9ORF72 mRNA sequence, designated herein as SEQ ID NO: 1 (GENBANK Accession No. NM_001256054.1) or the human C9ORF72 genomic sequence, designated herein as SEQ ID NO: 2 (the complement of GENBANK Accession No. NT_008413.18 truncated from nucleosides 27535000 to 27565000), or both. 'n/a' indicates that the antisense oligonucleotide did not target that particular gene sequence. The antisense oligonucleotides of Table 10 are targeted to either SEQ ID NO: 3 (GENBANK Accession No. BQ068108.1) or SEQ ID NO: 4 (GENBANK Accession No. NM_018325.3).

As shown in Tables 6-10, below, several of the oligonucleotides targeting SEQ ID NO: 1 exhibit at least 50% inhibition, including those targeted to nucleobases 90-647, 728-1541, 1598-1863, 1935-2146, 2232-2251, 2429-2576, 2632-2743, 2788-2807, 2860-2879, 2949-2968, 3062-3081, 3132-3151, and 3250-3269 of SEQ ID NO 1. These include SEQ ID NOs: 32, 33, 34, 35, 36, 37, 38, 40, 41, 42, 43, 44, 45, 46, 47, 50, 51, 53, 55, 56, 57, 61, 62, 64, 66, 67, 72, 73, 75, 76, 81, 82, 85, 89, 90, 91, 92, 93, 94, 96, 97, 100, 102, 103, 109, 111, 112, 115, 116, 117, 118, 119, 120, 121, 122, 123, 124, 125, 126, 130, 131, 132, 133, 137, 139, 140, 141, 145, 146, 149, 150, 151, 152, 153, 154, 165, 166, 168, 169, 170, 171, 174, 179, 181, 182, 183, 185, 186, 187, 188, 190, 192, 195, 197, 199, 320, 321, 322, 323, 324, 325, 326, 327, 328, 329, 330, 331, and 332. Several of the oligonucleotides exhibit at least 70% inhibition, including those targeted to nucleobases 90-359, 430-479, 550-569, 617-647, 940-959, 1013-1033, 1446-1465, 1687-1706, 1844-1863, 1935-2007, and 2679-2698 of SEQ ID NO 1. These include SEQ ID NOs: 32, 33, 34, 35, 36, 40, 41, 42, 43, 44, 47, 66, 67, 85, 96, 103, 117, 119, 154, 165, 168, 186, 320, 321, 324, 327, 328, and 331. Several of the oligonucleotides exhibit at least 80% inhibition, including those targeted to nucleobases 90-265 and 310-329. These include SEQ ID NOs: 32, 33, 35, 40, 42, and 321. Several of the oligonucleotides exhibit at least 90% inhibition, including those targeted to nucleobases 190-209 and 310-329 of SEQ ID NO 1. These include SEQ ID NOs: 40 and 321.

As shown in Tables 6-20, below, several of the oligonucleotides targeting SEQ ID NO: 2 exhibit at least 50% inhibition, including those targeted to nucleobases 1552-1572, 2187-2238, 2728-2779, 3452-2471, 3752-3771, 5025-5044, 5656-5675, 6200-6219, 7594-7613, 7840-8328, 9415-9434, 12526-12545, 13357-13524, 13642-13661, 13790-14130, 14243-14335, 14699-14777, 15587-15606, 16395-16488, 18233-18373, 24306-24340, 24472-24491, 24565-24676, 26400-26424, 26606-26982, 27054-27265, 27351-27370, 27548-27998, 28068-28087, 28181-28270, and 28369-28388 of SEQ ID NO 2. These include SEQ ID NOs: 32, 33, 34, 35, 36, 37, 38, 40, 41, 42, 43, 44, 45, 46, 47, 50, 51, 53, 55, 56, 57, 64, 67, 72, 73, 75, 76, 81, 82, 85, 89, 90, 91, 92, 93, 94, 96, 97, 100, 102, 103, 111, 112, 115, 117, 118, 119, 121, 122, 123, 124, 125, 126, 130, 131, 132, 133, 137, 139, 140, 141, 145, 146, 149, 150, 151, 152, 153, 154, 165, 166, 168, 169, 170, 171, 174, 179, 181, 182, 183, 185, 186, 187, 188, 190, 192, 195, 197, 199, 205, 206, 208, 211, 212, 224, 226, 230, 231, 250, 251, 252, 256, 300, 301, 304, 306, 307, 310, 320, 321, 322, 323, 324, 325, 326, 327, 328, 329, 330, 331, and 332. Several of the oligonucleotides exhibit at least 70% inhibition, including those targeted to nucleobases 3452-2471, 7840-8159, 8230-8249, 12526-12545, 13642-13661, 14075-14094, 14316-14335, 14758-14777, 16395-16414, 16469-16488, 24655-24674, 26963-26982, 27054-27126, and 27798-27817 of SEQ ID NO 2. These include SEQ ID NOs: 32, 33, 34, 35, 36, 40, 41, 42, 43, 44, 47, 67, 85, 96, 103, 117, 119, 154, 165, 168, 186, 251, 306, 320, 321, 324, 327, 328, and 331. Several of the oligonucleotides exhibit at least 80% inhibition, including those targeted to nucleobases 7848-8023 of SEQ ID NO 2. These include SEQ ID NOs: 32, 33, 35, 40, 42, and 321. Several of the oligonucleotides exhibit at least 90% inhibition, including those targeted to nucleobases 7870-7889 and 7990-8009 of SEQ ID NO 2. These include SEQ ID NOs: 40 and 321.

TABLE 6

| Target Start Site at SEQ ID NO: 1 | Target Start Site at SEQ ID NO: 2 | Sequence | ISIS No | % inhibition | SEQ ID NO |
|---|---|---|---|---|---|
| 3 | 1139 | AGCGGGACACCGTAGGTTAC | 576883 | 0 | 30 |
| 44 | 1180 | GTGGGCGGAACTTGTCGCTG | 576807 | 1 | 31 |
| 90 | 7848 | GTCACATTATCCAAATGCTC | 576808 | 85 | 32 |
| 125 | 7883 | GGTGGGCAAAGAGTCGACAT | 576809 | 82 | 33 |
| 155 | 7913 | ATCTCTGTCTTGGCAACAGC | 576810 | 78 | 34 |
| 160 | 7918 | AAGCAATCTCTGTCTTGGCA | 576811 | 81 | 35 |
| 165 | 7923 | ACTTAAAGCAATCTCTGTCT | 576812 | 78 | 36 |
| 170 | 7928 | TTGCCACTTAAAGCAATCTC | 576813 | 67 | 37 |
| 205 | 7963 | CCCAGTAAGCAAAAGTAGCT | 576814 | 66 | 38 |
| 227 | 7985 | ACTCTAGGACCAAGAATATT | 576815 | 11 | 39 |
| 232 | 7990 | GCCTTACTCTAGGACCAAGA | 576816 | 78 | 40 |
| 240 | 7998 | CCAAATGTGCCTTACTCTAG | 576817 | 73 | 41 |
| 246 | 8004 | TGGAGCCCAAATGTGCCTTA | 576818 | 81 | 42 |

TABLE 6-continued

| Target Start Site at SEQ ID NO: 1 | Target Start Site at SEQ ID NO: 2 | Sequence | ISIS No | % inhibition | SEQ ID NO |
|---|---|---|---|---|---|
| 254 | 8012 | TCTGTCTTTGGAGCCCAAAT | 576819 | 76 | 43 |
| 275 | 8033 | CCATCACTGAGAAGTACCTG | 576820 | 79 | 44 |
| 281 | 8039 | ATTTCTCCATCACTGAGAAG | 576821 | 61 | 45 |
| 288 | 8046 | AAAAGTTATTTCTCCATCAC | 576822 | 57 | 46 |
| 295 | 8053 | TGGCAAGAAAAGTTATTTCT | 576823 | 70 | 47 |
| 302 | 8060 | GTGTGGTTGGCAAGAAAAGT | 576824 | 44 | 48 |
| 313 | 8071 | CTCCATTTAGAGTGTGGTTG | 576825 | 39 | 49 |
| 330 | 8088 | TGCATTTCGAAGGATTTCTC | 576826 | 65 | 50 |
| 338 | 8096 | CCACTCTCTGCATTTCGAAG | 576827 | 67 | 51 |
| 362 | 8120 | ACAAAAAACTTTACATCTAT | 576828 | 22 | 52 |
| 376 | 8134 | CCTTTTCAGACAAGACAAAA | 576829 | 53 | 53 |
| 401 | 8159 | AAGATTAATGAAACAATAAT | 576830 | 0 | 54 |
| 411 | 8169 | GTTTCCATCAAAGATTAATG | 576831 | 62 | 55 |
| 446 | 8204 | ATTGATAGTCCATATGTGCT | 576832 | 59 | 56 |
| 452 | 8210 | AGTATAATTGATAGTCCATA | 571818 | 57 | 57 |
| 481 | 8239 | GGAGGTAGAAACTAAGTTCT | 576833 | 45 | 58 |
| 516 | 8274 | ATGTGTTAATCTATCAACAC | 576834 | 48 | 59 |
| 545 | 8303 | TGCATCCATATTCTTCCTTT | 576835 | 43 | 60 |
| 552 | n/a | TTCCTTATGCATCCATATTC | 576836 | 64 | 61 |
| 559 | n/a | CTTGTCTTTCCTTATGCATC | 576837 | 57 | 62 |
| 566 | n/a | ACATTTCTTGTCTTTCCTT | 576838 | 43 | 63 |
| 571 | 9415 | TCTGGACATTTTCTTGTCTT | 576839 | 61 | 64 |
| 578 | 9422 | ATAATCTTCTGGACATTTTC | 576840 | 37 | 65 |
| 617 | n/a | CTCTGACCCTGATCTTCCAT | 576841 | 79 | 66 |
| 628 | 12526 | TTGGAATAATACTCTGACCC | 576842 | 73 | 67 |
| 663 | 12561 | CAGTTCCATTACAGGAATCA | 576843 | 45 | 68 |
| 697 | 12595 | CTTCAGGAACACTGTGTGAT | 576844 | 20 | 69 |
| 705 | 12603 | ATCTATTTCTTCAGGAACAC | 576845 | 46 | 70 |
| 722 | n/a | AGTACTGTATCAGCTATATC | 576846 | 46 | 71 |
| 728 | 13357 | TCATTGAGTACTGTATCAGC | 576847 | 52 | 72 |
| 734 | 13363 | TCATCATCATTGAGTACTGT | 576848 | 67 | 73 |
| 740 | 13369 | CCAATATCATCATCATTGAG | 576849 | 47 | 74 |
| 755 | 13384 | TCATGACAGCTGTCACCAAT | 576850 | 51 | 75 |
| 761 | 13390 | AAGCCTTCATGACAGCTGTC | 576851 | 52 | 76 |
| 767 | 13396 | AGAAGAAAGCCTTCATGACA | 576852 | 23 | 77 |
| 773 | 13402 | TACTTGAGAAGAAAGCCTTC | 576853 | 24 | 78 |
| 778 | 13407 | ATTCTTACTTGAGAAGAAAG | 576854 | 12 | 79 |

TABLE 6-continued

| Target Start Site at SEQ ID NO: 1 | Target Start Site at SEQ ID NO: 2 | Sequence | ISIS No | % inhibition | SEQ ID NO |
|---|---|---|---|---|---|
| 782 | 13411 | AAAAATTCTTACTTGAGAAG | 576855 | 0 | 80 |
| 817 | 13446 | AGATGGTATCTGCTTCATCC | 576856 | 61 | 81 |
| 876 | 13505 | CAATCTAAGTAGACAGTCTG | 576857 | 57 | 82 |
| 911 | 13540 | TTAAGCAACAGTTCAAATAC | 576858 | 40 | 83 |
| 978 | 13607 | CTTTAAATAGCAAATGGAAT | 576859 | 26 | 84 |
| 1013 | 13642 | GCCATGATTTCTTGTCTGGG | 576860 | 79 | 85 |
| 1056 | 13685 | GCTTTAATGAGAAGTAAAAC | 576861 | 17 | 86 |
| 1091 | 13720 | TCTACAGTACAACTTAATAT | 576862 | 39 | 87 |
| 1126 | 13755 | ATAATTTTGTTCTACGCCTA | 576863 | 44 | 88 |
| 1161 | 13790 | CACTGCTGGATGGAAAAAGA | 576864 | 65 | 89 |
| 1196 | 13825 | TGGTTTAAGGGCACAAACTC | 576865 | 52 | 90 |
| 1231 | 13860 | TTGCCCACGGGTACACAGCA | 576866 | 63 | 91 |
| 1268 | 13897 | CAGATGAGGAAATAGGTGTA | 576867 | 62 | 92 |
| 1303 | 13932 | ACACATTAGGTACTATTACT | 576868 | 63 | 93 |
| 1372 | 14001 | TTTTTATGTTCCAGGCACTG | 576869 | 59 | 94 |
| 1407 | 14036 | AATAGGAAATGTTAGCTATG | 576870 | 30 | 95 |
| 1446 | 14075 | GGCACTCAACAAATACTGGC | 576871 | 72 | 96 |
| 1482 | 14111 | TACATGTAAAGCAACTAGTA | 576872 | 55 | 97 |
| 1539 | 14168 | TAAAATTTCATGAAAATCTG | 576873 | 0 | 98 |
| 1579 | 14208 | AAGTGAATACTTTATACTTT | 576874 | 0 | 99 |
| 1614 | 14243 | CATCATGAGCCTAAAGGAAA | 576875 | 51 | 100 |
| 1651 | 14280 | GGCTCTTAGGTTAAACACAC | 576876 | 43 | 101 |
| 1673 | 14302 | TGCTTCTGATTCAAGCCATT | 576877 | 65 | 102 |
| 1687 | 14316 | ATACAGGACTAAAGTGCTTC | 576878 | 74 | 103 |
| 1731 | 14360 | CAAATGGGATTTAAAATGAT | 576879 | 0 | 104 |
| 1766 | 14395 | TGACATGTAGAGAGATTAAG | 576880 | 26 | 105 |
| 1801 | 14430 | TTATTGAAATACCATCATTT | 576881 | 34 | 106 |
| 1836 | 14465 | TAGTCAGTATAATATCATTT | 576882 | 18 | 107 |

TABLE 7

| Target Start Site at SEQ ID NO: 1 | Target Start Site at SEQ ID NO: 2 | Sequence | ISIS No | % inhibition | SEQ ID NO |
|---|---|---|---|---|---|
| 851 | n/a | GCATTGAGAAGAAAGCCTTC | 571824 | 25 | 108 |
| 1337 | n/a | AAGACCTGATCCAGGAAGGC | 571836 | 53 | 109 |
| 861 | n/a | TGAGCTGATGGCATTGAGAA | 571981 | 41 | 110 |
| 890 | 14726 | ACAACGGAACAGCCACAGGT | 571983 | 66 | 111 |
| 1420 | 26405 | TTAGTGTCAAGGCTTTTCTG | 572007 | 60 | 112 |
| 75 | 1211 | GACGGCTGACACACCAAGCG | 576884 | 8 | 113 |
| 856 | n/a | TGATGGCATTGAGAAGAAAG | 576891 | 6 | 114 |
| 917 | 14753 | TTTACTTTCTCTGCACTGCT | 576892 | 68 | 115 |
| 922 | n/a | TCTTATTTACTTTCTCTGCA | 576893 | 63 | 116 |
| 940 | 16395 | GGCATAATGTTCTGACTATC | 576894 | 71 | 117 |
| 979 | 16434 | ATAACCTGGAGCATTTTCTC | 576895 | 65 | 118 |
| 1014 | 16469 | CCCTGACTCATATTTAAATG | 576896 | 70 | 119 |
| 1049 | n/a | CCAGTTGAATCCTTTAGCAG | 576897 | 51 | 120 |
| 1084 | 18233 | CATACATGACTTGCCGGAAA | 576898 | 66 | 121 |
| 1119 | 18268 | GACATCCACATCTATGTGTG | 576899 | 63 | 122 |
| 1154 | 18303 | TGTTCATGACAGGGTGGCAT | 576900 | 66 | 123 |
| 1163 | 18312 | TTATAAATATGTTCATGACA | 576901 | 51 | 124 |
| 1191 | 18340 | CAGCTCGGATCTCATGTATC | 576902 | 52 | 125 |
| 1205 | 18354 | CTCCAGAAGGCTGTCAGCTC | 576903 | 59 | 126 |
| 1238 | 18387 | GTATCCTGAGCCATGTCTTC | 576904 | 33 | 127 |
| 1273 | 18422 | AATCAGGAGTAAAGCTTTCG | 576905 | 48 | 128 |
| 1283 | n/a | AAAATATTCAAATCAGGAGT | 576906 | 23 | 129 |
| 1304 | 24306 | TCTCTGTGTAAGACATCTTG | 576907 | 51 | 130 |
| 1309 | 24311 | GAGTGTCTCTGTGTAAGACA | 576908 | 54 | 131 |
| 1314 | 24316 | CACTAGTGTCTCTGTGTA | 576909 | 50 | 132 |
| 1319 | 24321 | GCTTTCACTAGTGTCTCT | 576910 | 60 | 133 |
| 1330 | 24332 | GATCCAGGAAGGCTTTCACT | 576911 | 35 | 134 |
| 1373 | 26358 | AAAGTACTTCTGAGAGATAA | 576912 | 38 | 135 |
| 1385 | 26370 | AACTGTGCAAGGAAAGTACT | 576913 | 43 | 136 |
| 1415 | 26400 | GTCAAGGCTTTTCTGTGAAG | 576914 | 65 | 137 |
| 1472 | 26591 | AGAGATTTAAAGGGCTTTTT | 576915 | 46 | 138 |
| 1487 | 26606 | ATCTTCAGGTTCCGAAGAGA | 576916 | 53 | 139 |
| 1511 | 26630 | CCCTCTGCTGTTAAATCAAG | 576917 | 51 | 140 |
| 1522 | 26641 | TGTTAAGATCGCCCTCTGCT | 576918 | 64 | 141 |
| 1529 | 26648 | ATTATTATGTTAAGATCGCC | 576919 | 46 | 142 |
| 1535 | 26654 | AGAGCCATTATTATGTTAAG | 576920 | 36 | 143 |
| 1571 | 26690 | ATAAAGAGTGTAGGCCTGG | 576921 | 46 | 144 |
| 1598 | 26717 | ACACTAGTGTAGAAAGGTCT | 576922 | 55 | 145 |
| 1606 | 26725 | GTTCTTGCACACTAGTGTAG | 576923 | 62 | 146 |
| 1628 | 26747 | TAAAAAGTCATTAGAACATC | 576924 | 10 | 147 |

TABLE 7-continued

| Target Start Site at SEQ ID NO: 1 | Target Start Site at SEQ ID NO: 2 | Sequence | ISIS No | % inhibition | SEQ ID NO |
|---|---|---|---|---|---|
| 1644 | 26763 | TATTAAGTTACACATTTAAA | 576925 | 20 | 148 |
| 1679 | 26798 | CTTTACCAGCGATCATGATT | 576926 | 57 | 149 |
| 1725 | 26844 | TTCTGGAGTATGATCCAGGG | 576927 | 64 | 150 |
| 1752 | 24472 26871 | ACTTAACTGCAATTGCTGAG | 576928 | 66 | 151 |
| 1765 | 26884 | TGTAGTGTAACTTACTTAAC | 576929 | 60 | 152 |
| 1802 | 26921 | ATGCACCTGACATCCCCTCA | 576930 | 56 | 153 |
| 1844 | 26963 | CCCAAAAGCATAAATCTAGG | 576931 | 71 | 154 |
| 1876 | 24596 26995 | ATATTTATTATATTGTAAAC | 576932 | 0 | 155 |
| 1883 | 24603 27002 | AGCAATAATATTTATTATAT | 576933 | 1 | 156 |
| 1887 | 24607 27006 | AGATAGCAATAATATTTATT | 576934 | 0 | 157 |
| 1889 | 24609 27008 | AAAGATAGCAATAATATTTA | 576935 | 0 | 158 |
| 1892 | 24612 27011 | TTAAAAGATAGCAATAATAT | 576936 | 3 | 159 |
| 1896 | 24616 27015 | ATCTTTAAAAGATAGCAATA | 576937 | 14 | 160 |
| 1898 | 24618 27017 | ATATCTTTAAAAGATAGCAA | 576938 | 15 | 161 |
| 1901 | 24621 27020 | ATTATATCTTTAAAAGATAG | 576939 | 12 | 162 |
| 1905 | 24625 27024 | TATTATTATATCTTTAAAAG | 576940 | 6 | 163 |
| 1918 | 27037 | CAAGTTTACATCCTATTATT | 576941 | 48 | 164 |
| 1935 | 24655 27054 | AAAACAGTAGTTGTGGTCAA | 576942 | 77 | 165 |
| 1937 | 24657 27056 | AAAAAACAGTAGTTGTGGTC | 576943 | 69 | 166 |
| 1953 | 27072 | TGAATCATGTATTTCAAAAA | 576944 | 17 | 167 |
| 1988 | 27107 | GCCAACTCAGATTTCACCTT | 576945 | 71 | 168 |
| 2036 | 27155 | CTACACACCAAAGAATGCCA | 576946 | 69 | 169 |
| 2071 | 27190 | AGTTTTCAGTTGATTGCAGA | 576947 | 58 | 170 |
| 2127 | 27246 | CATCCTATGTTCAAGCTCAC | 576948 | 51 | 171 |
| 2162 | 27281 | TAAACATCTGCTTGATCAAT | 576949 | 44 | 172 |
| 2197 | 27316 | AATCCACAAAGTAGGATCTA | 576950 | 42 | 173 |
| 2232 | 27351 | ATTAGACATTTCTACAGACT | 576951 | 56 | 174 |
| 2325 | 27444 | CTCAACTACATAGAATATCA | 576952 | 45 | 175 |
| 2371 | 27490 | TTGGCAACAATTACTAAAAC | 576953 | 48 | 176 |
| 2400 | 27519 | TCAAAATAATGAAAATTAA | 576954 | 0 | 177 |
| 2409 | 27528 | CAATTTGGCTCAAAAATAAT | 576955 | 3 | 178 |
| 2429 | 27548 | GGCACAGGAGGTGCACATTT | 576956 | 60 | 179 |

TABLE 8

| Target Start Site at SEQ ID NO: 1 | Target Start Site at SEQ ID NO: 2 | Sequence | ISIS No | % inhibition | SEQ ID NO |
|---|---|---|---|---|---|
| 2451 | 27570 | TAGATTTTCTAAGGAGAAAA | 576957 | 8 | 180 |
| 2486 | 27605 | ACTGACCAGTGAAATCTGAA | 576958 | 50 | 181 |
| 2522 | 27641 | GGTAAGACTTAGCAAGAAGA | 576959 | 59 | 182 |
| 2557 | 27676 | TCTCAGAGTTGCAATGATTG | 576960 | 63 | 183 |
| 2597 | 27716 | AGATCTTATTAGTTAGTATA | 576961 | 18 | 184 |
| 2632 | 27751 | AGTACTCAAGGAACTATTTT | 576962 | 57 | 185 |
| 2679 | 27798 | GGCAAACAGCAACAACTTCA | 576963 | 71 | 186 |
| 2724 | 27843 | GCACTTCAGTAAAATTTCTC | 576964 | 69 | 187 |
| 2788 | 27907 | GGTCCAAACGCATTAAGAAA | 576965 | 58 | 188 |
| 2825 | 27944 | GAATTATATTAATCAGTTAT | 576966 | 0 | 189 |
| 2860 | 27979 | TGTGTTTGTGTAACTACAAT | 576967 | 67 | 190 |
| 2895 | 28014 | ATATTACTTCCAGAATTTTA | 576968 | 19 | 191 |
| 2949 | 28068 | GGCAGAAGGGCTCTATTACC | 576969 | 59 | 192 |
| 2992 | 28111 | CATTCGAACATGTCATTTTG | 576970 | 40 | 193 |
| 3027 | 28146 | CTGATTCATGATGGGAAAGC | 576971 | 34 | 194 |
| 3062 | 28181 | GTGGTTGTCTAAAACATCAA | 576972 | 58 | 195 |
| 3097 | 28216 | ATGACTGAGCTACAGTACAA | 576973 | 47 | 196 |
| 3132 | 28251 | GGGACACTACAAGGTAGTAT | 576974 | 56 | 197 |
| 3167 | 28286 | TTAAATAAGAATCTACCATG | 576975 | 12 | 198 |
| 3250 | 28369 | GCTTTAATAACTTATTTCAC | 576976 | 54 | 199 |
| 3282 | 28401 | AGGAGAAAAGATATATAACA | 576977 | 0 | 200 |
| 3288 | 28407 | CCATTTAGGAGAAAAGATAT | 576978 | 0 | 201 |
| n/a | 1343 | TTCACCCTCAGCGAGTACTG | 576979 | 0 | 202 |
| n/a | 1403 | AGGCTGCGGTTGTTTCCCTC | 576980 | 0 | 203 |
| n/a | 1800 | GCCAGATCCCCATCCCTTGT | 576981 | 11 | 204 |
| n/a | 2187 | TCACTTCCTTTAAGCAAGTC | 576982 | 52 | 205 |
| n/a | 2209 | AGTGATGCCCAAGTCACAAT | 576983 | 53 | 206 |
| n/a | 2214 | AGTCAAGTGATGCCCAAGTC | 576984 | 47 | 207 |
| n/a | 2219 | CCATCAGTCAAGTGATGCCC | 576985 | 60 | 208 |
| n/a | 2224 | GATTACCATCAGTCAAGTGA | 576986 | 29 | 209 |
| n/a | 2229 | CAACTGATTACCATCAGTCA | 576987 | 42 | 210 |

TABLE 8-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 2728 | GCAGTTTCCAACTGATTCAG | 576988 | 58 | 211 |
| n/a | 2760 | CGTTCTTGTTTCAGATGTAC | 576989 | 57 | 212 |
| n/a | 2862 | GCCAAACAAAATATTTTATC | 576990 | 22 | 213 |
| n/a | 2995 | TAGGTAGGCTAACCTAGTCC | 576991 | 47 | 214 |
| n/a | 3196 | TCCCAGCCCAAAGAGAAGCA | 576992 | 41 | 215 |
| n/a | 3466 | GGATCATAGCTCTCGGTAAC | 576993 | 26 | 216 |
| n/a | 3540 | AATCATAAAGCCCTCACTTC | 576994 | 7 | 217 |
| n/a | 3595 | CTGATTGGTATTTAGAAAGG | 576995 | 3 | 218 |
| n/a | 3705 | ATGCAGACATGATTACATTA | 576996 | 48 | 219 |
| n/a | 4560 | TTCATCATTAAACTGAAAAT | 576997 | 0 | 220 |
| n/a | 4613 | CTTTTAGGTTAAAAAGGTGG | 576998 | 35 | 221 |
| n/a | 4986 | ATACAGAGCCTGGCAAAACA | 576999 | 30 | 222 |
| n/a | 5036 | TTCTATTTACAGAGCATTAG | 577000 | 29 | 223 |
| n/a | 5656 | GCCTTCACATTAATTCACCA | 577001 | 62 | 224 |
| n/a | 6051 | TGTGTTATTGCCCCTAAAAA | 577002 | 24 | 225 |
| n/a | 6200 | TGTATTCACTATACTATGCC | 577003 | 52 | 226 |
| n/a | 6276 | AAGTTATTTAAAGTATAGCA | 577004 | 0 | 227 |
| n/a | 6762 | GACATTGAAGTATCAAGACA | 577005 | 34 | 228 |
| n/a | 6965 | TGTTAAGTAATCTTAGAAAA | 577006 | 0 | 229 |
| n/a | 7594 | GGCATACATTTAGAAATTCA | 577007 | 60 | 230 |
| n/a | 8309 | ACCTTATGCATCCATATTCT | 577008 | 59 | 231 |
| n/a | 8784 | GAATTCTCTTGGGAACCATT | 577009 | 42 | 232 |
| n/a | 8834 | ATATTCAACTACAGGATTTA | 577010 | 13 | 233 |
| n/a | 8884 | ATGTGTTCTTTAGATACATC | 577011 | 42 | 234 |
| n/a | 9510 | CCTTATACAGATACATGCTG | 577012 | 37 | 235 |
| n/a | 9663 | TAGATGCAATTACTATTTTC | 577013 | 34 | 236 |
| n/a | 10742 | TGTACTTCCCAAACTTGAAC | 577014 | 24 | 237 |
| n/a | 10845 | CTGAAGCTCAACAACACCAA | 577015 | 49 | 238 |
| n/a | 11684 | GTCTATAGAATCAAACTGAA | 577016 | 38 | 239 |
| n/a | 11851 | TTGAATCAATACCTAACCTC | 577017 | 23 | 240 |
| n/a | 11991 | TGCCTCTTTTAGAAAAGATC | 577018 | 44 | 241 |
| n/a | 12042 | ATGGAATCATTGGTTTATCG | 577019 | 43 | 242 |
| n/a n/a | 12069 12333 | AAAGCTCACTTTTATTCTTT | 577020 | 37 | 243 |
| n/a | 12170 | GGTGCCGCCACCATGCCCGG | 577021 | 0 | 244 |
| n/a | 12464 | GAGAGAAGCTGGGCAATAAA | 577022 | 2 | 245 |
| n/a | 12514 | TCTGACCCTGCACAATAAAG | 577023 | 0 | 246 |
| n/a | 13016 | ATAGTGTGTGATTCAAAACG | 577024 | 17 | 247 |
| n/a | 13348 | ACTGTATCAGCTATCTAAAA | 577025 | 22 | 248 |
| n/a | 14540 | TTATTTGTATAGGAACCTAC | 577026 | 44 | 249 |
| n/a | 14699 | TGTGAGCTGATGGCACTGTA | 577027 | 61 | 250 |
| n/a | 14758 | CCTTATTTACTTTCTCTGCA | 577028 | 71 | 251 |
| n/a | 15587 | GGAATAAGGTCACTAGTTCG | 577029 | 69 | 252 |
| n/a | 17187 | ATTTGCAACAATTTTTAAAT | 577030 | 8 | 253 |
| n/a | 21808 | ATAAACTACCAATGATATCC | 577031 | 13 | 254 |
| n/a | 24337 | TACCTGATCCAGGAAGGCTT | 577032 | 40 | 255 |
| n/a | 24565 | TTCCCGAAGCATAAATCTAG | 577033 | 53 | 256 |
| n/a | 25549 | TTGAGAAGCATGAAATTCCA | 577034 | 48 | 257 |

TABLE 9

| Target Start Site at SEQ ID NO: 1 | Target Start Site at SEQ ID NO: 2 | Sequence | ISIS No | % inhibition | SEQ ID NO |
|---|---|---|---|---|---|
| 310 | 7990 | GCCTTACTCTAGGACCAAGA | 576816 | 90 | 40 |
| 75 | 1211 | GACGGCTGACACACCAAGCG | 576884 | 0 | 113 |
| 2 | 1138 | GCGGGACACCGTAGGTTACG | 577035 | 0 | 258 |
| 10 | 1146 | CTTTCCTAGCGGGACACCGT | 577036 | 1 | 259 |
| 18 | 1154 | GCACCTCTCTTTCCTAGCGG | 577037 | 0 | 260 |
| 26 | 1162 | TGTTTGACGCACCTCTCTTT | 577038 | 0 | 261 |
| 34 | 1170 | CTTGTCGCTGTTTGACGCAC | 577039 | 0 | 262 |
| 42 | 1178 | GGGCGGAACTTGTCGCTGTT | 577040 | 0 | 263 |
| 83 | 1219 | GCAGCAGGGACGGCTGACAC | 577041 | 0 | 264 |
| 95 | 1231 | AGAAGCAACCGGGCAGCAGG | 577042 | 0 | 265 |
| 103 | 1239 | CCCAAAAGAGAAGCAACCGG | 577043 | 0 | 266 |
| 111 | 1247 | ACCCCGCCCCCAAAAGAGAA | 577044 | 1 | 267 |
| 119 | 1255 | CTTGCTAGACCCCGCCCCCA | 577045 | 0 | 268 |
| 127 | 1263 | CACCTGCTCTTGCTAGACCC | 577046 | 0 | 269 |
| 135 | 1271 | TAAACCCACACCTGCTCTTG | 577047 | 0 | 270 |
| 139 | 1275 | CTCCTAAACCCACACCTGCT | 577048 | 0 | 271 |
| n/a | 1283 | ACACACACCTCCTAAACCCA | 577049 | 0 | 272 |
| n/a | 1291 | AAACAAAACACACACCTCC | 577050 | 5 | 273 |
| n/a | 1299 | GGTGGGAAAACAAAAACAC | 577051 | 1 | 274 |
| n/a | 1326 | CTGTGAGAGCAAGTAGTGGG | 577052 | 3 | 275 |
| n/a | 1334 | AGCGAGTACTGTGAGAGCAA | 577053 | 0 | 276 |

TABLE 9-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 1342 | TCACCCTCAGCGAGTACTGT | 577054 | 0 | 277 |
| n/a | 1358 | TCAGGTCTTTTCTTGTTCAC | 577055 | 0 | 278 |
| n/a | 1366 | AATCTTTATCAGGTCTTTTC | 577056 | 16 | 279 |
| n/a | 1374 | TTCTGGTTAATCTTTATCAG | 577057 | 22 | 280 |
| n/a | 1382 | TTGTTTTCTTCTGGTTAATC | 577058 | 19 | 281 |
| n/a | 1390 | TTCCCTCCTTGTTTTCTTCT | 577059 | 28 | 282 |
| n/a | 1398 | GCGGTTGTTTCCCTCCTTGT | 577060 | 17 | 283 |
| n/a | 1406 | TACAGGCTGCGGTTGTTTCC | 577061 | 28 | 284 |
| n/a | 1414 | GAGCTTGCTACAGGCTGCGG | 577062 | 23 | 285 |
| n/a | 1422 | GAGTTCCAGAGCTTGCTACA | 577063 | 14 | 286 |
| n/a | 1430 | CGACTCCTGAGTTCCAGAGC | 577064 | 0 | 287 |
| n/a | 1446 | CCCGGCCCCTAGCGCGCGAC | 577065 | 0 | 288 |
| n/a | 1454 | GCCCCGGCCCCGCCCCTAG | 577066 | 0 | 289 |
| n/a | 1465 | ACCACGCCCCGGCCCCGGCC | 577067 | 0 | 290 |
| n/a | 1473 | CCGCCCCGACCACGCCCCGG | 577068 | 0 | 291 |
| n/a | 1481 | CCCCGGGCCCGCCCCGACCA | 577069 | 0 | 292 |
| n/a | 1495 | CGCCCCGGGCCCGCCCCCGG | 577070 | 0 | 293 |
| n/a | 1503 | CGCAGCCCCGCCCCGGGCCC | 577071 | 0 | 294 |
| n/a | 1511 | ACCGCAACCGCAGCCCCGCC | 577072 | 0 | 295 |
| n/a | 1519 | GCGCAGGCACCGCAACCGCA | 577073 | 18 | 296 |
| n/a | 1520 | GGCGCAGGCACCGCAACCGC | 577074 | 17 | 297 |
| n/a | 1536 | CGCCTCCGCCGCCGCGGGCG | 577075 | 32 | 298 |
| n/a | 1544 | ACCGCCTGCGCCTCCGCCGC | 577076 | 43 | 299 |
| n/a | 1552 | CACTCGCCACCGCCTGCGCC | 577077 | 52 | 300 |
| n/a | 1553 | CCACTCGCCACCGCCTGCGC | 577078 | 52 | 301 |
| n/a | 1853 | GGTCCCCGGGAAGGAGACAG | 577079 | 41 | 302 |
| n/a | 2453 | AACAACTGGTGCATGGCAAC | 577080 | 42 | 303 |
| n/a | 2753 | GTTTCAGATGTACTATCAGC | 577081 | 63 | 304 |
| n/a | 3053 | AAGGTGAAGTTCATATCACT | 577082 | 10 | 305 |
| n/a | 3452 | GGTAACTTCAAACTCTTGGG | 577083 | 70 | 306 |
| n/a | 3752 | GGTTCATGAGAGGTTTCCCA | 577084 | 53 | 307 |
| n/a | 4052 | TACTGAATTGCTTAGTTTTA | 577085 | 25 | 308 |
| n/a | 4425 | CTAACAGAATAAGAAAAAAA | 577086 | 0 | 309 |
| n/a | 5025 | GAGCATTAGATGAGTGCTTT | 577087 | 52 | 310 |
| n/a | 5325 | TGCATTCCTAAGCAATGTGT | 577088 | 28 | 311 |
| n/a | 5661 | TCTAGGCCTTCACATTAATT | 577089 | 37 | 312 |
| n/a | 5961 | CCTGTCTATGCCTAGGTGAA | 577090 | 19 | 313 |
| n/a | 6261 | TAGCACATACAATTATTACA | 577091 | 38 | 314 |
| n/a | 6566 | GAGGAGAAGAACATAAACGC | 577092 | 20 | 315 |
| n/a | 6866 | TACCACAAGTCTGGAGCCAT | 577093 | 27 | 316 |
| n/a | 7166 | GATACTGGATTGTTGAAACT | 577094 | 1 | 317 |
| n/a | 7466 | TAGTATGACTGGAGATTTGG | 577095 | 1 | 318 |
| n/a | 7766 | ATCAAAACCCCAAATGATTT | 577096 | 13 | 319 |
| 160 | 7840 | ATCCAAATGCTCCGGAGATA | 577097 | 78 | 320 |
| 190 | 7870 | TCGACATCACTGCATTCCAA | 577098 | 95 | 321 |
| 220 | 7900 | CAACAGCTGGAGATGGCGGT | 577099 | 56 | 322 |
| 250 | 7930 | ATTTGCCACTTAAAGCAATC | 577100 | 62 | 323 |
| 340 | 8020 | GTACCTGTTCTGTCTTTGGA | 577101 | 76 | 324 |
| 370 | 8050 | CAAGAAAAGTTATTTCTCCA | 577102 | 65 | 325 |
| 400 | 8080 | GAAGGATTTCTCCATTTAGA | 577103 | 50 | 326 |
| 430 | 8110 | TTACATCTATAGCACCACTC | 577104 | 73 | 327 |
| 460 | 8140 | TCACTCCTTTTCAGACAAG | 577105 | 73 | 328 |
| 490 | 8170 | AGTTTCCATCAAAGATTAAT | 577106 | 55 | 329 |
| 520 | 8200 | ATAGTCCATATGTGCTGCGA | 577107 | 57 | 330 |
| 550 | 8230 | AACTAAGTTCTGTCTGTGGA | 577108 | 71 | 331 |
| 580 | 8260 | CAACACACACTCTATGAAGT | 577109 | 54 | 332 |
| 610 | 8290 | TTCCTTTCCGGATTATATGT | 577110 | 0 | 333 |

TABLE 10

| Target SEQ ID NO | Target Start Site | ISIS No | Sequence | % inhibition | SEQ ID NO |
|---|---|---|---|---|---|
| 3 | 751 | 576885 | TTTCCATTACAGGAATCACT | 63 | 334 |
| 3 | 807 | 576886 | ATCAGCCTATATCTATTTCC | 15 | 335 |
| 3 | 855 | 576887 | TCAATGACCAGGCGGTCCCC | 0 | 336 |
| 3 | 905 | 576888 | CTTTTTATGGAAAAGGAAAA | 0 | 337 |
| 3 | 984 | 576889 | TGTTTCCCCAAAAATTTCTG | 0 | 338 |
| 4 | 50 | 576890 | AGATATCCACTCGCCACCGC | 42 | 339 |

Example 2

Dose-dependent Antisense Inhibition of Human C9ORF72 in HepG2 Cells

Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 82.3 nM, 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3750 was used to measure mRNA levels. C9ORF72 mRNA levels were adjusted according to total RNA content, as measured by RIBOGREEN®. Results are presented as percent inhibition of C9ORF72, relative to untreated control cells.

The half maximal inhibitory concentration ($IC_{50}$) of each oligonucleotide is also presented in Tables 11-13. As illustrated, C9ORF72 mRNA levels were reduced in a dose-dependent manner in the antisense oligonucleotide treated cells.

Example 3

Dose-dependent Antisense Inhibition of Human C9ORF72 in HepG2 Cells

Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 total mRNA levels, as well as mRNA levels of the exon 1 transcript, were measured by quantitative real-time PCR. Human C9ORF72 primer probe set RTS3750 was used to measure total C9ORF72 mRNA levels. Primer probe set RTS3905 (forward sequence GGGTCTAGCAAGAGCAGGTG, designated herein as

TABLE 11

| ISIS No | 82.3 nM | 246.9 nM | 740.7 nM | 2222.2 nM | 6666.7 nM | 20000.0 nM | $IC_{50}$ (µM) |
|---|---|---|---|---|---|---|---|
| 576816 | 5 | 23 | 49 | 76 | 91 | 96 | 0.9 |
| 576817 | 8 | 2 | 6 | 29 | 58 | 83 | 4.7 |
| 576818 | 0 | 22 | 31 | 68 | 87 | 90 | 1.4 |
| 576819 | 0 | 12 | 44 | 72 | 81 | 86 | 1.4 |
| 576820 | 18 | 24 | 52 | 78 | 91 | 93 | 0.7 |
| 576841 | 23 | 19 | 29 | 52 | 75 | 85 | 1.6 |
| 576842 | 6 | 12 | 13 | 37 | 53 | 83 | 4.1 |
| 576860 | 9 | 24 | 54 | 70 | 83 | 87 | 1.0 |
| 576878 | 1 | 9 | 26 | 61 | 77 | 83 | 2.0 |
| 576931 | 16 | 21 | 24 | 49 | 77 | 83 | 1.8 |
| 576942 | 6 | 16 | 26 | 57 | 78 | 85 | 1.8 |

TABLE 12

| ISIS No | 82.3 nM | 246.9 nM | 740.7 nM | 2222.2 nM | 6666.7 nM | 20000.0 nM | $IC_{50}$ (µM) |
|---|---|---|---|---|---|---|---|
| 576894 | 9 | 30 | 38 | 61 | 75 | 84 | 1.3 |
| 576896 | 17 | 17 | 28 | 47 | 66 | 76 | 2.5 |
| 576927 | 3 | 26 | 40 | 60 | 79 | 81 | 1.5 |
| 576943 | 37 | 37 | 55 | 77 | 84 | 82 | 0.4 |
| 576945 | 20 | 41 | 56 | 73 | 83 | 84 | 0.6 |
| 576946 | 8 | 28 | 46 | 69 | 81 | 88 | 1.0 |
| 576963 | 0 | 0 | 25 | 51 | 63 | 83 | 2.9 |
| 576964 | 11 | 18 | 37 | 58 | 73 | 77 | 1.8 |
| 576967 | 19 | 31 | 48 | 68 | 77 | 85 | 0.9 |
| 577028 | 6 | 19 | 25 | 59 | 79 | 88 | 1.6 |
| 577029 | 7 | 22 | 44 | 67 | 77 | 85 | 1.3 |

TABLE 13

| ISIS No | 82.3 nM | 246.9 nM | 740.7 nM | 2222.2 nM | 6666.7 nM | 20000.0 nM | $IC_{50}$ (µM) |
|---|---|---|---|---|---|---|---|
| 576960 | 0 | 12 | 28 | 49 | 58 | 78 | 3.2 |
| 576974 | 25 | 45 | 65 | 70 | 65 | 78 | 0.5 |
| 576816 | 18 | 36 | 53 | 82 | 91 | 95 | 0.6 |
| 577097 | 22 | 20 | 31 | 63 | 82 | 94 | 1.1 |
| 577101 | 16 | 23 | 39 | 62 | 80 | 89 | 1.2 |
| 577105 | 0 | 4 | 30 | 48 | 78 | 92 | 2.0 |
| 577104 | 4 | 1 | 16 | 56 | 80 | 92 | 2.0 |
| 577108 | 0 | 0 | 24 | 52 | 76 | 83 | 2.9 |
| 577083 | 0 | 0 | 24 | 50 | 73 | 74 | 3.0 |
| 577078 | 0 | 0 | 10 | 15 | 30 | 75 | 10.8 |
| 577077 | 0 | 0 | 22 | 22 | 51 | 83 | 5.0 |

SEQ ID NO: 18; reverse sequence GTCTTGGCAACA-GCTGGAGAT, designated herein as SEQ ID NO: 19; probe sequence TGATGTCGACTCTTTGCCCACCGC, designated herein as SEQ ID NO: 20) was used to measure exon 1 message transcript. C9ORF72 mRNA levels were adjusted according to total RNA content, as measured by RIBOGREEN®. Results are presented as percent inhibition of C9ORF72, relative to untreated control cells.

The half maximal inhibitory concentration (IC$_{50}$) of each oligonucleotide is also presented in Tables 14 and 15. As illustrated, C9ORF72 mRNA levels were reduced in a dose-dependent manner in the antisense oligonucleotide treated cells. 'n.d.' indicates that there is no data for that particular dose.

TABLE 14

% inhibition of total C9ORF72 mRNA levels

| ISIS No | 246.9 nM | 740.7 nM | 2222.2 nM | 6666.7 nM | 20000.0 nM | IC$_{50}$ (µM) |
|---|---|---|---|---|---|---|
| 576816 | 29 | 53 | 84 | 90 | 92 | 0.60 |
| 576820 | 20 | 42 | 70 | 87 | 75 | 1.19 |
| 576860 | 25 | 53 | 72 | 86 | 85 | 0.80 |
| 576974 | 36 | 49 | 64 | 65 | 68 | 0.95 |
| 577041 | 3 | 0 | 0 | 0 | 0 | >20.00 |
| 577042 | 0 | 2 | 0 | 3 | 0 | >20.00 |
| 577061 | 0 | 3 | 0 | 4 | 0 | >20.00 |
| 577065 | 7 | 0 | 1 | 6 | 0 | >20.00 |
| 577069 | 3 | 0 | 3 | 0 | 0 | >20.00 |
| 577073 | 7 | 0 | 8 | 11 | 0 | >20.00 |
| 577074 | 0 | 7 | 11 | 15 | 0 | >20.00 |
| 577078 | 0 | 2 | 20 | 65 | 81 | 5.22 |
| 577083 | 0 | 19 | 55 | 71 | 75 | 3.35 |
| 577088 | 6 | 11 | 49 | 61 | 74 | 3.93 |
| 577097 | 3 | 38 | 62 | 78 | 82 | 1.94 |

TABLE 15

% inhibition of C9ORF72 exon 1 mRNA levels

| ISIS No | 246.9 nM | 740.7 nM | 2222.2 nM | 6666.7 nM | 20000.0 nM | IC$_{50}$ (µM) |
|---|---|---|---|---|---|---|
| 576794 | 42 | 67 | n.d. | 93 | 87 | 0.27 |
| 576816 | 45 | 78 | 93 | n.d. | n.d. | 0.26 |
| 576820 | 54 | 65 | 92 | 98 | 94 | <0.247 |
| 576860 | 43 | 36 | 71 | 95 | 91 | 0.66 |
| 577041 | 0 | 0 | 49 | 4 | 31 | >20.00 |
| 577042 | 9 | 15 | 0 | 33 | 12 | >20.00 |
| 577061 | 8 | 36 | 70 | 67 | 76 | 2.03 |
| 577065 | 20 | 55 | 67 | 82 | 62 | 1.06 |
| 577069 | 22 | 24 | 61 | 74 | 70 | 2.16 |
| 577073 | 4 | 62 | 69 | 82 | 81 | 1.21 |
| 577074 | 8 | 49 | 69 | 85 | 85 | 1.29 |
| 577078 | 0 | 21 | 59 | 81 | n.d. | 1.90 |
| 577083 | 30 | 43 | 85 | 88 | 92 | 0.71 |
| 577088 | 38 | 44 | 79 | 87 | 91 | 0.61 |
| 577097 | 17 | 47 | 52 | 94 | 89 | 1.27 |

Example 4

Antisense Inhibition of Human C9ORF72 in HepG2 Cells

Antisense oligonucleotides were designed targeting the hexanucleotide repeat expansion of a C9ORF72 nucleic acid and were tested for their effects on C9ORF72 mRNA in vitro. The antisense oligonucleotides were tested in a series of experiments that had similar culture conditions. The results for each experiment are presented in separate tables shown below. ISIS 576816 and ISIS 577065 were included in these assays for comparison. Cultured C9ORF72 fibroblasts at a density of 35,000 cells per well were transfected using electroporation with 7,000 nM antisense oligonucleotide. After a treatment period of approximately 24 hours, RNA was isolated from the cells and C9ORF72 mRNA levels were measured by quantitative real-time PCR. Human primer probe sets RTS3750, RTS 3905, or RTS4097 (forward sequence CAAGCCACCGTCTCACTCAA, designated herein as SEQ ID NO: 24; reverse sequence GTAGT-GCTGTCTACTCCAGAGAGTTACC, designated herein as SEQ ID NO: 25; probe sequence CTTGGCTTCCCT-CAAAAGACTGGCTAATGT, designated herein as SEQ ID NO: 26) were used to measure mRNA levels. RTS3750 targets exon 2 of the mRNA transcripts and, therefore, measures total mRNA transcripts. RTS3905 targets the hexanucleotide repeat expansion containing transcript and, therefore, measures only mRNA transcripts that contain the hexanucleotide repeat expansion. RTS4097 targets the gene sequence at a site 3' of the hexanucleotide repeat expansion. mRNA levels were adjusted according to total RNA content, as measured by RIBOGREEN®. Results are presented as percent inhibition of C9ORF72, relative to untreated control cells. 'n.d.' indicates that there is no data for that particular antisense oligonucleotide.

The antisense oligonucleotides in Table 16 were designed as uniform MOE oligonucleotides, or 3-10-3 MOE, 4-10-3 MOE, 4-10-4 MOE, 5-10-4 MOE, or 5-10-5 MOE gapmers. The uniform MOE oligonucleotides are 20 nucleosides in length, wherein each nucleoside comprises a 2'-MOE group. The 3-10-3 MOE gapmers are 16 nucleosides in length, wherein the central gap segment comprises ten 2'-deoxynucleosides and is flanked by wing segments on both the 5' end and on the 3' end comprising three nucleosides each. The 4-10-3 gapmers are 17 nucleosides in length, wherein the central gap segment comprises ten 2'-deoxynucleosides and is flanked by wing segments on both the 5' end and on the 3' end comprising four and three nucleosides, respectively. The 4-10-4 gapmers are 18 nucleosides in length, wherein the central gap segment comprises ten 2'-deoxynucleosides and is flanked by wing segments on both the 5' end and on the 3' end comprising four nucleosides each. The 5-10-4 gapmers are 19 nucleosides in length, wherein the central gap segment comprises ten 2'-deoxynucleosides and is flanked by wing segments on both the 5' end and on the 3' end comprising five and four nucleosides, respectively. The 5-10-5 gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment comprises a 2'-MOE group. The internucleoside linkages throughout each oligonucleotide are phosphorothioate linkages. All cytosine residues throughout each oligonucleotide are 5-methylcytosines. "Start site" indicates the 5'-most nucleoside to which the antisense oligonucleotide is targeted in the human gene sequence. "Stop site" indicates the 3'-most nucleoside to which the antisense oligonucleotide is targeted human gene sequence. Each antisense oligonucleotide listed in Table 16 is targeted to the human C9ORF72 genomic sequence, designated herein as SEQ ID NO: 2 (the complement of GENBANK Accession No. NT_008413.18 truncated from nucleosides 27535000 to 27565000) or SEQ ID NO: 13, which is an expanded version of the hexanucleotide repeat from intron 1 of the C9ORF72 gene.

The data indicates that certain antisense oligonucleotides preferentially inhibit levels of C9ORF72 mRNA transcript levels that contain the hexanucleotide repeat.

TABLE 16

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1457 | 1 7 13 | Uniform MOE | CCGGCCCCGGCCC CGGCCCC | 573674 | 0 | 34 | 0 | 340 |
| 1458 | 2 8 14 | Uniform MOE | CCCGGCCCCGGCC CCGGCCC | 573675 | 0 | 28 | 0 | 341 |
| 1459 | 3 9 15 | Uniform MOE | CCCCGGCCCCGGC CCCGGCC | 573676 | 0 | 34 | 0 | 342 |
| 1460 | 4 10 16 | Uniform MOE | GCCCCGGCCCCGG CCCCGGC | 573677 | 4 | 41 | 0 | 343 |
| n/a | 5 11 17 | Uniform MOE | GGCCCCGGCCCCG GCCCCGG | 573678 | 12 | 11 | 6 | 344 |
| n/a | 6 12 | Uniform MOE | CGGCCCCGGCCCC GGCCCCG | 573679 | 0 | 0 | 0 | 345 |
| 1457 | 1 7 13 | Uniform MOE | CGGCCCCGGCCCC GGCCCC | 573680 | 10 | 6 | 0 | 346 |
| 1458 | 2 8 14 | Uniform MOE | CCGGCCCCGGCCC CGGCCC | 573681 | 13 | 23 | 0 | 347 |
| 1459 | 3 9 15 | Uniform MOE | CCCGGCCCCGGCC CCGGCC | 573682 | 2 | 48 | 0 | 348 |
| 1460 | 4 10 16 | Uniform MOE | CCCCGGCCCCGGC CCCGGC | 573683 | 0 | 38 | 0 | 349 |
| 1461 | 5 11 17 | Uniform MOE | GCCCCGGCCCCGG CCCCGG | 573684 | 0 | 0 | 0 | 350 |
| n/a | 6 12 18 | Uniform MOE | GGCCCCGGCCCCG GCCCCG | 573685 | 0 | 27 | 0 | 351 |
| 1457 | 1 7 | Uniform MOE | GGCCCCGGCCCCG GCCCC | 573686 | 0 | 40 | 0 | 352 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| | 13 19 | | | | | | | |
| 1458 | 2 8 14 | Uniform MOE | CGGCCCCGGCCCC GGCCC | 573687 | 0 | 0 | 0 | 353 |
| 1459 | 3 9 15 | Uniform MOE | CCGGCCCCGGCCC CGGCC | 573688 | 22 | 0 | 0 | 354 |
| 1460 | 4 10 16 | Uniform MOE | CCCGGCCCCGGCC CCGGC | 573689 | 0 | 22 | 0 | 355 |
| 1461 | 5 11 17 | Uniform MOE | CCCCGGCCCCGGC CCCGG | 573690 | 15 | 43 | 0 | 356 |
| 1462 | 6 12 18 | Uniform MOE | GCCCCGGCCCCGG CCCCG | 573691 | 10 | 16 | 0 | 357 |
| 1457 1463 | 1 7 13 19 | Uniform MOE | GCCCCGGCCCCGG CCCC | 573692 | 6 | 65 | 0 | 358 |
| 1458 | 2 8 14 20 | Uniform MOE | GGCCCCGGCCCCG GCCC | 573693 | 9 | 0 | 0 | 359 |
| 1459 | 3 9 15 | Uniform MOE | CGGCCCCGGCCCC GGCC | 573694 | 10 | 0 | 0 | 360 |
| 1460 | 4 10 16 | Uniform MOE | CCGGCCCCGGCCC CGGC | 573695 | 3 | 42 | 0 | 361 |
| 1461 | 5 11 17 | Uniform MOE | CCCGGCCCCGGCC CCGG | 573696 | 0 | 23 | 0 | 362 |
| 1462 | 6 12 18 | Uniform MOE | CCCCGGCCCCGGC CCCG | 573697 | 0 | 28 | 0 | 363 |
| 1457 1463 | 1 7 13 19 | Uniform MOE | CCCCGGCCCCGGC CCC | 573698 | 1 | 68 | 0 | 364 |
| 1458 1464 | 2 8 14 20 | Uniform MOE | GCCCCGGCCCCGG CCC | 573699 | 0 | 31 | 0 | 365 |
| 1459 | 3 9 15 21 | Uniform MOE | GGCCCCGGCCCCG GCC | 573700 | 7 | 2 | 2 | 366 |
| 1460 | 4 10 16 | Uniform MOE | CGGCCCCGGCCCC GGC | 573701 | 15 | 1 | 8 | 367 |
| 1461 | 5 11 17 | Uniform MOE | CCGGCCCCGGCCC CGG | 573702 | 26 | 0 | 0 | 368 |
| 1462 | 6 12 | Uniform MOE | CCCGGCCCCGGCC | 573703 | 12 | 52 | 10 | 369 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| | 18 | | | | | | | |
| 1457 | 1 7 13 | 5-10-5 MOE | CCGGCCCCGGCCC CGGCCCC | 573716 | 0 | 93 | 46 | 340 |
| 1458 | 2 8 14 | 5-10-5 MOE | CCCGGCCCCGGCC CCGGCCC | 573717 | 0 | 98 | 0 | 341 |
| 1459 | 3 9 15 | 5-10-5 MOE | CCCCGGCCCCGGC CCCGGCC | 573718 | 0 | 98 | 2 | 342 |
| 1460 | 4 10 16 | 5-10-5 MOE | GCCCCGGCCCCGG CCCCGGC | 573719 | 0 | 68 | 19 | 343 |
| n/a | 5 11 17 | 5-10-5 MOE | GGCCCCGGCCCCG GCCCCGG | 573720 | 13 | 90 | 18 | 344 |
| n/a | 6 12 18 | 5-10-5 MOE | CGGCCCCGGCCCC GGCCCCG | 573721 | 0 | 98 | 18 | 345 |
| 1457 | 1 7 13 | 5-10-4 MOE | CGGCCCCGGCCCC GGCCCC | 573722 | 0 | 97 | 0 | 346 |
| 1458 | 2 8 14 | 5-10-4 MOE | CCGGCCCCGGCCC CGGCCC | 573723 | 0 | n.d. | 8 | 347 |
| 1459 | 3 9 15 | 5-10-4 MOE | CCCGGCCCCGGCC CCGGCC | 573724 | 0 | 94 | 28 | 348 |
| 1460 | 4 10 16 | 5-10-4 MOE | CCCCGGCCCCGGC CCCGGC | 573725 | 0 | 94 | 7 | 349 |
| 1461 | 5 11 17 | 5-10-4 MOE | GCCCCGGCCCCGG CCCCGG | 573726 | 0 | n.d. | 28 | 350 |
| n/a | 6 12 18 | 5-10-4 MOE | GGCCCCGGCCCCG GCCCCG | 573727 | 0 | 98 | 40 | 351 |
| 1457 | 1 7 13 19 | 4-10-4 MOE | GGCCCCGGCCCCG GCCCC | 573728 | 0 | 97 | 19 | 352 |
| 1458 | 2 8 14 | 4-10-4 MOE | CGGCCCCGGCCCC GGCCC | 573729 | 0 | n.d. | 36 | 353 |
| 1459 | 3 9 15 | 4-10-4 MOE | CCGGCCCCGGCCC CGGCC | 573730 | 0 | 94 | 24 | 354 |
| 1460 | 4 10 16 | 4-10-4 MOE | CCCGGCCCCGGCC CCGGC | 573731 | 0 | 97 | 13 | 355 |
| 1461 | 5 11 17 | 4-10-4 MOE | CCCCGGCCCCGGC CCCGG | 573732 | 0 | 97 | 1 | 356 |
| 1462 | 6 12 18 | 4-10-4 MOE | GCCCCGGCCCCGG CCCCG | 573733 | 0 | n.d. | 0 | 357 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1457 1463 | 1 7 13 19 | 4-10-3 MOE | GCCCCGGCCCCGG CCCC | 573734 | 0 | 96 | 0 | 358 |
| 1458 | 2 8 14 20 | 4-10-3 MOE | GGCCCCGGCCCCG GCCC | 573735 | 0 | 94 | 21 | 359 |
| 1459 | 3 9 15 | 4-10-3 MOE | CGGCCCCGGCCCC GGCC | 573736 | 0 | 93 | 43 | 360 |
| 1460 | 4 10 16 | 4-10-3 MOE | CCGGCCCCGGCCC CGGC | 573737 | 0 | 96 | 19 | 361 |
| 1461 | 5 11 17 | 4-10-3 MOE | CCCGGCCCCGGCC CCGG | 573738 | 0 | n.d. | 24 | 362 |
| 1462 | 6 12 18 | 4-10-3 MOE | CCCCGGCCCCGGC CCCG | 573739 | 0 | n.d. | 34 | 363 |
| 1457 1463 | 1 7 13 19 | 3-10-3 MOE | CCCCGGCCCCGGC CCC | 573740 | 0 | n.d. | 4 | 364 |
| 1458 1464 | 2 8 14 20 | 3-10-3 MOE | GCCCCGGCCCCGG CCC | 573741 | 0 | 95 | 6 | 365 |
| 1459 | 3 9 15 21 | 3-10-3 MOE | GGCCCCGGCCCCG GCC | 573742 | 23 | 97 | 49 | 366 |
| 1460 | 4 10 16 | 3-10-3 MOE | CGGCCCCGGCCCC GGC | 573743 | 0 | 96 | 0 | 367 |
| 1461 | 5 11 17 | 3-10-3 MOE | CCGGCCCCGGCCC CGG | 573744 | 0 | 94 | 34 | 368 |
| 1462 | 6 12 18 | 3-10-3 MOE | CCCGGCCCCGGCC CCG | 573745 | 0 | n.d. | 8 | 369 |
| 7990 | n/a | 5-10-5 MOE | GCCTTACTCTAGG ACCAAGA | 576816 | 83 | 91 | 29 | 40 |
| 1446 | n/a | 5-10-5 MOE | CCCGGCCCCTAGC GCGCGAC | 577065 | 0 | 87 | 34 | 288 |

Example 5

In Vivo Rodent Inhibition and Tolerability with Treatment of C9ORF72 Antisense Oligonucleotides In order to assess the tolerability of inhibition of C9ORF72 expression in vivo, antisense oligonucleotides targeting a murine C9ORF72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 11 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A; wherein 's' denotes a phosphorothioate internucleoside linkage, 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 12 (GENBANK Accession No. NM_ 001007702.1).

Mouse Experiment 1

Groups of 4 C57BL/6 mice each were injected with 50 µg, 100 µg, 300 µg, 500 µg, or 700 µg of ISIS 571883 administered via an intracerebroventricular bolus injection. A control group of four C57/BL6 mice were similarly treated with PBS. Animals were anesthetized with 3% isofluorane and placed in a stereotactic frame. After sterilizing the surgical site, each mouse was injected -0.2 mm anterioposterior from the bregma na d 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9ORF72 mRNA expression. C9ORF72 mRNA expression was measured by RT-PCR. The data is presented in Table 17. The results indicate that treatment with increasing doses of ISIS 571883 resulted in dose-dependent inhibition of C9ORF72 mRNA expression.

The induction of the microglial marker AIF-1 as a measure of CNS toxicity was also assessed. The data is presented in Table 18. The results indicate that treatment with increasing doses of ISIS 571883 did not result in significant increases in AIF-1 mRNA expression. Hence, the injection of ISIS 571883 was deemed tolerable in this model.

TABLE 17

Percentage inhibition of C9ORF72 mRNA expression compared to the PBS control

| Dose (µg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 18

Percentage expression of AIF-1 mRNA expression compared to the PBS control

| Dose (µg) | Posterior brain | Spinal cord |
|---|---|---|
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 µg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 19 and 20. The results indicate that there were no significant changes in the motor behavior of the mice as a result of antisense inhibition of ISIS 571883 or due to the ICV injection. Hence, antisense inhibition of C9ORF72 was deemed tolerable in this model.

TABLE 19

Latency to fall (sec) in the rotarod assay

| Weeks after injection | PBS | ISIS 571883 |
|---|---|---|
| 0 | 66 | 66 |
| 4 | 91 | 70 |
| 8 | 94 | 84 |

TABLE 20

Mean hindlimb grip strength (g) in the grip strength assay

| Weeks after injection | PBS | ISIS 571883 |
|---|---|---|
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 µg, 1,000 µg, or 3,000 µg of ISIS 603538 administered via an intrathecal bolus injection. A control group of four Sprague-Dawley rats were similarly treated with PBS. Animals were anesthetized with 3% isofluorane and placed in a stereotactic frame. After sterilizing the surgical site, each rat was injected with 30 µL of ASO solution administered via 8 cm intrathecal catheter 2 cm into the spinal canal with a 50 µL flush. The rats were allowed to recover for 4 weeks, after which animals were euthanized according to a humane protocol approved by the Institutional Animal Care and Use Committee.

RNA Analysis

RNA was extracted from a 2-3 mm brain section posterior to the injection stie, from brain frontal cortex, and from the cervical and lumbar sections of the spinal cord tissue for analysis of C9ORF72 mRNA expression. C9ORF72 mRNA expression was measured by RT-PCR. The data is presented in Table 21. The results indicate that treatment with increasing doses of ISIS 603538 resulted in dose-dependent inhibition of C9ORF72 mRNA expression.

The induction of the microglial marker AIF-1 as a measure of CNS toxicity was also assessed. The data is presented in Table 22. The results indicate that treatment with increasing doses of ISIS 603538 did not result in significant increases in AIF-1 mRNA expression. Hence, the injection of ISIS 603538 was deemed tolerable in this model.

TABLE 21

Percentage inhibition of C9ORF72 mRNA expression compared to the PBS control

| Dose (μg) | Brain (1 mm section) | Cortex | Spinal cord (lumbar) | Spinal cord (cervical) |
|---|---|---|---|---|
| 700 | 21 | 4 | 86 | 74 |
| 1000 | 53 | 49 | 88 | 82 |
| 3000 | 64 | 62 | 88 | 80 |

TABLE 22

Percentage expression of AIF-1 mRNA expression compared to the PBS control

| Dose (μg) | Brain (1 mm section) | Cortex | Spinal cord (lumbar) | Spinal cord (cervical) |
|---|---|---|---|---|
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 23. The results indicate that treatment with increasing doses of ISIS 603538 did not have any significant changes in the body weights of the rats.

TABLE 23

Body weights of the rats (% initial body weight)

| | Dose (μg) | Week 1 | Week 2 | Week 3 | Week 4 | Week 5 |
|---|---|---|---|---|---|---|
| PBS | | 100 | 94 | 103 | 105 | 109 |
| ISIS 603538 | 700 | 100 | 94 | 98 | 103 | 107 |
| | 1000 | 100 | 95 | 97 | 101 | 103 |
| | 3000 | 100 | 92 | 98 | 102 | 105 |

Example 6

Preferential Inhibition of Human C9ORF72 Expression in Two Patient Fibroblast Lines Two different fibroblast cell lines from human patients (F09-152 and F09-229) were analyzed with antisense oligonucleotides that target the C9ORF72 pre-mRNA sequence before exon 1B; i.e. antisense oligonucleotides that target the hexanucleotide repeat expansion containing transcript and antisense oligonucleotides that target downstream of exon 1. The target start and stop sites and the target regions with respect to SEQ ID NOs: 1 and 2 for each oligonucleotide are provided in Table 24. ISIS 577061 and ISIS 577065 target C9ORF72 upstream of exon 1B and just upstream of the hexanucleotide repeat. The rest of the ISIS oligonucleotides of Table 24 target C9ORF72 downstream of exon 1B and the hexanucleotide repeat.

TABLE 24

Target Start and Stop sites of ISIS oligonucleotides used in a dose response assay in C9ORF72 patient fibroblasts

| ISIS No | Target Start Site at SEQ ID NO: 1 | Target Start Site at SEQ ID NO: 2 | Target Region |
|---|---|---|---|
| 577061 | n/a | 1406 | Upstream of exon 1B |
| 577065 | n/a | 1446 | Upstream of exon 1B |
| 577083 | n/a | 3452 | Downstream of exon 1B |
| 576816 | 232 | 7990 | Exon 2 |
| 576974 | 3132 | 28251 | Exon 11 |

Cells were plated at a density of 20,000 cells per well and transfected using electroporation with 246.9 nM, 740.7 nM, 2,222.2 nM, 6,666.7 nM, and 20,000.0 nM concentrations of antisense oligonucleotide. After a treatment period of approximately 16 hours, RNA was isolated from the cells and C9ORF72 mRNA levels were measured by quantitative real-time PCR. Two primer probe sets were used: (1) human C9ORF72 primer probe set RTS3750, which measures total mRNA levels, and (2) RTS3905, which targets the hexanucleotide repeat expansion containing transcript, which measures only mRNA transcripts that contain the hexanucleotide repeat expansion. C9ORF72 mRNA levels were adjusted according to total RNA content, as measured by RIBOGREEN®. Results are presented as percent inhibition of C9ORF72, relative to untreated control cells.

As illustrated in Table 25, below, the two oligonucleotides that target upstream of exon 1B and, therefore, target mRNA transcripts containing the hexanucleotide repeat expansion (ISIS 577061 and ISIS 577065), do not inhibit total mRNA levels of C9ORF72 (as measured by RTS3750) as well as ISIS 576974, 576816, and 577083, which target downstream of exon 1B and, therefore, do not target the mRNA transcript containing the hexanucleotide repeat expansion. Expression levels of the C9ORF72 mRNA transcript containing the hexanucleotide repeat expansion are low (about 10% of the total C9ORF72 expression products), therefore, oligonucleotides targeting the mRNA transcript containing the hexanucleotide repeat expansion do not robustly inhibit total C9ORF72 mRNA (as measured by RTS3905), as suggested by Table 25 below. Thus, ISIS 577061 and ISIS 577065 preferentially inhibit expression of mRNA transcripts containing the hexanucleotide repeat expansion.

TABLE 25

Percent inhibition of C9ORF72 total mRNA in F09-152 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 6 | 11 | 0 | 18 | 10 |
| 577065 | 10 | 11 | 30 | 29 | 0 |
| 576974 | 61 | 69 | 72 | 83 | 83 |
| 576816 | 35 | 76 | 82 | 91 | 93 |
| 577083 | 28 | 38 | 52 | 75 | 80 |

TABLE 26

Percent inhibition of C9ORF72 mRNA transcripts containing the hexanucleotide repeat expansion in F09-152 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 4 | 28 | 58 | 81 | 87 |
| 577065 | 25 | 54 | 70 | 90 | 94 |
| 576974 | 57 | 77 | 81 | 93 | 92 |
| 576816 | 37 | 77 | 91 | 97 | 98 |
| 577083 | 37 | 53 | 74 | 93 | 94 |

TABLE 27

Percent inhibition of C9ORF72 total mRNA in F09-229 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 0 | 0 | 0 | 17 | 7 |
| 577065 | 8 | 17 | 17 | 16 | 3 |
| 576974 | 43 | 58 | 85 | 85 | 74 |
| 576816 | 45 | 70 | 85 | 81 | 89 |
| 577083 | 22 | 45 | 56 | 76 | 78 |

TABLE 28

Percent inhibition of C9ORF72 mRNA transcripts containing the hexanucleotide repeat expansion in F09-229 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 14 | 36 | 70 | 87 | 89 |
| 577065 | 26 | 48 | 92 | 91 | 98 |
| 576974 | 63 | 87 | 91 | 92 | 91 |
| 576816 | 62 | 81 | 96 | 98 | 100 |
| 577083 | 36 | 64 | 82 | 98 | 96 |

What is claimed is:

1. A compound comprising a modified oligonucleotide consisting of 12 to 30 linked nucleosides and having a nucleobase sequence comprising at least 8 contiguous nucleobases of SEQ ID NO: 300 or SEQ ID NO: 301, wherein the modified oligonucleotide comprises at least one modification selected from a modified sugar, a sugar surrogate, and a modified internucleoside linkage.

2. The compound of claim 1, wherein the nucleobase sequence of the modified oligonucleotide is 100% complementary to an equal length portion of a C9ORF72 nucleic acid.

3. The compound of claim 2, wherein the C9ORF72 nucleic acid has the nucleobase sequence of SEQ ID NO: 2.

4. The compound of claim 1, wherein the modified oligonucleotide is a single-stranded oligonucleotide.

5. The compound of claim 4, wherein the single-stranded modified oligonucleotide is a gapmer.

6. The compound of claim 1, wherein at least one internucleoside linkage of the modified oligonucleotide is a modified internucleoside linkage.

7. The compound of claim 6, wherein each internucleoside linkage of the modified oligonucleotide is a modified internucleoside linkage.

8. The compound of claims 6, wherein the modified internucleoside linkage is a phosphorothioate internucleoside linkage.

9. The compound of claim 7, wherein the modified internucleoside linkage is a phosphorothioate internucleoside linkage.

10. The compound of claim 1, wherein at least one nucleobase of the modified oligonucleotide is a modified nucleobase.

11. The compound of claim 10, wherein the modified nucleobase is a 5-methylcytosine.

12. The compound of claim 1, wherein at least one nucleoside of the modified oligonucleotide comprises a modified sugar.

13. The compound of claim 12, wherein each nucleoside of the modified oligonucleotide comprises a modified sugar.

14. The compound of claim 12, wherein at least one modified sugar is a bicyclic sugar.

15. The compound of claim 14, wherein each bicyclic sugar comprises a chemical bridge between the 4' and 2' positions of the sugar, wherein each chemical bridge is independently selected from: 4'-CH(R)—O-2' and 4'-(CH$_2$)$_2$—O-2', wherein each R is independently selected from H, C$_1$-C$_6$ alkyl, and C$_1$-C$_6$ alkoxy.

16. The compound of claim 15, wherein at least one chemical bridge is 4'-CH(R)—O-2' and wherein R is methyl.

17. The compound of claim 15, wherein at least one chemical bridge is 4'-CH(R)—O-2' and wherein R is H.

18. The compound of claim 15, wherein at least one chemical bridge is 4'-CH(R)—O-2' and wherein R is —CH$_2$—O—CH$_3$.

19. The compound of claim 12, wherein at least one modified sugar comprises a 2'-O-methoxyethyl group.

20. The compound of claim 12, wherein at least one modified sugar comprises a 2'-O-methyl group.

21. The compound of claim 1, wherein the compound comprises a conjugate group.

22. A composition comprising a compound according to claim 1 and a pharmaceutically acceptable carrier or diluent.

23. The compound of claim 13, wherein each modified sugar comprises a 2'-O-methoxyethyl group or a 2'-O-methyl group.

24. The compound of claim 1, wherein the at least one nucleoside of the modified oligonucleotide comprises a sugar surrogate.

25. The compound of claim 24, wherein at least one sugar surrogate is a morpholino or a peptide nucleic acid.

26. A double-stranded compound comprising the compound of claim 1.

27. The double-stranded compound of claim 26, wherein the double-stranded compound comprises a conjugate group.

28. A modified oligonucleotide consisting of 12 to 30 linked nucleosides and having a nucleobase sequence comprising at least 8 contiguous nucleobases of SEQ ID NO: 300 or SEQ ID NO: 301,
wherein the modified oligonucleotide comprises at least one modification selected from a modified sugar, a sugar surrogate, and a modified internucleoside linkage.

29. The modified oligonucleotide of claim 28, wherein the nucleobase sequence of the oligonucleotide is 100% complementary to an equal length portion of a C9ORF72 nucleic acid.

30. The modified oligonucleotide of claim 29, wherein the C9ORF72 nucleic acid has the nucleobase sequence of SEQ ID NO: 2.

31. The modified oligonucleotide of claim 28, wherein at least one internucleoside linkage of the modified oligonucleotide is a modified internucleoside linkage.

32. The modified oligonucleotide of claim 28, wherein each internucleoside linkage of the modified oligonucleotide is a modified internucleoside linkage.

33. The modified oligonucleotide of claims 31, wherein the modified internucleoside linkage is a phosphorothioate internucleoside linkage.

34. The modified oligonucleotide of claim 32, wherein the modified internucleoside linkage is a phosphorothioate internucleoside linkage.

35. The modified oligonucleotide of claim 28, wherein at least one modified sugar is a bicyclic sugar.

36. The modified oligonucleotide of claim 35, wherein each bicyclic sugar comprises a chemical bridge between the 4' and 2' positions of the sugar, wherein each chemical bridge is independently selected from: 4'-CH(R)—O-2' and 4'-(CH$_2$)$_2$—O-2', wherein each R is independently selected from H, C$_1$-C$_6$ alkyl, and C$_1$-C$_6$ alkoxy.

37. The modified oligonucleotide of claim 36, wherein at least one chemical bridge is 4'-CH(R)—O-2' and wherein R is methyl.

38. The modified oligonucleotide of claim 36, wherein at least one chemical bridge is 4'-CH(R)—O-2' and wherein R is H.

39. The modified oligonucleotide of claim 36, wherein at least one chemical bridge is 4'-CH(R)—O-2' and wherein R is —CH$_2$—O—CH$_3$.

40. The modified oligonucleotide of claims 28, wherein at least one modified sugar comprises a 2'-O-methoxyethyl group.

41. The modified oligonucleotide of claim 28, wherein at least one modified sugar comprises a 2'-O-methyl group.

42. A composition comprising a modified oligonucleotide according to claim 28 and a pharmaceutically acceptable carrier or diluent.

43. A compound comprising a modified oligonucleotide consisting of 12 to 30 linked nucleosides and having a nucleobase sequence comprising at least 8 contiguous nucleobases that are 100% complementary to an equal length portion of nucleobases 1552-1572 of SEQ ID NO: 2, wherein the nucleobase sequence of the modified oligonucleotide is at least 90% complementary to an equal length portion of SEQ ID NO: 2, and wherein the modified oligonucleotide comprises at least one modification selected from a modified sugar, a sugar surrogate, and a modified internucleoside linkage.

44. The compound of claim 43, wherein the nucleobase sequence of the modified oligonucleotide is 100% complementary to an equal length portion of SEQ ID NO: 2.

45. The compound of claim 44, wherein the modified oligonucleotide is a single-stranded oligonucleotide.

46. The compound of claim 45, wherein at least one internucleoside linkage is a modified internucleoside linkage.

47. The compound of claim 46, wherein the modified internucleoside linkage is a phosphorothioate internucleoside linkage.

48. The compound of claim 46, wherein each internucleoside linkage of the single-stranded modified oligonucleotide is a phosphorothioate internucleoside linkage or a phosphodiester internucleoside linkage.

49. The compound of claim 45, wherein at least one nucleoside of the single-stranded modified oligonucleotide comprises a modified sugar.

50. The compound of claim 49, wherein at least one modified sugar comprises a 2'-O-methyl group.

51. The compound of claim 49, wherein at least one modified sugar comprises a 2'-O-methyoxyethyl group.

52. The compound of claim 49, wherein at least one modified sugar comprises a 2'-O-methyl group and at least one modified sugar comprises a 2'-O-methoxyethyl group.

53. The compound of claim 45, wherein the single-stranded modified oligonucleotide is a gapmer.

54. The compound of claim 53, wherein the gapmer is a 5-10-5 gapmer.

55. The compound of claim 54, wherein each nucleoside of the 5' wing and each nucleoside of the 3' wing of the gapmer comprises a modified sugar.

56. The compound of claim 55, wherein each modified sugar comprises a 2'-O-methyl group or a 2'-O-methyoxyethyl group.

57. The compound of claim 43, wherein the compound comprises a conjugate group.

58. A modified oligonucleotide consisting of 12 to 30 linked nucleosides and having a nucleobase sequence comprising at least 8 contiguous nucleobases that are 100% complementary to an equal length portion of nucleobases 1552-1572 of SEQ ID NO: 2, wherein the nucleobase sequence of the modified oligonucleotide is at least 90% complementary to an equal length portion of SEQ ID NO: 2, and wherein the modified oligonucleotide comprises at least one modification selected from a modified sugar, a sugar surrogate, and a modified internucleoside linkage.

59. The modified oligonucleotide of claim 58, wherein the nucleobase sequence of the modified oligonucleotide is 100% complementary to an equal length portion of SEQ ID NO: 2.

60. The compound of claim 59, wherein the modified oligonucleotide is a single-stranded oligonucleotide.

61. The compound of claim 60, wherein at least one internucleoside linkage is a modified internucleoside linkage.

62. The compound of claim 61, wherein the modified internucleoside linkage is a phosphorothioate internucleoside linkage.

63. The compound of claim 61, wherein each internucleoside linkage of the modified oligonucleotide is a phosphorothioate internucleoside linkage or a phosphodiester internucleoside linkage.

64. The compound of claim 60, wherein at least one nucleoside of the single-stranded oligonucleotide comprises a modified sugar.

65. The compound of claim 64, wherein at least one modified sugar comprises a 2'-O-methyl group.

66. The compound of claim 64, wherein at least one modified sugar comprises a 2'-O-methyoxyethyl group.

67. The compound of claim 64, wherein at least one modified sugar comprises a 2'-O-methyl group and at least one modified sugar comprises a 2'-O-methoxyethyl group.

68. The modified oligonucleotide of claim 60, wherein the single-stranded modified oligonucleotide is a gapmer.

69. The compound of claim 68, wherein the gapmer is a 5-10-5 gapmer.

70. The compound of claim 69, wherein each nucleoside of the 5' wing and each nucleoside of the 3' wing of the gapmer comprises a modified sugar.

71. The compound of claim 70, wherein each modified sugar comprises a 2'-O-methyl group or a 2'-O-methyoxyethyl group.

72. A compound comprising a single-stranded modified oligonucleotide consisting of 20 linked nucleosides and having a nucleobase sequence comprising at least 8 contiguous nucleobases of SEQ ID NO: 300 or SEQ ID NO: 301, wherein the nucleobase sequence of the modified oligonucleotide is 100% complementary to an equal length portion of SEQ ID NO: 2, wherein each internucleoside linkage is a phosphorothioate internucleoside linkage or a phosphodiester internucleoside linkage, wherein the single-stranded modified oligonucleotide is a 5-10-5 gapmer, wherein each nucleoside of the 5' wing and each nucleoside of the 3' wing comprises a modified sugar; and wherein each modified sugar comprises a 2'-O-methyl group or a 2'-O-methyoxyethyl group.

73. The compound of claim 72, wherein the modified oligonucleotide comprises at least 9 contiguous nucleobases of SEQ ID NO: 300.

74. The compound of claim 72, wherein the modified oligonucleotide comprises at least 10 contiguous nucleobases of SEQ ID NO: 300.

75. The compound of claim 72, wherein the modified oligonucleotide comprises at least 9 contiguous nucleobases of SEQ ID NO: 301.

76. The compound of claim 72, wherein the modified oligonucleotide comprises at least 10 contiguous nucleobases of SEQ ID NO: 301.

77. The compound of claim 72, wherein the compound comprises a conjugate group.

78. A single-stranded modified oligonucleotide consisting of 20 linked nucleosides and having a nucleobase sequence comprising at least 8 contiguous nucleobases of SEQ ID NO: 300 or SEQ ID NO: 301, wherein the nucleobase sequence of the modified oligonucleotide is 100% complementary to an equal length portion of SEQ ID NO: 2, wherein each internucleoside linkage is a phosphorothioate internucleoside linkage or a phosphodiester internucleoside linkage, wherein the single-stranded modified oligonucleotide is a 5-10-5 gapmer, wherein each nucleoside of the 5' wing and each nucleoside of the 3' wing comprises a modified sugar; and wherein each modified sugar comprises a 2'-O-methyl group or a 2'-O-methyoxyethyl group.

79. The compound of claim 78, wherein the modified oligonucleotide comprises at least 9 contiguous nucleobases of SEQ ID NO: 300.

80. The compound of claim 78, wherein the modified oligonucleotide comprises at least 10 contiguous nucleobases of SEQ ID NO: 300.

81. The compound of claim 78, wherein the modified oligonucleotide comprises at least 9 contiguous nucleobases of SEQ ID NO: 301.

82. The compound of claim 78, wherein the modified oligonucleotide comprises at least 10 contiguous nucleobases of SEQ ID NO: 301.

* * * * *

SEQUENCE LISTING

<160> NUMBER OF SEQ ID NOS: 369

<210> SEQ ID NO 1
<211> LENGTH: 3339
<212> TYPE: DNA
<213> ORGANISM: Homo sapiens
<220> FEATURE:
<221> NAME/KEY: CDS
<222> LOCATION: (203)..(1648)

<400> SEQUENCE: 1

```
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata    180
atgtgacagt tggaatgcag tg atg tcg act ctt tgc cca ccg cca tct cca     232
                         Met Ser Thr Leu Cys Pro Pro Pro Ser Pro
                          1               5                  10 gct gtt gcc aag aca gag att gct tta agt ggc aaa tca cct tta tta     280
Ala Val Ala Lys Thr Glu Ile Ala Leu Ser Gly Lys Ser Pro Leu Leu
                15                  20                  25 gca gct act ttt gct tac tgg gac aat att ctt ggt cct aga gta agg     328
Ala Ala Thr Phe Ala Tyr Trp Asp Asn Ile Leu Gly Pro Arg Val Arg
         30                  35                  40 cac att tgg gct cca aag aca gaa cag gta ctt ctc agt gat gga gaa     376
His Ile Trp Ala Pro Lys Thr Glu Gln Val Leu Leu Ser Asp Gly Glu
     45                  50                  55 ata act ttt ctt gcc aac cac act cta aat gga gaa atc ctt cga aat     424
Ile Thr Phe Leu Ala Asn His Thr Leu Asn Gly Glu Ile Leu Arg Asn
 60                  65                  70 gca gag agt ggt gct ata gat gta aag ttt ttt gtc ttg tct gaa aag     472
Ala Glu Ser Gly Ala Ile Asp Val Lys Phe Phe Val Leu Ser Glu Lys
75                  80                  85                  90 gga gtg att att gtt tca tta atc ttt gat gga aac tgg aat ggg gat     520
Gly Val Ile Ile Val Ser Leu Ile Phe Asp Gly Asn Trp Asn Gly Asp
```

```
                          95                  100                 105
cgc agc aca tat gga cta tca att ata ctt cca cag aca gaa ctt agt    568
Arg Ser Thr Tyr Gly Leu Ser Ile Ile Leu Pro Gln Thr Glu Leu Ser
            110                 115                 120 ttc tac ctc cca ctt cat aga gtg tgt gtt gat aga tta aca cat ata    616
Phe Tyr Leu Pro Leu His Arg Val Cys Val Asp Arg Leu Thr His Ile
        125                 130                 135 atc cgg aaa gga aga ata tgg atg cat aag gaa aga caa gaa aat gtc    664
Ile Arg Lys Gly Arg Ile Trp Met His Lys Glu Arg Gln Glu Asn Val
    140                 145                 150 cag aag att atc tta gaa ggc aca gag aga atg gaa gat cag ggt cag    712
Gln Lys Ile Ile Leu Glu Gly Thr Glu Arg Met Glu Asp Gln Gly Gln
155                 160                 165                 170 agt att att cca atg ctt act gga gaa gtg att cct gta atg gaa ctg    760
Ser Ile Ile Pro Met Leu Thr Gly Glu Val Ile Pro Val Met Glu Leu
            175                 180                 185 ctt tca tct atg aaa tca cac agt gtt cct gaa gaa ata gat ata gct    808
Leu Ser Ser Met Lys Ser His Ser Val Pro Glu Glu Ile Asp Ile Ala
        190                 195                 200 gat aca gta ctc aat gat gat gat att ggt gac agc tgt cat gaa ggc    856
Asp Thr Val Leu Asn Asp Asp Asp Ile Gly Asp Ser Cys His Glu Gly
    205                 210                 215 ttt ctt ctc aat gcc atc agc tca cac ttg caa acc tgt ggc tgt tcc    904
Phe Leu Leu Asn Ala Ile Ser Ser His Leu Gln Thr Cys Gly Cys Ser
220                 225                 230 gtt gta gta ggt agc agt gca gag aaa gta aat aag ata gtc aga aca    952
Val Val Val Gly Ser Ser Ala Glu Lys Val Asn Lys Ile Val Arg Thr
235                 240                 245                 250 tta tgc ctt ttt ctg act cca gca gag aga aaa tgc tcc agg tta tgt   1000
Leu Cys Leu Phe Leu Thr Pro Ala Glu Arg Lys Cys Ser Arg Leu Cys
            255                 260                 265 gaa gca gaa tca tca ttt aaa tat gag tca ggg ctc ttt gta caa ggc   1048
Glu Ala Glu Ser Ser Phe Lys Tyr Glu Ser Gly Leu Phe Val Gln Gly
        270                 275                 280 ctg cta aag gat tca act gga agc ttt gtg ctg cct ttc cgg caa gtc   1096
Leu Leu Lys Asp Ser Thr Gly Ser Phe Val Leu Pro Phe Arg Gln Val
    285                 290                 295 atg tat gct cca tat ccc acc aca cac ata gat gtg gat gtc aat act   1144
Met Tyr Ala Pro Tyr Pro Thr Thr His Ile Asp Val Asp Val Asn Thr
300                 305                 310 gtg aag cag atg cca ccc tgt cat gaa cat att tat aat cag cgt aga   1192
Val Lys Gln Met Pro Pro Cys His Glu His Ile Tyr Asn Gln Arg Arg
315                 320                 325                 330 tac atg aga tcc gag ctg aca gcc ttc tgg aga gcc act tca gaa gaa   1240
Tyr Met Arg Ser Glu Leu Thr Ala Phe Trp Arg Ala Thr Ser Glu Glu
            335                 340                 345 gac atg gct cag gat acg atc atc tac act gac gaa agc ttt act cct   1288
Asp Met Ala Gln Asp Thr Ile Ile Tyr Thr Asp Glu Ser Phe Thr Pro
        350                 355                 360 gat ttg aat att ttt caa gat gtc tta cac aga gac act cta gtg aaa   1336
Asp Leu Asn Ile Phe Gln Asp Val Leu His Arg Asp Thr Leu Val Lys
    365                 370                 375 gcc ttc ctg gat cag gtc ttt cag ctg aaa cct ggc tta tct ctc aga   1384
Ala Phe Leu Asp Gln Val Phe Gln Leu Lys Pro Gly Leu Ser Leu Arg
380                 385                 390 agt act ttc ctt gca cag ttt cta ctt gtc ctt cac aga aaa gcc ttg   1432
Ser Thr Phe Leu Ala Gln Phe Leu Leu Val Leu His Arg Lys Ala Leu
395                 400                 405                 410 aca cta ata aaa tat ata gaa gac gat acg cag aag gga aaa aag ccc   1480
```

```
               Thr Leu Ile Lys Tyr Ile Glu Asp Asp Thr Gln Lys Gly Lys Lys Pro
                               415                 420                 425 ttt aaa tct ctt cgg aac ctg aag ata gac ctt gat tta aca gca gag         1528
Phe Lys Ser Leu Arg Asn Leu Lys Ile Asp Leu Asp Leu Thr Ala Glu
                430                 435                 440 ggc gat ctt aac ata ata atg gct ctg gct gag aaa att aaa cca ggc         1576
Gly Asp Leu Asn Ile Ile Met Ala Leu Ala Glu Lys Ile Lys Pro Gly
                445                 450                 455 cta cac tct ttt atc ttt gga aga cct ttc tac act agt gtg caa gaa         1624
Leu His Ser Phe Ile Phe Gly Arg Pro Phe Tyr Thr Ser Val Gln Glu
                460                 465                 470 cga gat gtt cta atg act ttt taa atgtgtaact taataagcct attccatcac        1678
Arg Asp Val Leu Met Thr Phe
475                 480 aatcatgatc gctggtaaag tagctcagtg gtgtggggaa acgttcccct ggatcatact       1738
ccagaattct gctctcagca attgcagtta agtaagttac actacagttc tcacaagagc       1798
ctgtgagggg atgtcaggtg catcattaca ttgggtgtct cttttcctag atttatgctt       1858
ttgggataca gacctatgtt tacaatataa taaatattat tgctatcttt taaagatata       1918
ataataggat gtaaacttga ccacaactac tgttttttg aaatacatga ttcatggttt        1978
acatgtgtca aggtgaaatc tgagttggct tttacagata gttgactttc tatcttttgg       2038
cattctttgg tgtgtagaat tactgtaata cttctgcaat caactgaaaa ctagagcctt       2098
taaatgattt caattccaca gaaagaaagt gagcttgaac ataggatgag ctttagaaag       2158
aaaattgatc aagcagatgt ttaattggaa ttgattatta gatcctactt tgtggattta      2218
gtccctggga ttcagtctgt agaaatgtct aatagttctc tatagtcctt gttcctggtg       2278
aaccacagtt agggtgtttt gtttatttta ttgttcttgc tattgttgat attctatgta       2338
gttgagctct gtaaaggaa attgtatttt atgttttagt aattgttgcc aacttttaa         2398 attaattttc attattttg agccaaattg aaatgtgcac ctcctgtgcc ttttttctcc        2458
ttagaaaatc taattacttg gaacaagttc agatttcact ggtcagtcat tttcatcttg       2518
ttttcttctt gctaagtctt accatgtacc tgctttggca atcattgcaa ctctgagatt       2578
ataaaatgcc ttagagaata tactaactaa taagatcttt ttttcagaaa cagaaaatag       2638
ttccttgagt acttccttct tgcatttctg cctatgtttt tgaagttgtt gctgtttgcc       2698
tgcaataggc tataaggaat agcaggagaa attttactga agtgctgttt tcctaggtgc       2758
tactttggca gagctaagtt atcttttgtt ttcttaatgc gtttggacca ttttgctggc       2818
tataaaataa ctgattaata taattctaac acaatgttga cattgtagtt acacaaacac       2878
aaataaatat tttatttaaa attctggaag taatataaaa gggaaaatat atttataaga       2938
aagggataaa ggtaatagag cccttctgcc ccccacccac caaatttaca caacaaaatg       2998
acatgttcga atgtgaaagg tcataatagc tttcccatca tgaatcagaa agatgtggac       3058
agcttgatgt tttagacaac cactgaacta gatgactgtt gtactgtagc tcagtcattt       3118
aaaaaatata taaatactac cttgtagtgt cccatactgt gttttttaca tggtagattc       3178
ttatttaagt gctaactggt tattttcttt ggctggttta ttgtactgtt atacagaatg       3238
taagttgtac agtgaaataa gttattaaag catgtgtaaa cattgttata tatcttttct       3298
cctaaatgga gaattttgaa taaatatat ttgaaatttt g                            3339
```

<210> SEQ ID NO 2
<211> LENGTH: 30001
<212> TYPE: DNA

<213> ORGANISM: Homo sapiens

<400> SEQUENCE: 2

| | | | | | |
|---|---|---|---|---|---|
| caaagaaaag | ggggaggttt | tgttaaaaaa | gagaaatgtt | acatagtgct | ctttgagaaa | 60
| attcattggc | actattaagg | atctgaggag | ctggtgagtt | tcaactggtg | agtgatggtg | 120
| gtagataaaa | ttagagctgc | agcaggtcat | tttagcaact | attagataaa | actggtctca | 180
| ggtcacaacg | ggcagttgca | gcagctggac | ttggagagaa | ttacactgtg | ggagcagtgt | 240
| catttgtcct | aagtgctttt | ctaccccta | ccccactat | tttagttggg | tataaaaga | 300
| atgacccaat | ttgtatgatc | aactttcaca | aagcatagaa | cagtaggaaa | agggtctgtt | 360
| tctgcagaag | gtgtagacgt | tgagagccat | tttgtgtatt | tattcctccc | tttcttcctc | 420
| ggtgaatgat | taaacgttc | tgtgtgattt | ttagtgatga | aaagattaa | atgctactca | 480
| ctgtagtaag | tgccatctca | cacttgcaga | tcaaaggca | cacagtttaa | aaaacctttg | 540
| tttttttaca | catctgagtg | gtgtaaatgc | tactcatctg | tagtaagtgg | aatctataca | 600
| cctgcagacc | aaaagacgca | aggtttcaaa | aatctttgtg | ttttttacac | atcaaacaga | 660
| atggtacgtt | tttcaaaagt | taaaaaaaaa | caactcatcc | acatattgca | actagcaaaa | 720
| atgacattcc | ccagtgtgaa | aatcatgctt | gagagaattc | ttacatgtaa | aggcaaaatt | 780
| gcgatgactt | tgcaggggac | cgtgggattc | ccgcccgcag | tgccggagct | gtcccctacc | 840
| agggtttgca | gtggagtttt | gaatgcactt | aacagtgtct | tacggtaaaa | acaaaatttc | 900
| atccaccaat | tatgtgttga | gcgcccactg | cctaccaagc | acaaacaaaa | ccattcaaaa | 960
| ccacgaaatc | gtcttcactt | tctccagatc | cagcagcctc | ccctattaag | gttcgcacac | 1020
| gctattgcgc | caacgctcct | ccagagcggg | tcttaagata | aagaacagg | acaagttgcc | 1080
| ccgcccatt | tcgctagcct | cgtgagaaaa | cgtcatcgca | catagaaaac | agacagacgt | 1140
| aacctacggt | gtcccgctag | gaaagagagg | tgcgtcaaac | agcgacaagt | tccgcccacg | 1200
| taaaagatga | cgcttggtgt | gtcagccgtc | cctgctgccc | ggttgcttct | cttttgggg | 1260
| cggggtctag | caagagcagg | tgtgggttta | ggaggtgtgt | gttttgttt | tcccacccct | 1320
| ctctccccac | tacttgctct | cacagtactc | gctgagggtg | aacaagaaaa | gacctgataa | 1380
| agattaacca | gaagaaaaca | aggagggaaa | caaccgcagc | ctgtagcaag | ctctggaact | 1440
| caggagtcgc | gcgctagggg | ccgggccgg | ggccggggcg | tggtcgggc | gggcccgggg | 1500
| gcgggcccgg | ggcggggctg | cggttgcggt | gcctgcgccc | gcggcggcgg | aggcgcaggc | 1560
| ggtggcgagt | gggtgagtga | ggaggcggca | tcctggcggg | tggctgtttg | gggttcggct | 1620
| gccgggaaga | ggcgcgggta | gaagcggggg | ctctcctcag | agctcgacgc | attttttactt | 1680
| tccctctcat | ttctctgacc | gaagctgggt | gtcgggcttt | cgcctctagc | gactggtgga | 1740
| attgcctgca | tccgggcccc | gggcttccg | gcggcggcg | cggcggcggc | ggcgcaggga | 1800
| caagggatgg | ggatctggcc | tcttccttgc | tttcccgccc | tcagtacccg | agctgtctcc | 1860
| ttcccgggga | cccgctggga | gcgctgccgc | tgcgggctcg | agaaagggga | gcctcgggta | 1920
| ctgagaggcc | tcgcctgggg | gaaggccgga | gggtgggcgg | cgcgcggctt | ctgcggacca | 1980
| agtcgggtt | cgctaggaac | ccgagacggt | ccctgccggc | gaggagatca | tgcgggatga | 2040
| gatggggtg | tggagacgcc | tgcacaattt | cagcccaagc | ttctagagag | tggtgatgac | 2100
| ttgcatatga | gggcagcaat | gcaagtcggt | gtgctcccca | ttctgtggga | catgacctgg | 2160
| ttgcttcaca | gctccgagat | gacacagact | tgcttaaagg | aagtgactat | tgtgacttgg | 2220
| gcatcacttg | actgatggta | atcagttgtc | taaagaagtg | cacagattac | atgtccgtgt | 2280

```
gctcattggg tctatctggc cgcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tataggggat attaataacc    2640
tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctcttttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat ttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga tttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tctttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg ctaattttt tgtatttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc attttttttt tcttattctg    4440
ttaggagtga gagtgtaact agcagtataa tagttcaatt ttcacaacgt ggtaaaagtt    4500
tccctataat tcaatcagat tttgctccag ggttcagttc tgttttagga aatacttta    4560 ttttcagttt aatgatgaaa tattagagtt gtaatattgc ctttatgatt atccaccttt    4620
```

```
ttaacctaaa agaatgaaag aaaaatatgt ttgcaatata atttatggt tgtatgttaa    4680 cttaattcat tatgttggcc tccagtttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttgaa     4920 attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgcttttccat cagactgaac tctcttgaca agatgtggat   5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatagtac aatcacacat tgcttaggaa    5340
tgcatcatta ggcgattttg tcattatgca aacatcatag agtgtactta cacaaaccta    5400
gatagtatag cctttatgta cctaggccgt atggtatagt ctgttgctcc taggccacaa    5460
acctgtacaa ctgttactgt actgaatact atagacagtg gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac tttttaactt tgtaaacttt taatttttt aacttttaaa atacttagct     5820
tgaaacacaa atacattgta tagctataca aaaatatttt ttctttgtat ccttattcta    5880
gaagcttttt tctatttct atttaaatt tttttttta cttgttagtc gttttgtta       5940 aaaactaaaa cacacacact ttcacctagg catagacagg attaggatca tcagtatcac    6000
tcccttccac ctcactgcct tccacctcca catcttgtcc cactggaagg ttttagggg     6060 caataacaca catgtagctg tcacctatga taacagtgct ttctgttgaa tacctcctga    6120
aggacttgcc tgaggctgtt ttacatttaa cttaaaaaaa aaaaagtag aaggagtgca    6180 ctctaaaata acaataaaag gcatagtata gtgaatacat aaaccagcaa tgtagtagtt    6240
tattatcaag tgttgtacac tgtaataatt gtatgtgcta tactttaaat aacttgcaaa    6300
atagtactaa gaccttatga tggttacagt gtcactaagg caatagcata ttttcaggtc    6360
cattgtaatc taatgggact accatcatat atgcagtcta ccattgactg aaacgttaca    6420
tggcacataa ctgtatttgc aagaatgatt tgttttacat taatatcaca taggatgtac    6480 cttttagag tggtatgttt atgtggatta agatgtacaa gttgagcaag gggaccaaga    6540
gccctgggtt ctgtcttgga tgtgagcgtt tatgttcttc tcctcatgtc tgttttctca    6600
ttaaattcaa aggcttgaac gggccctatt tagcccttct gttttctacg tgttctaaat    6660
aactaaagct tttaaattct agccatttag tgtagaactc tctttgcagt gatgaaatgc    6720
tgtattggtt tctggctag catattaaat attttatct ttgtcttgat acttcaatgt     6780
cgttttaaac atcaggatcg ggcttcagta ttctcataac cagagagttc actgaggata    6840
caggactgtt tgcccatttt ttgttatggc tccagacttg tggtatttcc atgtcttttt    6900
tttttttttt tttttgacc ttttagcggc tttaaagtat ttctgttgtt aggtgttgta    6960
ttacttttct aagattactt aacaaagcac cacaaactga gtggctttaa acaacagcaa    7020
```

```
tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgaccccatt ttaacatgat tacacttatt    7320
tctagataag gtcacattca cgtacaccaa gggttaggaa ttgaacatat cttttggggg    7380
gacacaattc aacccacaag tgtcagtctc tagctgagcc tttcccttcc tgttttctc     7440 ctttttagtt gctatgggtt aggggccaaa tctccagtca tactagaatt gcacatggac    7500
tggatatttg gaatactgc gggtctattc tatgagcttt agtatgtaac atttaatatc     7560
agtgtaaaga agcccttttt taagttattt ctttgaattt ctaaatgtat gccctgaata    7620
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttggggtt ttgatggata tcttaaatt     7800 gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgattttc     8340 agcttattaa tcatgttaac ctatctgttg aaagcttatt ttctggtaca tataaatctt    8400
atttttttaa ttatatgcag tgaacatcaa acaataaatg ttatttattt tgcatttacc    8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata ccttttgttt cccttttcatt   8640 gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat tttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc ttttttgaaac tatgcagatg ttacattgac tgttttctgt    9180
gaagttatct ttttttcact gcagaataaa ggttgttttg attttatttt gtattgttta    9240
tgagaacatg catttgttgg gttaatttcc taccctgcc cccatttttt ccctaaagta     9300
gaaagtattt ttcttgtgaa ctaaattact acacaagaac atgtctattg aaaaataagc    9360
```

```
aagtatcaaa atgttgtggg ttgttttttt aaataaattt tctcttgctc aggaaagaca      9420
agaaaatgtc cagaagatta tcttagaagg cacagagaga atggaagatc aggtatatgc      9480
aaattgcata ctgtcaaatg tttttctcac agcatgtatc tgtataaggt tgatggctac      9540
atttgtcaag gccttggaga catacgaata agcctttaat ggagctttta tggaggtgta      9600
cagaataaac tggaggaaga tttccatatc ttaaacccaa agagttaaat cagtaaacaa      9660
aggaaaatag taattgcatc tacaaattaa tatttgctcc ctttttttt ctgtttgccc        9720
agaataaatt ttggataact tgttcatagt aaaaataaaa aaaattgtct ctgatatgtt      9780
ctttaaggta ctacttctcg aacctttccc tagaagtagc tgtaacagaa ggagagcata      9840
tgtaccctg aggtatctgt ctggggtgta ggcccaggtc cacacaatat ttcttctaag        9900
tcttatgttg tatcgttaag actcatgcaa tttacatttt attccataac tattttagta      9960
ttaaatttg tcagtgatat ttcttaccct ctcctctagg aaaatgtgcc atgtttatcc       10020
cttggctttg aatgccctc aggaacagac actaagagtt tgagaagcat ggttacaagg      10080
gtgtggcttc cctgcggaa actaagtaca gactatttca ctgtaaagca gagaagttct      10140
tttgaaggag aatctccagt gaagaaagag ttcttcactt ttacttccat ttcctcttgt     10200
gggtgaccct caatgctcct tgtaaaactc caatatttta aacatggctg ttttgccttt     10260
ctttgcttct ttttagcatg aatgagacag atgatacttt aaaaaagtaa ttaaaaaaaa      10320
aaacttgtga aaatacatgg ccataataca gaacccaata caatgatctc ctttaccaaa      10380
ttgttatgtt tgtacttttg tagatagctt tccaattcag agacagttat tctgtgtaaa      10440
ggtctgactt aacaagaaaa gatttccctt tacccaaaga atcccagtcc ttatttgctg      10500
gtcaataagc agggtcccca ggaatggggt aactttcagc accctctaac ccactagtta     10560
ttagtagact aattaagtaa acttatcgca agttgaggaa acttagaacc aactaaaatt     10620
ctgcttttac tgggattttg tttttttcaaa ccagaaacct ttacttaagt tgactactat    10680
taatgaattt tggtctctct tttaagtgct cttcttaaaa atgttatctt actgctgaga     10740
agttcaagtt tgggaagtac aaggaggaat agaaacttaa gagattttct tttagagcct     10800
cttctgtatt tagccctgta ggattttttt tttttttt tttttggtg ttgttgagct         10860
tcagtgaggc tattcattca cttatactga taatgtctga gatactgtga atgaaatact     10920
atgtatgctc aaacctaaga ggaaatattt tcccaaaatt attcttcccg aaaaggagga     10980
gttgcctttt gattgagttc ttgcaaatct cacaacgact ttattttgaa caatactgtt     11040
tgggatgat gcattagttt gaaacaactt cagttgtagc tgtcatctga taaaattgct      11100
tcacagggaa ggaaatttaa cacggatcta gtcattattc ttgttagatt gaatgtgtga     11160
attgtaattg taaacaggca tgataattat tacttttaaaa actaaaaaca gtgaatagtt    11220
agttgtggag gttactaaag gatggttttt ttttaaataa aactttcagc attatgcaaa     11280
tgggcatatg gcttaggata aaacttccag aagtagcatc acatttaaat tctcaagcaa     11340
cttaataata tggggctctg aaaaactggt taaggttact ccaaaaatgg ccctgggtct     11400
gacaaagatt ctaacttaaa gatgcttatg aagactttga gtaaaatcat ttcataaaat     11460
aagtgaggaa aaacaactag tattaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc     11640
catatttgag acacttttaca tttgtgatgt gttatactga attttcagtt tgattctata   11700
gactacaaat ttcaaaatta caatttcaag atgtaataag tagtaatatc ttgaaatagc    11760
```

```
tctaaaggga attttttctgt tttattgatt cttaaaatat atgtgctgat tttgatttgc    11820
atttgggtag attatacttt tatgagtatg gaggttaggt attgattcaa gttttccttca   11880 cctatttggt aaggatttca aagtcttttt gtgcttggtt ttcctcattt ttaaatatga    11940
aatatattga tgacctttaa caaattttt ttatctcaaa ttttaaagga gatcttttct     12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaaagaaa agaaagaata aaagtgagct ttggattgca    12360
tataaatcct ttagacatgt agtagacttg tttgatactg tgtttgaaca aattacgaag    12420
tattttcatc aaagaatgtt attgtttgat gttatttta ttttttattg cccagcttct     12480
ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660
ttttggggtt atagtattat tatgtatatt attaatattc taattttaat agtaaggact    12720
ttgtcataca tactattcac atacagtatt agccacttta gcaataagc acacacaaaa     12780 tcctggatt tatggcaaaa cagaggcatt tttgatcagt gatgacaaaa ttaaattcat     12840
tttgtttatt tcattacttt tataattcct aaaagtggga ggatcccagc tcttatagga    12900
gcaattaata tttaatgtag tgtcttttga acaaaactg tgtgccaaag tagtaaccat     12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
gcacagagat tgttttttgg ggagtcttga ttctcggaaa tgaaggcagt gtgttatatt    13260
gaatccagac ttccgaaaac ttgtatatta aaagtgttat ttcaacacta tgttacagcc    13320
agactaattt ttttattttt tgatgcattt tagatagctg atacagtact caatgatgat    13380
gatattggtg acagctgtca tgaaggcttt cttctcaagt aagaattttt cttttcataa    13440
aagctggatg aagcagatac catcttatgc tcacctatga caagatttgg aagaaagaaa    13500
ataacagact gtctacttag attgttctag ggacattacg tatttgaact gttgcttaaa    13560
tttgtgttat ttttcactca ttatatttct atatatattt ggtgttattc catttgctat    13620
ttaaagaaac cgagttttcca tcccagacaa gaaatcatgg ccccttgctt gattctggtt   13680
tcttgtttta cttctcatta aagctaacag aatcctttca tattaagttg tactgtagat    13740
gaacttaagt tatttaggcg tagaacaaaa ttattcatat ttatactgat ctttttccat    13800
ccagcagtgg agtttagtac ttaagagttt gtgcccttaa accagactcc ctggattaat    13860
gctgtgtacc cgtgggcaag gtgcctgaat tctctataca cctatttcct catctgtaaa    13920
atggcaataa tagtaatagt acctaatgtg tagggttgtt ataagcattg agtaagataa    13980
ataatataaa gcacttagaa cagtgcctgg aacataaaaa cacttaataa tagctctag    14040 ctaacatttc ctatttacat ttcttctaga aatagccagt atttgttgag tgcctacatg    14100
```

```
ttagttcctt tactagttgc tttacatgta ttatcttata ttctgtttta aagtttcttc    14160
acagttacag attttcatga aattttactt ttaataaaag agaagtaaaa gtataaagta    14220
ttcactttta tgttcacagt cttttccttt aggctcatga tggagtatca gaggcatgag    14280
tgtgtttaac ctaagagcct taatggcttg aatcagaagc actttagtcc tgtatctgtt    14340
cagtgtcagc ctttcataca tcattttaaa tcccatttga ctttaagtaa gtcacttaat    14400
ctctctacat gtcaatttct tcagctataa aatgatggta tttcaataaa taaatacatt    14460
aattaaatga tattatactg actaattggg ctgttttaag gctcaataag aaaatttctg    14520
tgaaaggtct ctagaaaatg taggttccta tacaaataaa agataacatt gtgcttatag    14580
cttcggtgtt tatcatataa agctattctg agttatttga agagctcacc tacttttttt    14640 tgttttagt ttgttaaatt gttttatagg caatgttttt aatctgtttt ctttaactta    14700
cagtgccatc agctcacact tgcaaacctg tggctgttcc gttgtagtag gtagcagtgc    14760
agagaaagta aataaggtag tttattttat aatctagcaa atgatttgac tctttaagac    14820
tgatgatata tcatggattg tcatttaaat ggtaggttgc aattaaaatg atctagtagt    14880
ataaggaggc aatgtaatct catcaaattg ctaagacacc ttgtggcaac agtgagtttg    14940 aaataaaactg agtaagaatc atttatcagt ttattttgat agctcggaaa taccagtgtc    15000
agtagtgtat aaatggtttt gagaatatat taaaatcaga tatataaaaa aaattactct    15060
tctatttccc aatgttatct ttaacaaatc tgaagatagt catgtacttt tggtagtagt    15120
tccaaagaaa tgttatttgt ttattcatct tgatttcatt gtcttcgctt tccttctaaa    15180
tctgtccctt ctagggagct attgggatta agtggtcatt gattattata ctttattcag    15240
taatgtttct gacccttttcc ttcagtgcta cttgagttaa ttaaggatta atgaacagtt    15300
acatttccaa gcattagcta ataaactaaa ggattttgca cttttcttca ctgaccatta    15360
gttagaaaga gttcagagat aagtatgtgt atctttcaat ttcagcaaac ctaattttt    15420 aaaaaaagtt ttacatagga aatatgttgg aaatgatact ttacaaagat attcataatt    15480
tttttttgta atcagctact ttgtatattt acatgagcct taatttatat ttctcatata    15540
accatttatg agagcttagt atacctgtgt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt ttttaaacat ttttcccatc ctccatcctc ttgagggaga atagcttacc    15780
ttttatcttg ttttaatttg agaaagaagt tgccaccact ctaggttgaa aaccactcct    15840
ttaacataat aactgtggat atggtttgaa tttcaagata gttacatgcc tttttatttt    15900
tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtctttttac ttcatgtttt aatgctaaaa    16380
tattttcttt tatagatagt cagaacatta tgccttttc tgactccagc agagagaaaa    16440
tgctccaggt tatgtgaagc agaatcatca tttaaatatg agtcagggct ctttgtacaa    16500
```

```
ggcctgctaa aggtatagtt tctagttatc acaagtgaaa ccactttct aaaatcattt      16560 ttgagactct ttatagacaa atcttaaata ttagcattta atgtatctca tattgacatg      16620
cccagagact gacttccttt acacagttct gcacatagac tatatgtctt atggatttat      16680
agttagtatc atcagtgaaa caccatagaa tacccttgt gttccaggtg ggtccctgtt       16740
cctacatgtc tagcctcagg acttttttt ttttaacaca tgcttaaatc aggttgcaca      16800
tcaaaaataa gatcatttct ttttaactaa atagatttga atttattga aaaaaaattt      16860 taaacatctt taagaagctt ataggattta agcaattcct atgtatgtgt actaaaatat     16920
atatatttct atatataata tatattagaa aaaaattgta tttttcttt atttgagtct      16980 actgtcaagg agcaaaacag agaaatgtaa attagcaatt atttataata cttaaaggga     17040
agaaagttgt tcaccttgtt gaatctatta ttgttatttc aattatagtc ccaagacgtg     17100
aagaaatagc tttcctaatg gttatgtgat tgtctcatag tgactacttt cttgaggatg     17160
tagccacggc aaaatgaaat aaaaaatttt aaaaattgtt gcaaatacaa gttatattag     17220
gcttttgtgc attttcaata atgtgctgct atgaactcag aatgatagta tttaaatata     17280
gaaactagtt aaaggaaacg tagtttctat ttgagttata catatctgta aattagaact     17340
tctcctgtta aaggcataat aaagtgctta atacttttgt ttcctcagca ccctctcatt     17400
taattatata attttagttc tgaaagggac ctataccaga tgcctagagg aaatttcaaa     17460
actatgatct aatgaaaaaa tatttaatag ttctccatgc aaatacaaat catatagttt     17520
tccagaaaat accttttgaca ttatacaaag atgattatca cagcattata atagtaaaaa     17580
aatggaaata gcctctttct tctgttctgt tcatagcaca gtgcctcata cgcagtaggt     17640
tattattaca tggtaactgg ctaccccaac tgattaggaa agaagtaaat ttgttttata    17700
aaaatacata ctcattgagg tgcatagaat aattaagaaa ttaaaagaca cttgtaattt     17760
tgaatccagt gaatacccac tgttaatatt tggtatatct ctttctagtc ttttttccc     17820 ttttgcatgt attttcttta agactcccac ccccactgga tcatctctgc atgttctaat     17880
ctgctttttt cacagcagat tctaagcctc tttgaatatc aacacaaact tcaacaactt     17940
catctataga tgccaaataa taaattcatt tttatttact taaccacttc ctttggatgc     18000
ttaggtcatt ctgatgtttt gctattgaaa ccaatgctat actgaacact tctgtcacta     18060
aaactttgca cacactcatg aatagcttct taggataaat tttagagat ggatttgcta     18120 aatcagagac catttttaa aattaaaaaa caattattca tatcgtttgg catgtaagac      18180
agtaaatttt cctttattt tgacaggatt caactggaag ctttgtgctg cctttccggc      18240
aagtcatgta tgctccatat cccaccacac acatagatgt ggatgtcaat actgtgaagc     18300
agatgccacc ctgtcatgaa catatttata atcagcgtag atacatgaga tccgagctga     18360
cagccttctg gagagccact tcagaagaag acatggctca ggatacgatc atctacactg     18420
acgaaagctt tactcctgat ttgtacgtaa tgctctgcct gctggtactg tagtcaagca    18480
atatgaaatt gtgtcttta cgaataaaaa caaaacagaa gttgcattta aaagaaaga     18540 aatattacca gcagaattat gcttgaagaa acatttaatc aagcattttt ttcttaaatg    18600
ttcttctttt tccatacaat tgtgtttacc ctaaaatagg taagattaac ccttaaagta    18660
aatatttaac tatttgtttta ataaatatat attgagctcc taggcactgt tctaggtacc    18720
gggcttaata gtggccaacc agacagcccc agcccagcc cctacattgt gtatagtcta      18780
ttatgtaaca gttattgaat ggacttatta acaaaaccaa agaagtaatt ctaagtctttt    18840
```

```
tttttcttga catatgaata taaaatacag caaaactgtt aaaatatatt aatggaacat    18900 tttttttactt tgcattttat attgttattc acttcttatt tttttttaaa aaaaaaagcc    18960
tgaacagtaa attcaaaagg aaaagtaatg ataattaatt gttgagcatg gacccaactt    19020
gaaaaaaaaa atgatgatga taaatctata atcctaaaac cctaagtaaa cacttaaaag    19080
atgttctgaa atcaggaaaa gaattatagt atactttttgt gtttctcttt tatcagttga    19140
aaaaaggcac agtagctcat gcctgtaaga acagagcttt gggagtgcaa ggcaggcgga    19200
tcacttgagg ccaggagttc cagaccagcc tgggcaacat agtgaaaccc catctctaca    19260
aaaaataaaa aagaattatt ggaatgtgtt tctgtgtgcc tgtaatccta gctattccga    19320
aagctgaggc aggaggatct tttgagccca ggagtttgag gttacaggga gttatgatgt    19380
gccagtgtac tccagcctgg ggaacaccga gactctgtct tatttaaaaa aaaaaaaaaa    19440
aaaatgcttg caataatgcc tggcacatag aaggtaacag taagtgttaa ctgtaataac    19500
ccaggtctaa gtgtgtaagg caatagaaaa attggggcaa ataagcctga cctatgtatc    19560
tacagaatca gtttgagctt aggtaacaga cctgtggagc accagtaatt acacagtaag    19620
tgttaaccaa aagcatagaa taggaatatc ttgttcaagg gacccccagc cttatacatc    19680
tcaaggtgca gaaagatgac ttaatatagg acccatttttt tcctagttct ccagagtttt    19740
tattggttct tgagaaagta gtaggggaat gttttagaaa atgaattggt ccaactgaaa    19800
ttacatgtca gtaagttttt atatattggt aaatttttagt agacatgtag aagttttcta    19860
attaatctgt gccttgaaac attttctttt ttcctaaagt gcttagtatt ttttccgttt    19920
tttgattggt tacttgggag ctttttttgag gaaatttagt gaactgcaga atgggtttgc    19980
aaccatttgg tattttttgtt ttgttttttta gaggatgtat gtgtattttta acatttctta    20040 atcatttttta gccagctatg tttgttttgc tgatttgaca aactacagtt agacagctat    20100
tctcattttg ctgatcatga caaaataata tcctgaattt ttaaattttg catccagctc    20160 taaatttttct aaacataaaa ttgtccaaaa aatagtattt tcagccacta gattgtgtgt    20220
taagtctatt gtcacagagt cattttactt ttaagtatat gttttttacat gttaattatg    20280 tttgttattt ttaattttaa ctttttaaaa taattccagt cactgccaat acatgaaaaa    20340
ttggtcactg gaatttttttt tttgactttt attttaggtt catgtgtaca tgtgcaggtg    20400
tgttatacag gtaaattgcg tgtcatgagg gtttggtgta caggtgattt cattacccag    20460
gtaataagca tagtacccaa taggtagttt tttgatcctc acccttctcc cacccctcaag    20520 taggccctgg tgttgctgtt tccttctttg tgtccatgta tactcagtgt ttagctccca    20580
cttagaagtg agaacatgcg gtagttggtt ttctgttcct ggattagttc acttaggata    20640
atgacctcta gctccatctg gttttttatgg ctgcatagta ttccatggtg tatatgtatc    20700
acattttctt tatccagtct accattgata ggcatttagg ttgattccct gtctttgtta    20760
tcatgaatag tgctgtgatg aacatacaca tgcatgtgtc tttatggtag aaaaatttgt    20820 attccttttag gtacatatag aataatgggg ttgctagggt gaatggtagt tctattttca    20880
gttatttgag aaatcttcaa actgcttttc ataatagcta aactaattta cagtcccgcc    20940
agcagtgtat aagtgttccc ttttctccac aaccttgcca acatctgtga ttttttgact    21000
ttttaataat agccattcct agagaattga tttgcaattc tctattagtg atattaagca    21060 tttttttcata tgctttttag ctgtctgtat atattcttct gaaaattttt catgtccttt    21120
gcccagtttg tagtgggggtg ggttgttttt tgcttgttaa ttagttttaa gttccttcca    21180
gattctgcat atcccttttgt tggatacatg gtttgcagat attttttctcc cattgtgtag    21240
```

```
gttgtctttt actctgttga tagtttcttt tgccatgcag gagctcgtta ggtcccattt    21300
gtgtttgttt ttgttgcagt tgcttttggc gtcttcatca taaaatctgt gccagggcct    21360
atgtccagaa tggtatttcc taggttgtct tccagggttt ttacaattt agattttacg     21420 tttatgtctt taatccatct tgagttgatt tttgtatatg gcacaaggaa ggggtccagt    21480
ttcactccaa ttcctatggc tagcaattat cccagcacca tttattgaat acggagtcct    21540
ttccccattg cttgtttttt gtcaacttg ttgaagatca gatggttgta agtgtgtggc     21600
tttatttctt ggctctctat tctccattgg tctatgtgtc tgttttata acagtaccct     21660 gctgttcagg ttcctatagc cttttagtat aaaatcggct aatgtgatgc ctccagcttt    21720 gttcttttg cttaggattg ctttggctat ttgggctcct ttttgggtcc atattaattt     21780
taaaacagtt ttttctggtt ttgtgaagga tatcattggt agtttatagg aatagcattg    21840
aatctgtaga ttgctttggg cagtatggcc attttaacaa tattaattct tcctatctat    21900
gaatatggaa tgttttttcca tgtgtttgtg tcatctcttt atacctgatg tataaagaaa   21960
agctggtatt attcctactc aatctgttcc aaaaaattga ggaggaggaa ctcttcccta    22020
atgaggccag catcattctg ataccaaaac ctggcagaga cacaacagaa aaagaaaac    22080 ttcaggccaa tatccttgat gaatatagat gcaaaatcc tcaacaaaat actagcaaac    22140
caaatccagc agcacatcaa aaagctgatc tactttgatc aagtaggctt atccctggg    22200 atgcaaggtt ggttcaacat acacaaatca ataagtgtga ttcatcacat aaacagagct    22260
aaaaacaaaa accacaagat tatctcaata ggtagagaaa aggttgtcaa taaaatttaa    22320
catcctccat gttaaaaacc ttcagtaggt caggtgtagt gactcacacc tgtaatccca    22380
gcactttggg aggccaaggc gggcatatct cttaagccca ggagttcaag acgagcctag    22440
gcagcatggt gaaaccccat ctctacaaaa aaaaaaaaa aaaaaatta gcttggtatg     22500 gtgacatgca cctatagtcc cagctattca ggaggttgag gtgggaggat tgtttgagcc    22560
cgggaggcag aggttggcag cgagctgaga tcatgccacc gcactccagc ctgggcaacg    22620
gagtgagacc ctgtctcaaa aagaaaaat cacaaacaat cctaaacaaa ctaggcattg     22680
aaggaacatg cctcaaaaaa ataagaacca tctatgacag acccatagcc aatatcttac    22740
caaatgggca aaagctggaa gtattctcct tgagaaccgt aacaagacaa ggatgtccac    22800
tctcaccact ccttttcagc atagttctgg aagtcctagc cagagcaatc aggaaagaga    22860
aagaaagaaa gacattcaga taggaagaga agaagtcaaa ctatttctgt ttgcaggcag    22920
tataattctg tacctagaaa atctcatagt ctctgcccag aaactcctaa atctgttaaa    22980
aatttcagca agttttggc attctctata ctccaacacc ttccaaagtg agagcaaaat     23040
caagaacaca gtcccattca caatagccgc aaaacgaata aaatacctag gaatccagct    23100
aaccagggag gtgaaagatc tctatgagaa ttacaaaaca ctgctgaaag aaatcagaga    23160
tgacacaaac aaatggaaat gttcttttt aacaccttgc tttatctaat tcacttatga     23220
tgaagatact cattcagtgg aacaggtata ataagtccac tcgattaaat ataagcctta    23280
ttctctttcc agagcccaag aagggggcact atcagtgccc agtcaataat gacgaaatgc   23340 taatatttt cccctttacg gtttcttct tctgtagtgt ggtacactcg ttcttaaga      23400 taaggaaact tgaactacct tcctgtttgc ttctacacat acccattctc tttttttgcc    23460
actctggtca ggtataggat gatccctacc actttcagtt aaaaactcct cctcttacta   23520
aatgttctct taccctctgg cctgagtaga acctaggaa aatggaagag aaaaagatga    23580
```

```
aagggaggtg gggcctggga agggaataag tagtcctgtt tgtttgtgtg tttgctttag    23640
cacctgctat atcctaggtg ctgtgttagg cacacattat tttaagtggc cattatatta    23700
ctactactca ctctggtcgt tgccaaggta ggtagtactt tcttggatag ttggttcatg    23760
ttacttacag atggtgggct tgttgaggca aacccagtgg ataatcatcg gagtgtgttc    23820
tctaatctca ctcaaatttt tcttcacatt ttttggtttg ttttggtttt tgatggtagt    23880
ggcttatttt tgttgctggt ttgttttttg ttttttttg agatggcaag aattggtagt    23940
tttatttatt aattgcctaa gggtctctac tttttttaaa agatgagagt agtaaaatag    24000
attgatagat acatacatac ccttactggg gactgcttat attctttaga gaaaaaatta    24060
catattagcc tgacaaacac cagtaaaatg taaatatatc cttgagtaaa taatgaatg     24120
tatattttgt gtctccaaat atatatatct atattcttac aaatgtgttt atatgtaata    24180
tcaatttata agaacttaaa atgttggctc aagtgaggga ttgtggaagg tagcattata    24240
tggccatttc aacatttgaa cttttttctt ttcttcattt tcttcttttc ttcaggaata    24300
tttttcaaga tgtcttacac agagacactc tagtgaaagc cttcctggat caggtaaatg    24360
ttgaacttga gattgtcaga gtgaatgata tgacatgttt tctttttaa tatatcctac     24420
aatgcctgtt ctatatattt atattcccct ggatcatgcc ccagagttct gctcagcaat    24480
tgcagttaag ttagttacac tacagttctc agaagagtct gtgagggcat gtcaagtgca    24540
tcattacatt ggttgcctct tgtcctagat ttatgcttcg ggaattcaga cctttgttta    24600
caatataata aatattattg ctatctttta aagatataat aataagatat aaagttgacc    24660
acaactactg ttttttgaaa catagaattc ctggtttaca tgtatcaaag tgaaatctga    24720
cttagctttt acagatataa tatatacata tatatatcct gcaatgcttg tactatatat    24780
gtagtacaag tatatatata tgtttgtgtg tgtatatata tatagtacga gcatatatac    24840
atattaccag cattgtagga tatatatatg tttatatatt aaaaaaaagt tataaactta    24900
aaaccctatt atgttatgta gagtatatgt tatatatgat atgtaaaata tataacatat    24960
actctatgat agagtgtaat atattttta tatatatttt aacatttata aaatgataga    25020
attaagaatt gagtcctaat ctgttttatt aggtgctttt tgtagtgtct ggtctttcta    25080
aagtgtctaa atgatttttc cttttgactt attaatgggg aagagcctgt atattaacaa    25140
ttaagagtgc agcattccat acgtcaaaca acaaacattt taattcaagc attaacctat    25200
aacaagtaag ttttttttt tttttgaga aagggaggtt gtttatttgc ctgaaatgac      25260
tcaaaaatat ttttgaaaca tagtgtactt atttaaataa catctttatt gtttcattct    25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt gggagtccg aggtgggtgg     25920
atcacaaggt caggagatcg agaccatcct gccaacatgg tgaaaccccg tctctactaa    25980
```

```
gtatacaaaa attagctggg cgtggcagcg tgtgcctgta atcccagcta cctgggaggc   26040
tgaggcagga gaatcgcttg aacccaggag gtgtaggttg cagtgagtca agatcgcgcc   26100
actgcacttt agcctggtga cagagctaga ctccgtctca aaaaaaaaaa aaaatatcag   26160
attgttccta cacctagtgc ttctatacca cactcctgtt aggggggcatc agtggaaatg   26220 gttaaggaga tgtttagtgt gtattgtctg ccaagcactg tcaacactgt catagaaact   26280
tctgtacgag tagaatgtga gcaaattatg tgttgaaatg gttcctctcc ctgcaggtct   26340
ttcagctgaa acctggctta tctctcagaa gtactttcct tgcacagttt ctacttgtcc   26400
ttcacagaaa agccttgaca ctaataaaat atatagaaga cgatacgtga gtaaaactcc   26460
tacacggaag aaaaaccttt gtacattgtt tttttgtttt gtttcctttg tacattttct   26520
atatcataat ttttgcgctt cttttttttt tttttttttt ttttttttcca ttattttag   26580 gcagaaggga aaaagcccct ttaaatctct tcggaacctg aagatagacc ttgatttaac   26640
agcagagggc gatcttaaca taataatggc tctggctgag aaaattaaac caggcctaca   26700
ctcttttatc tttggaagac cttctacac tagtgtgcaa gaacgagatg ttctaatgac   26760
tttttaaatg tgtaacttaa taagcctatt ccatcacaat catgatcgct ggtaaagtag   26820
ctcagtggtg tggggaaacg ttcccctgga tcatactcca gaattctgct ctcagcaatt   26880
gcagttaagt aagttacact acagttctca caagagcctg tgaggggatg tcaggtgcat   26940
cattacattg ggtgtctctt ttcctagatt tatgcttttg ggatacagac ctatgtttac   27000
aatataataa atattattgc tatcttttaa agatataata ataggatgta aacttgacca   27060
caactactgt ttttttgaaa tacatgattc atggtttaca tgtgtcaagg tgaaatctga   27120
gttggctttt acagatagtt gactttctat cttttggcat tctttggtgt gtagaattac   27180
tgtaatactt ctgcaatcaa ctgaaaacta gagcctttaa atgatttcaa ttccacagaa   27240
agaaagtgag cttgaacata ggatgagctt tagaaagaaa attgatcaag cagatgttta   27300
attggaattg attattagat cctactttgt ggatttagtc cctgggattc agtctgtaga   27360
aatgtctaat agttctctat agtccttgtt cctggtgaac cacagttagg gtgttttgtt   27420
tattttattg ttcttgctat tgttgatatt ctatgtagtt gagctctgta aaaggaaatt   27480 gtatttatg ttttagtaat tgttgccaac ttttttaaatt aatttttcatt attttttgagc   27540 caaattgaaa tgtgcacctc ctgtgccttt tttctcctta gaaaatctaa ttacttggaa   27600
caagttcaga tttcactggt cagtcatttt catcttgttt tcttcttgct aagtcttacc   27660
atgtacctgc tttggcaatc attgcaactc tgagattata aaatgcctta gagaatatac   27720
taactaataa gatctttttt tcagaaacag aaaatagttc cttgagtact tccttcttgc   27780
atttctgcct atgttttttga agttgttgct gtttgcctgc aataggctat aaggaatagc   27840
aggagaaatt ttactgaagt gctgtttttcc taggtgctac tttggcagag ctaagttatc   27900
ttttgttttc ttaatgcgtt tggaccattt tgctggctat aaaataactg attaatataa   27960
ttctaacaca atgttgacat tgtagttaca caaacacaaa taaatatttt atttaaaatt   28020
ctggaagtaa tataaagggg aaaatatatt tataagaaag ggataaaggt aatagagccc   28080
ttctgccccc cacccaccaa atttacacaa caaaatgaca tgttcgaatg tgaaaggtca   28140
taatagcttt cccatcatga atcagaaaga tgtggacagc ttgatgtttt agacaaccac   28200
tgaactagat gactgttgta ctgtagctca gtcatttaaa aaatatataa atactacctt   28260
gtagtgtccc atactgtgtt ttttacatgg tagattctta tttaagtgct aactggttat   28320
```

```
tttctttggc tggtttattg tactgttata cagaatgtaa gttgtacagt gaaataagtt    28380
attaaagcat gtgtaaacat tgttatatat ctttctcct aaatggagaa ttttgaataa     28440
aatatatttg aaattttgcc tctttcagtt gttcattcag aaaaaaatac tatgatattt    28500
gaagactgat cagcttctgt tcagctgaca gtcatgctgg atctaaactt tttttaaaat    28560
taattttgtc ttttcaaaga aaaatatttt aaagaagctt tataatataa tcttatgtta    28620
aaaaaacttt ctgcttaact ctctggattt cattttgatt tttcaaatta tatattaata    28680
tttcaaatgt aaaatactat ttagataaat tgtttttaaa cattcttatt attataatat    28740
taatataacc taaactgaag ttattcatcc caggtatcta atacatgtat ccaaagtaaa    28800
aatccaagga atctgaacac tttcatctgc aaagctagga ataggtttga cattttcact    28860
ccaagaaaaa gttttttttt gaaaatagaa tagttgggat gagaggtttc tttaaaagaa    28920
gactaactga tcacattact atgattctca aagaagaaac caaaacttca tataatacta    28980
taaagtaaat ataaaatagt tccttctata gtatatttct ataatgctac agtttaaaca    29040
gatcactctt atataatact attttgattt tgatgtagaa ttgcacaaat tgatatttct    29100
cctatgatct gcagggtata gcttaaagta acaaaaacag tcaaccacct ccatttaaca    29160
cacagtaaca ctatgggact agttttatta cttccatttt acaaatgagg aaactaaagc    29220
ttaaagatgt gtaatacacc gcccaaggtc acacagctgg taaaggtgga tttcatccca    29280
gacagttaca gtcattgcca tgggcacagc tcctaactta gtaactccat gtaactggta    29340
ctcagtgtag ctgaattgaa aggagagtaa ggaagcaggt tttacaggtc tacttgcact    29400
attcagagcc cgagtgtgaa tccctgctgt gctgcttgga gaagttactt aacctatgca    29460
aggttcattt tgtaaatatt ggaaatggag tgataatacg tacttcacca gaggatttaa    29520 tgagaccta tacgatcctt agttcagtac ctgactagtg cttcataaat gcttttcat     29580 ccaatctgac aatctccagc ttgtaattgg ggcatttaga acatttaata tgattattgg    29640
catggtaggt taaagctgtc atcttgctgt tttctatttg ttcttttgt tttctcctta    29700 cttttggatt tttttattct actatgtctt ttctattgtc ttattaacta tactctttga    29760 tttatttag tggttgtttt agggttatac ctctttctaa tttaccagtt tataaccagt     29820
ttatatacta cttgacatat agcttaagaa acttactgtt gttgtctttt tgctgttatg    29880
gtcttaacgt ttttatttct acaaacatta taaactccac actttattgt ttttaattt     29940 tacttataca gtcaattatc tttaaagat atttaaatat aaacattcaa acacccca      30000
t                                                                    30001

<210> SEQ ID NO 3
<211> LENGTH: 1031
<212> TYPE: DNA
<213> ORGANISM: Homo sapiens

<400> SEQUENCE: 3
attcccggga tacgtaacct acggtgtccc gctaggaaag agaggtgcgt caaacagcga     60
caagttccgc ccacgtaaaa gatgacgctt ggtgtgtcag ccgtccctgc tgcccggttg    120
cttctctttt gggggcgggg tctagcaaga gcaggtgtgg gttaggagag tatctccgga    180
gcatttggat aatgtgacag ttggaatgca gtgatgtcga ctctttgccc accgccatct    240
ccagctgttg ccaagacaga gattgcttta agtggcaaat cacctttatt agcagctact    300
tttgcttact gggacaatat tcttggtcct agagtaaggc acatttgggc tccaaagaca    360
gaacaggtac ttctcagtga tggagaaata acttttcttg ccaaccacac tctaaatgga    420
```

```
gaaatccttc gaaatgcaga gagtggtgct atagatgtaa agttttttgt cttgtctgaa      480
aagggagtga ttattgtttc attaatcttt gatggaaact ggaatgggga tcgcagcaca      540
tatggactat caattatact tccacagaca gaacttagtt tctacctccc acttcataga      600
gtgtgtgttg atagattaac acatataatc cggaaaggaa gaatatggat gcataaggaa      660
agacaagaaa aatgtccaga agattatctt agaaggcaca gagagaatgg aagatcaggg      720
tcagagtatt attccaatgc ttactggaga agtgattcct gtaatggaaa ctgctttcct      780
ctatgaaatt ccccgggtt cctggaggaa atagatatag gctgatacag ttacccaatg       840
atggatgaat attgggggac cgcctggtca ttgaaaggct ttcttttctc caggaaagaa      900 attttttttcc ttttccataa aaagcttggg aatggaagac aacaattccc attctttttt      960
tgcgttccac ccctatgtga acacagaaat ttttggggaa acaacaacga aaaatttta      1020 tcccgcgcgc a                                                         1031

<210> SEQ ID NO 4
<211> LENGTH: 3244
<212> TYPE: DNA
<213> ORGANISM: Homo sapiens
<220> FEATURE:
<221> NAME/KEY: CDS
<222> LOCATION: (108)..(1553)

<400> SEQUENCE: 4
gggcggggct gcggttgcgg tgcctgcgcc cgcggcggcg gaggcgcagg cggtggcgag       60
tggatatctc cggagcattt ggataatgtg acagttggaa tgcagtg atg tcg act       116
                                                     Met Ser Thr
                                                       1 ctt tgc cca ccg cca tct cca gct gtt gcc aag aca gag att gct tta      164
Leu Cys Pro Pro Pro Ser Pro Ala Val Ala Lys Thr Glu Ile Ala Leu
        5                   10                  15 agt ggc aaa tca cct tta tta gca gct act ttt gct tac tgg gac aat      212
Ser Gly Lys Ser Pro Leu Leu Ala Ala Thr Phe Ala Tyr Trp Asp Asn
 20                  25                  30                  35 att ctt ggt cct aga gta agg cac att tgg gct cca aag aca gaa cag      260
Ile Leu Gly Pro Arg Val Arg His Ile Trp Ala Pro Lys Thr Glu Gln
             40                  45                  50 gta ctt ctc agt gat gga gaa ata act ttt ctt gcc aac cac act cta      308
Val Leu Leu Ser Asp Gly Glu Ile Thr Phe Leu Ala Asn His Thr Leu
         55                  60                  65 aat gga gaa atc ctt cga aat gca gag agt ggt gct ata gat gta aag      356
Asn Gly Glu Ile Leu Arg Asn Ala Glu Ser Gly Ala Ile Asp Val Lys
     70                  75                  80 ttt ttt gtc ttg tct gaa aag gga gtg att att gtt tca tta atc ttt      404
Phe Phe Val Leu Ser Glu Lys Gly Val Ile Ile Val Ser Leu Ile Phe
 85                  90                  95 gat gga aac tgg aat ggg gat cgc agc aca tat gga cta tca att ata      452
Asp Gly Asn Trp Asn Gly Asp Arg Ser Thr Tyr Gly Leu Ser Ile Ile
100                 105                 110                 115 ctt cca cag aca gaa ctt agt ttc tac ctc cca ctt cat aga gtg tgt      500
Leu Pro Gln Thr Glu Leu Ser Phe Tyr Leu Pro Leu His Arg Val Cys
             120                 125                 130 gtt gat aga tta aca cat ata atc cgg aaa gga aga ata tgg atg cat      548
Val Asp Arg Leu Thr His Ile Ile Arg Lys Gly Arg Ile Trp Met His
         135                 140                 145 aag gaa aga caa gaa aat gtc cag aag att atc tta gaa ggc aca gag      596
Lys Glu Arg Gln Glu Asn Val Gln Lys Ile Ile Leu Glu Gly Thr Glu
    150                 155                 160
```

-continued

| | | |
|---|---|---|
| aga atg gaa gat cag ggt cag agt att att cca atg ctt act gga gaa<br>Arg Met Glu Asp Gln Gly Gln Ser Ile Ile Pro Met Leu Thr Gly Glu<br>165                          170                   175 | | 644 |
| gtg att cct gta atg gaa ctg ctt tca tct atg aaa tca cac agt gtt<br>Val Ile Pro Val Met Glu Leu Leu Ser Ser Met Lys Ser His Ser Val<br>180                         185                 190               195 | | 692 |
| cct gaa gaa ata gat ata gct gat aca gta ctc aat gat gat gat att<br>Pro Glu Glu Ile Asp Ile Ala Asp Thr Val Leu Asn Asp Asp Asp Ile<br>                          200                 205               210 | | 740 |
| ggt gac agc tgt cat gaa ggc ttt ctt ctc aat gcc atc agc tca cac<br>Gly Asp Ser Cys His Glu Gly Phe Leu Leu Asn Ala Ile Ser Ser His<br>              215                 220               225 | | 788 |
| ttg caa acc tgt ggc tgt tcc gtt gta gta ggt agc agt gca gag aaa<br>Leu Gln Thr Cys Gly Cys Ser Val Val Val Gly Ser Ser Ala Glu Lys<br>           230                 235               240 | | 836 |
| gta aat aag ata gtc aga aca tta tgc ctt ttt ctg act cca gca gag<br>Val Asn Lys Ile Val Arg Thr Leu Cys Leu Phe Leu Thr Pro Ala Glu<br>245                          250                 255 | | 884 |
| aga aaa tgc tcc agg tta tgt gaa gca gaa tca tca ttt aaa tat gag<br>Arg Lys Cys Ser Arg Leu Cys Glu Ala Glu Ser Ser Phe Lys Tyr Glu<br>260                          265               270               275 | | 932 |
| tca ggg ctc ttt gta caa ggc ctg cta aag gat tca act gga agc ttt<br>Ser Gly Leu Phe Val Gln Gly Leu Leu Lys Asp Ser Thr Gly Ser Phe<br>                          280                 285               290 | | 980 |
| gtg ctg cct ttc cgg caa gtc atg tat gct cca tat ccc acc aca cac<br>Val Leu Pro Phe Arg Gln Val Met Tyr Ala Pro Tyr Pro Thr Thr His<br>                          295                 300               305 | | 1028 |
| ata gat gtg gat gtc aat act gtg aag cag atg cca ccc tgt cat gaa<br>Ile Asp Val Asp Val Asn Thr Val Lys Gln Met Pro Pro Cys His Glu<br>           310                 315               320 | | 1076 |
| cat att tat aat cag cgt aga tac atg aga tcc gag ctg aca gcc ttc<br>His Ile Tyr Asn Gln Arg Arg Tyr Met Arg Ser Glu Leu Thr Ala Phe<br>325                          330               335 | | 1124 |
| tgg aga gcc act tca gaa gaa gac atg gct cag gat acg atc atc tac<br>Trp Arg Ala Thr Ser Glu Glu Asp Met Ala Gln Asp Thr Ile Ile Tyr<br>340                          345               350               355 | | 1172 |
| act gac gaa agc ttt act cct gat ttg aat att ttt caa gat gtc tta<br>Thr Asp Glu Ser Phe Thr Pro Asp Leu Asn Ile Phe Gln Asp Val Leu<br>                          360                 365               370 | | 1220 |
| cac aga gac act cta gtg aaa gcc ttc ctg gat cag gtc ttt cag ctg<br>His Arg Asp Thr Leu Val Lys Ala Phe Leu Asp Gln Val Phe Gln Leu<br>           375                 380               385 | | 1268 |
| aaa cct ggc tta tct ctc aga agt act ttc ctt gca cag ttt cta ctt<br>Lys Pro Gly Leu Ser Leu Arg Ser Thr Phe Leu Ala Gln Phe Leu Leu<br>390                          395               400 | | 1316 |
| gtc ctt cac aga aaa gcc ttg aca cta ata aaa tat ata gaa gac gat<br>Val Leu His Arg Lys Ala Leu Thr Leu Ile Lys Tyr Ile Glu Asp Asp<br>405                          410               415 | | 1364 |
| acg cag aag gga aaa aag ccc ttt aaa tct ctt cgg aac ctg aag ata<br>Thr Gln Lys Gly Lys Lys Pro Phe Lys Ser Leu Arg Asn Leu Lys Ile<br>420                          425               430               435 | | 1412 |
| gac ctt gat tta aca gca gag ggc gat ctt aac ata ata atg gct ctg<br>Asp Leu Asp Leu Thr Ala Glu Gly Asp Leu Asn Ile Ile Met Ala Leu<br>                          440                 445               450 | | 1460 |
| gct gag aaa att aaa cca ggc cta cac tct ttt atc ttt gga aga cct<br>Ala Glu Lys Ile Lys Pro Gly Leu His Ser Phe Ile Phe Gly Arg Pro<br>                          455                 460               465 | | 1508 |
| ttc tac act agt gtg caa gaa cga gat gtt cta atg act ttt taa<br>Phe Tyr Thr Ser Val Gln Glu Arg Asp Val Leu Met Thr Phe | | 1553 |

```
                470         475         480
atgtgtaact taataagcct attccatcac aatcatgatc gctggtaaag tagctcagtg   1613
gtgtggggaa acgttcccct ggatcatact ccagaattct gctctcagca attgcagtta   1673
agtaagttac actacagttc tcacaagagc ctgtgagggg atgtcaggtg catcattaca   1733
ttgggtgtct cttttcctag atttatgctt tgggataca gacctatgtt tacaatataa   1793
taaatattat tgctatcttt taaagatata ataataggat gtaaacttga ccacaactac   1853 tgttttttg aaatacatga ttcatggttt acatgtgtca aggtgaaatc tgagttggct    1913
tttacagata gttgactttc tatcttttgg cattctttgg tgtgtagaat tactgtaata   1973
cttctgcaat caactgaaaa ctagagcctt taaatgattt caattccaca gaaagaaagt   2033
gagcttgaac ataggatgag ctttagaaag aaaattgatc aagcagatgt ttaattggaa   2093
ttgattatta gatcctactt tgtggattta gtccctggga ttcagtctgt agaaatgtct   2153
aatagttctc tatagtcctt gttcctggtg aaccacagtt agggtgtttt gtttatttta   2213
ttgttcttgc tattgttgat attctatgta gttgagctct gtaaaaggaa attgtatttt   2273
atgttttagt aattgttgcc aacttttaa attaattttc attattttg agccaaattg    2333 aaatgtgcac ctcctgtgcc tttttctcc ttagaaaatc taattacttg gaacaagttc    2393
agatttcact ggtcagtcat tttcatcttg ttttcttctt gctaagtctt accatgtacc   2453
tgctttggca atcattgcaa ctctgagatt ataaaatgcc ttagaaata tactaactaa    2513 taagatcttt ttttcagaaa cagaaaatag ttccttgagt acttccttct gcatttctg    2573 cctatgtttt tgaagttgtt gctgtttgcc tgcaataggc tataaggaat agcaggagaa   2633
attttactga agtgctgttt tcctaggtgc tactttggca gagctaagtt atcttttgtt   2693
ttcttaatgc gtttggacca ttttgctggc tataaaataa ctgattaata taattctaac   2753
acaatgttga cattgtagtt acacaaacac aaataaatat tttatttaaa attctggaag   2813
taatataaaa gggaaaatat atttataaga aagggataaa ggtaatagag cccttctgcc   2873
ccccacccac caaatttaca caacaaaatg acatgttcga atgtgaaagg tcataatagc   2933
tttcccatca tgaatcagaa agatgtggac agcttgatgt tttagacaac cactgaacta   2993
gatgactgtt gtactgtagc tcagtcattt aaaaaatata taaatactac cttgtagtgt   3053
cccatactgt gttttttaca tggtagattc ttatttaagt gctaactggt tattttcttt   3113
ggctggttta ttgtactgtt atacagaatg taagttgtac agtgaaataa gttattaaag   3173
catgtgtaaa cattgttata tatctttttct cctaaatgga gaattttgaa taaaatatat   3233 ttgaaattt g                                                         3244
```

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

```
cacgaggctt tgatatttct tacaacgaat ttcatgtgta gacccactaa acagaagcta    60
taaaagttgc atggtcaaat aagtctgaga aagtctgcag atgatataat tcacctgaag  120
```

```
agtcacagta tgtagccaaa tgttaaaggt tttgagatgc catacagtaa atttaccaag    180
cattttctaa atttatttga ccacagaatc cctattttaa gcaacaactg ttacatccca    240
tggattccag gtgactaaag aatacttatt tcttaggata tgttttattg ataataacaa    300
ttaaaatttc agatatcttt cataagcaaa tcagtggtct ttttacttca tgttttaatg    360
ctaaaatatt ttcttttata gatagtcaga acattatgcc ttttctgac tccagcagag    420 agaaaatgct ccaggttatg tgaagcagaa tcatcattta aatatgagtc agggctcttt    480
gtacaaggcc tgctaaagga ttcaactgga agctttgtgc tgcctttccg gcaagtcatg    540
tatgctccat atcccaccac acacatagat gtggatgtca atactgtgaa gcagatgcca    600
ccctgtcatg aacatattta taatcagcgt agatacatga gatccgagct gacagccttc    660
tggagagcca cttcagaaga agacatggct cangatacga tcatctacac tgacgaaagc    720
tntactcctg atttgaatat ttttcaagat gtcttacaca g                       761

<210> SEQ ID NO 6
<211> LENGTH: 1901
<212> TYPE: DNA
<213> ORGANISM: Homo sapiens
<220> FEATURE:
<221> NAME/KEY: CDS
<222> LOCATION: (125)..(793)

<400> SEQUENCE: 6
acgtaaccta cggtgtcccg ctaggaaaga gaggtgcgtc aaacagcgac aagttccgcc     60
cacgtaaaag atgacgcttg atatctccgg agcatttgga taatgtgaca gttggaatgc    120 agtg atg tcg act ctt tgc cca ccg cca tct cca gct gtt gcc aag aca    169
     Met Ser Thr Leu Cys Pro Pro Pro Ser Pro Ala Val Ala Lys Thr
       1               5                  10                  15 gag att gct tta agt ggc aaa tca cct tta tta gca gct act ttt gct    217
Glu Ile Ala Leu Ser Gly Lys Ser Pro Leu Leu Ala Ala Thr Phe Ala
             20                  25                  30 tac tgg gac aat att ctt ggt cct aga gta agg cac att tgg gct cca    265
Tyr Trp Asp Asn Ile Leu Gly Pro Arg Val Arg His Ile Trp Ala Pro
         35                  40                  45 aag aca gaa cag gta ctt ctc agt gat gga gaa ata act ttt ctt gcc    313
Lys Thr Glu Gln Val Leu Leu Ser Asp Gly Glu Ile Thr Phe Leu Ala
     50                  55                  60 aac cac act cta aat gga gaa atc ctt cga aat gca gag agt ggt gct    361
Asn His Thr Leu Asn Gly Glu Ile Leu Arg Asn Ala Glu Ser Gly Ala
 65                  70                  75 ata gat gta aag ttt ttt gtc ttg tct gaa aag gga gtg att att gtt    409
Ile Asp Val Lys Phe Phe Val Leu Ser Glu Lys Gly Val Ile Ile Val
 80                  85                  90                  95 tca tta atc ttt gat gga aac tgg aat ggg gat cgc agc aca tat gga    457
Ser Leu Ile Phe Asp Gly Asn Trp Asn Gly Asp Arg Ser Thr Tyr Gly
                100                 105                 110 cta tca att ata ctt cca cag aca gaa ctt agt ttc tac ctc cca ctt    505
Leu Ser Ile Ile Leu Pro Gln Thr Glu Leu Ser Phe Tyr Leu Pro Leu
            115                 120                 125 cat aga gtg tgt gtt gat aga tta aca cat ata atc cgg aaa gga aga    553
His Arg Val Cys Val Asp Arg Leu Thr His Ile Ile Arg Lys Gly Arg
        130                 135                 140 ata tgg atg cat aag gaa aga caa gaa aat gtc cag aag att atc tta    601
Ile Trp Met His Lys Glu Arg Gln Glu Asn Val Gln Lys Ile Ile Leu
    145                 150                 155 gaa ggc aca gag aga atg gaa gat cag ggt cag agt att att cca atg    649
Glu Gly Thr Glu Arg Met Glu Asp Gln Gly Gln Ser Ile Ile Pro Met
```

```
                Glu Gly Thr Glu Arg Met Glu Asp Gln Gly Gln Ser Ile Ile Pro Met
                160                 165                 170                 175 ctt act gga gaa gtg att cct gta atg gaa ctg ctt tca tct atg aaa          697
Leu Thr Gly Glu Val Ile Pro Val Met Glu Leu Leu Ser Ser Met Lys
                    180                 185                 190 tca cac agt gtt cct gaa gaa ata gat ata gct gat aca gta ctc aat          745
Ser His Ser Val Pro Glu Glu Ile Asp Ile Ala Asp Thr Val Leu Asn
                    195                 200                 205 gat gat gat att ggt gac agc tgt cat gaa ggc ttt ctt ctc aag taa          793
Asp Asp Asp Ile Gly Asp Ser Cys His Glu Gly Phe Leu Leu Lys
            210                 215                 220 gaatttttct tttcataaaa gctggatgaa gcagatacca tcttatgctc acctatgaca       853
agatttggaa gaaagaaaat aacagactgt ctacttagat tgttctaggg acattacgta       913
tttgaactgt tgcttaaatt tgtgttattt tcactcatt  atatttctat atatatttgg       973
tgttattcca tttgctattt aaagaaaccg agtttccatc ccagacaaga aatcatggcc      1033
ccttgcttga ttctggtttc tgtttttact tctcattaaa gctaacagaa tcctttcata      1093
ttaagttgta ctgtagatga acttaagtta tttaggcgta gaacaaaatt attcatattt      1153
atactgatct ttttccatcc agcagtggag tttagtactt aagagtttgt gcccttaaac      1213
cagactccct ggattaatgc tgtgtacccg tgggcaaggt gcctgaattc tctatacacc      1273
tatttcctca tctgtaaaat ggcaataata gtaatagtac ctaatgtgta gggttgttat      1333
aagcattgag taagataaat aatataaagc acttagaaca gtgcctggaa cataaaaaca      1393
cttaataata gctcatagct aacatttcct atttacattt cttctagaaa tagccagtat      1453
tgttgagtg  cctacatgtt agttccttta ctagttgctt tacatgtatt atcttatatt      1513
ctgtttaaa  gtttcttcac agttacagat tttcatgaaa ttttacttt  aataaaagag      1573
aagtaaaagt ataaagtatt cacttttatg ttcacagtct tttcctttag gctcatgatg      1633
gagtatcaga ggcatgagtg tgtttaacct aagagcctta atggcttgaa tcagaagcac      1693
tttagtcctg tatctgttca gtgtcagcct ttcatacatc attttaaatc ccatttgact      1753
ttaagtaagt cacttaatct ctctacatgt caatttcttc agctataaaa tgatggtatt      1813
tcaataaata aatacattaa ttaaatgata ttatactgac taattgggct gttttaaggc      1873
aaaaaaaaaa aaaaaaaaaa aaaaaaaa                                         1901
```

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

```
agacgtaacc tacggtgtcc cgctaggaaa gagagatatc tccggagcat ttggataatg    60
tgacagttgg aatgcagtga tgtcgactct ttgcccaccg ccatctccag ctgttgccaa   120
gacagagatt gctttaagtg gcaaatcacc tttattagca gctacntttt gcttactggg   180
acaatattct tggtcctaga gtaaggcaca tttgggctcc aaagacagaa caggtacttc   240
tcagtgatgg agaaataact tttcttgcca accacactct aaatggagaa tccttcgaa    300
atgcagagag tggtgctata gatgtaaagt tttttgtctt gtctgaaaag ggagtgatta   360
ttgtttcatt aatctttgat ggaaactgga atggggatcg cagcacatat ggactatcaa   420
```

```
ttatacttcc acagacagaa cttagtttct acctcccact tcatagagtg tgtgttgata      480
gattaacaca tataatccgg aaaggaagaa tatggatgca taaggaaaga caagaaaatg      540
tccagaagat tatcttagaa gg                                              562

<210> SEQ ID NO 8
<211> LENGTH: 798
<212> TYPE: DNA
<213> ORGANISM: Homo sapiens
<220> FEATURE:
<221> NAME/KEY: CDS
<222> LOCATION: (81)..(590)

<400> SEQUENCE: 8
gggctctctt ttgggggcgg ggtctagcaa gagcagatat ctccggagca tttggataat       60
gtgacagttg aatgcagtg atg tcg act ctt tgc cca ccg cca tct cca gct      113
                     Met Ser Thr Leu Cys Pro Pro Pro Ser Pro Ala
                      1               5                  10 gtt gcc aag aca gag att gct tta agt ggc aaa tca cct tta tta gca      161
Val Ala Lys Thr Glu Ile Ala Leu Ser Gly Lys Ser Pro Leu Leu Ala
         15                  20                  25 gct act ttt gct tac tgg gac aat att ctt ggt cct aga gta agg cac      209
Ala Thr Phe Ala Tyr Trp Asp Asn Ile Leu Gly Pro Arg Val Arg His
     30                  35                  40 att tgg gct cca aag aca gaa cag gta ctt ctc agt gat gga gaa ata      257
Ile Trp Ala Pro Lys Thr Glu Gln Val Leu Leu Ser Asp Gly Glu Ile
 45                  50                  55 act ttt ctt gcc aac cac act cta aat gga gaa atc ctt cga aat gca      305
Thr Phe Leu Ala Asn His Thr Leu Asn Gly Glu Ile Leu Arg Asn Ala
60                  65                  70                  75 gag agt ggt gct ata gat gta aag ttt ttt gtc ttg tct gaa aag gga      353
Glu Ser Gly Ala Ile Asp Val Lys Phe Phe Val Leu Ser Glu Lys Gly
                 80                  85                  90 gtg att att gtt tca tta atc ttt gat gga aac tgg aat ggg gat cgc      401
Val Ile Ile Val Ser Leu Ile Phe Asp Gly Asn Trp Asn Gly Asp Arg
             95                 100                 105 agc aca tat gga cta tca att ata ctt cca cag aca gaa ctt agt ttc      449
Ser Thr Tyr Gly Leu Ser Ile Ile Leu Pro Gln Thr Glu Leu Ser Phe
        110                 115                 120 tac ctc cca ctt cat aga gtg tgt gtt gat aga tta aca cat ata atc      497
Tyr Leu Pro Leu His Arg Val Cys Val Asp Arg Leu Thr His Ile Ile
    125                 130                 135 cgg aaa gga aga ata tgg atg cat aag gaa aga caa gaa aat gtc cag      545
Arg Lys Gly Arg Ile Trp Met His Lys Glu Arg Gln Glu Asn Val Gln
140                 145                 150                 155 aag att atc tta gaa ggc aca gag aga atg gaa gat cag ggt cag          590
Lys Ile Ile Leu Glu Gly Thr Glu Arg Met Glu Asp Gln Gly Gln
                160                 165                 170 agtattattc caatgcttac tggagaagtg attcctgtaa tgggactgct ttcatctatg      650
aaatcacaca gtgttcctga agaaatagat atagctgata cagtactcca tgatgatgat      710
atttggtgac agctgtcatg aaaggctttc ttctcaagta ggaattttt cttttcataa       770 aagctgggat gaagccagat tcccatct                                         798

<210> SEQ ID NO 9
<211> LENGTH: 169
<212> TYPE: DNA
<213> ORGANISM: Homo sapiens

<400> SEQUENCE: 9
```

```
aaacagcgac aagttccgcc cacgtaaaag atgatgcttg gtgtgtcagc cgtccctgct    60
gcccggttgc ttctcttttg ggggcggggt ctagcaagag cagatatctc cggagcattt   120
ggataatgtg acagttggaa tgcggtgatg tcgactcttt gcccaccgc              169
```

<210> SEQ ID NO 10
<211> LENGTH: 176
<212> TYPE: DNA
<213> ORGANISM: Homo sapiens

<400> SEQUENCE: 10

```
aaaacgtcat cgcacataga aaacagacag acgtaaccta cggtgtcccg ctaggaaaga    60
gaggtgcgtc aaacagcgac aagttccgcc cacgtaaaag atgacgcttg atatctccgg   120
agcatttgga taatgtgaca gttggaatgc agtgatgtcg actctttgcc caccgc       176
```

<210> SEQ ID NO 11
<211> LENGTH: 38001
<212> TYPE: DNA
<213> ORGANISM: Mus musculus

<400> SEQUENCE: 11

```
caaacacaca cacacacaca cacacacaca cacacacaca cacacacaca cacacactgg    60
catatcaagt ctctgttagg ctaggcgcat cctctcccac tgaggtcaga caagactgcc   120
cagctagaag aacatatccc acggacaggc aacagctttt gggacagcca cgctccagtt   180
gtttgggact cataaaagac taaactcaca cctgctacaa aagtgcaggg aggcctaggt   240
ccagcctgtg tgtgctcttt gcttagtggt gtctctgaga gccctaagga tcaaagtttg   300
ttgactctgt tggtcttcct gtggagttcc tatccccttc gtcccctcc ccaccctgca    360
atctttccct caactcttct ttaggcctgg tggtggtggt gtggtggcat ggaggaggtg   420
gtggagggg tggggtctt taatcccggt tcttgtgaga ccgaagcagg gacgatttcg     480
gagctctgtg agtttgaggc cagcctggtc tatagatcta gttccaggac agtcagagct   540
acatagagaa accctgcccc gagggggggg gggcgcgggg aatggttaaa gattattgca   600
ggacccagct gatctgtgga agaggtaacg ggtgtttatg ttttttcgaaa ctcattgaac   660
aatgcacttc aattgtgcgc actttagaaa tataaagcca ccacgcgaaa agctgcgccc    720
caacttaaag gcaatttcca aggtacttct gggtccttgc ggttcagtgg ctgtctaggt   780
tcagaaacga aactggatcc ccgccccgcc ccccgcccc ccccctcccc agcgccctga    840
ggcagtttcg atttcctatg gccagccggc taggcagctt tttcatcggg actccttgga   900
aagtccccac ttcgttcatc tctggcggat ttgcgggagc cagggcgctc atcgatcgcc   960
tggagccaca gaatgacagc ggagcagcgg cagaatctgc aagcattcag agactatatc  1020
aagaagattc tggaccccac ctacatcctc agctacatga gttcctggct cgaggatggt  1080
gagtggtccc caactggggc tctcaggctc tccaccttag cgaggggaaa acatcactca  1140
gatcagaaac aattgaaggc tctgcccccc ccctcccc gcgctgtcct taagttaatt   1200
tgtgtaaccc ggtgtatgtg agactcccag gccatattag agtagacagc atagggattt  1260
gatggtcagg aacaaaattc ctgcaagctg tagtaacttg cataaggatg ccactctttt  1320
ctttctttca atgctgggga aatagtttgt ttctcttatt tacaccttct agactgctgt  1380
gtgcctccct ttgtcctgtc atgagaaact gagaaatcag aatgcgcccg ccctccttta   1440
gattcctgta cagagcaaag agcaaggctt gggctcggg ccaaaggtgg aggtgggggc   1500
cgcaggaagc aagaggactg actgacacgc acatttctgt caaggatgt tgctcacagg   1560
```

```
aagtccgtgg aagaaaactt tctccagact ccgtgtgttc agagtttaac acagttgttc    1620
atatctagct ttggggattt gattggtgga taatagactc tttgtaaatt gcactgggtg    1680
tttccacctg agcaaacaga cctcccacc tcaccccac ccccagggag aagggagagg      1740
gcgtttgaag gggtgaccga gggcgtgcgg cagctacttt tcattttgcc agttaaagcc    1800
tagatgtctt tcctggcgtt ggacgacggt ggcaactgca ggttaattct gactctcttg    1860
agttccgaag cctaacaggc tatgcagaga ggagtaaaag agcactaccc agggctaccc    1920
acatcccggt tgtgttagag agaagcagca aaaaagccct aatgattggg ggcggggtct    1980
gaggagagga aacccaccca agaggtttct taacaccagg gtcacttgcc tttcaatcct    2040
ttaatctgat ctttagtcat ttacattagc atacaaagta actagtttca atactgaaac    2100
aaagtaacta gttgttcag ccattcctgc cattgctctt tgttcttatt taattgcctc     2160
ttctgtggct cttccacccc ctttacctgt ccctctctgg atgccctccc ccccaaatgg    2220
taccccgttc tgcttcctta taacatgagg ttcatcacac tccctccctc cctccctccc   2280
ccatttaaag tatcatcctt tcctctcagg gtgcctgttt tagtttcatg aattttaggg    2340
ttttggtttt ttgtctgttt agttatgaga ttttttttaaa aatgtggatt atgttgaatt   2400
tgtagattgt tcttggtgct agaggccttt ttatagtatt atttccaccc atcttgggag    2460
atctttctga aatcttccag tgtcttcaag aattttttt tcccactgcc ttagaagttt     2520
gcattgtagc tatcgttcac ctcttggtt agggtttgtt gttatttgtt tgtttgaggc     2580
tattgtgaat agaactccct ccttccccca tatctttctg ggccaggttg ttcttagtat    2640
gtaagtaagc tactggtttc tgtatgttta tttagaaccc tgcctcttgg ttgactttt    2700
atgagggctg agagtttgtg gtagtctttg ggggtctttt ataggattat ataagaatca    2760
tttgactcat tcctttccta tttgtctaac ttttgtttgt ttgtttgttt gtttttttga    2820
gacagggttt ctctgtatag ccctggcagt cctggaactc actttgtaga ccaggctggc    2880
ctcgaactca gaaatctgcc tgcctctgcc tcccgagtgc tgggattaaa ggcgtgcacc    2940
accacacccg gccatcattt ccaagttaaa gatttgatct acattagacg ccgccacgca    3000
gaaaaccttg agacttggtg gaaaggccaa aggccattaa aataaatttt cttttttctt    3060
tcttccattc tttcctttat tccttccttc ctttctttttt gttttctttc ttttctttt    3120
cctttttcct gagacagggt ttctctgtat agccctggca tcctggaact cactctgtag    3180
accaggctgg cctcgaactc agaaatccac cagcctttgc ctcccaagtg ttgggattaa    3240
aggcattcgc caccactgcc caaatatttt atttatttat ttatttattt attttatat    3300
atgtgatgag tacactggaa attccatcaa aaagagcagg tttgactggt gtcactagat    3360
ttactattga tagggatccc taaaggagag ctaaggtaaa gggctctccc tctcctaggt    3420
cttctgcata ccttccttga gtgttctggg ccagatctcc taagctctaa gaatgtgctg    3480
aaaacacact gggaactggc tccctccttg ggaatttgta ctccctctgc tgtgggaaac    3540
ttggatataa gaggctacag gaggacagtg agttataccc caggcacaga gttagcgtgt    3600
acattcaaaa cgcataccat tttgaaagta gcagctgcta gcatttcctg tcacctggtc    3660
aacctggtct ctttagctgc cccacccctt ccactttct gctgtgtttc ttttactctc     3720
ttagcaaaaa ttggaatgaa agaccacaaa tgtatttgta attcaaaatg cttgctgcat    3780
cagctatact cgttactgtt gccataggc gttcattccc acccaccccc aacccttag     3840
tccagcagtt gcttcagagt tttgaagaag aggaggaagc cttcttctt ccatgtgaca    3900
```

```
ccctccactg cgacttctgc ttactgtggg gaacttgagt ggaggacggg agtgtgcata    3960
gatgaaagag tggaggacgg gagtgtgcat agatgaagga gtggaggacg ggagtgtgca    4020
tacatgaagg agtggaggac gggagtgtgc atacatgaag gagtggagga cgggagtgtg    4080
catacatgaa ggagtggagg acgggagtgt gcatacatga aggagtggag gatgggagtg    4140
tgcatacatg aaggagtgga ggacgggagt gtgcatacat gaaggagtgg aggacgggag    4200
tgtgcataca tgaaggagag gaggacggga gtgtgcatag atgaaggaga ggaggacggg    4260
agtgtgcata gatgaaggag aggaggacgg gagtgtgcat agatgaagga gaggaggacg    4320
ggagtgtgca tagatgaagg agaggaggac gggagtgtgc atagatgaag gagtggagga    4380
cgggagtgtg catacatgaa ggagtggagg acgggagtgt gcatacatga aggagtggag    4440
gacgggagtg tgcatacatg aaggagtgga ggacgggagt gtgcatacat gaaggagtgg    4500
aggacgggag tgtgcataca tgaaggagag gaggacggga gtgtgcatag atgaaggaga    4560
ggaggacggg agtgtgcata gatgaaggag aggaggacgg gagtgtgcat agatgaagga    4620
gaggaggacg gagtgtgcat agatgaagga aaggaggac gggagtgtgc atagatgaag    4680
gagtggagga cgggagtgtg catacatgaa ggagtggagg acgggagtgt gcatacatga    4740
aggagtggag gacgggagtg tgcatatgaa ggagtggagg acgggagtgt gcatacatga    4800
aggagtggag gacgggagtg tgcatagatg aaggagagga ggacgggagt gtgcatagat    4860
gaaggagagg aggacgggag agtgcataga tgaaggagtg gaggacggga gtgtgcatac    4920
atgaaggagt ggaggacggg agtgtgcata catgaaggag tggaggacgg gagtgtgcat    4980
agatgaagga gaggaggacg ggagtgtgca tagatgaagg agaggaggac gggagagtgc    5040
atagatgaag gagtggagga cgggagtgtg catagatgaa ggagtggagg acgagagtgt    5100
gcatacatga aggagtggag gacgggagtg tgcgaggatg gatgagtgga gtctgctgcc    5160
tctcaaaggt cttctggttc catgagttgt tatgactccc agacccacat gggaaggtct    5220
ggtctgttat cttccagtga ctagtgcttc tgcaggctac tcacttgccc ttgcttctgt    5280
ttgcagagga ggtgcagtac attcaggctg agaagaacaa caagggccca atggaagctg    5340
cctcactctt cctccagtac ctgttgaagc tgcagtcaga gggctggttc caggcctttt    5400
tggatgccct gtaccatgca ggttggttcc ttcttcttcc tcacagttca gagtacttca    5460
ctctgctgcc tcagaaggct gagggagaaa aagtgactcg ttctgtgaca tctgtgtgtg    5520
gcttctgcct caggcgggaa atgtaaagac tattttgaat cagataagag aatggtttat    5580
accagaaata tccaaagcaa tctacagagt tgtaactact aggagaggtg acaatattag    5640
tagcatgccg gtatctttca agaggagaac gagtaaataa atcggtttta taatgtttac    5700
agtgctccat tatactgcaa tgaagcgtgt ggacatgtct gtaaatgaca acccagctga    5760
actgtaggca cgcagcattt aaatttgaat atcataaact ataatagcta taaagttcca    5820
catgagtcaa actaaacata tagggaagga aactggatct tgggcgaccc tggctgacca    5880
gtcctgggga gtaagcttaa taaactctcc ctgtctgact gagatcggtg tcctgtggtt    5940
tgtgaggcaa ttcctggact ctaacactta ggcaattaca tttcttgccc ctctgccact    6000
ctagcttatt cactggtgaa agaaggagaa tactttagtg ttaccaacaa tggggggggg    6060
ggggcggggg atgggaaatg ggaaaaagca ggcccggccc agtgtagtaa gaaagaaaca    6120
ccaaagaaag ccaagggctc ctgttgcttt cattgtattg gagtgtttgt cagtcggctg    6180
ggggatgggt gggggtgg ggaagcacac ctttaatccc agctctgggg aggcagaggc    6240
aggcagatcc ctgtgagctc caccagtcat ggctggcctc agcaagaact gtatccatca    6300
```

| | |
|---|---|
| catcctaaca caggtgtgtt gaattaacat ggtactgtta aagcaaacac gctgccttcc | 6360 |
| tcgggtgctg cggtccctag gaagccacac attggcagca tgttggcagc agttgtataa | 6420 |
| aaactaatgc ttttttttcc ttttcttttt aattcggtaa aagggtttaa atgtcatttg | 6480 |
| ttataaaact tggtttcctg ctatttccag gattaacaat tgacttattc tttctatttc | 6540 |
| ctgctttata gaccatcatt ttgatacatt atctatttgc atctcagtga tacatgctta | 6600 |
| tcttaccctt ttatttcgtt ttaagaattg tgtgtgtgtg tgtgtgtgtg tgtgtgtgtg | 6660 |
| tgtgtgtgtg tgtgtgtgtg tgtctgagag tgggcatgca tttatgagtg cattgcctag | 6720 |
| aggtcagaca ttcccctgga gctggagtta atggcagttg tgagggactg acgtgggtgc | 6780 |
| tgggatctga ccccagtccc ctgcaagaac acgatgaacc ttacttgcta agccatctcc | 6840 |
| ccagccctta gctgttgcag ttactctcca ttccaaataa gccctggcaa tgaaaacaag | 6900 |
| acttaattca tatgaataca tgctgtgcac ctagattggg cagatctacc gctacactac | 6960 |
| catcttctcc atctatgaga ctcccccttt tttttttctt tttttcttt ttgtggtttt | 7020 |
| ggttttttga dcagggttt ctctgtatag ccctggctgt cctggaactc actttgtaga | 7080 |
| ccaggctggc ctcgaactca gaaatccgcc tgcctctgcc tcccaagtgc tgggaattaa | 7140 |
| ggcgtgcgcc accaggcggt ttctccaggc tgtgtgcttc tgctccactt ttcttcctcc | 7200 |
| tcctctgtgg tatcctctcc ctcttcctct ttctccttct ctcttcccac cttcctctcc | 7260 |
| aacttccctt tatcagccca atcaccagct ctcctttatt ttactaattg aggtgggaag | 7320 |
| caggtttaca ggaaatcacc ggagtgctga ctcattcctt gttcgcagcc actcaatgca | 7380 |
| gaatggaatt accatcaaat ataattagcc ccagggctat ccacaacact tacctagcac | 7440 |
| atcaaatggc ccagcagggg atcaagagaa aaggaaactc aacttctgct tatttcctc | 7500 |
| atctcttatg tagccccatc agagaagctg ttgttttcct tttgtgggct ctaactaatt | 7560 |
| tgaatattat atttaagatc tattctctta agtaaaaatg gcacagctaa ctttaactgt | 7620 |
| aaaattatat gaggtttact aggaaaagtc ttgagtttaa gcaagaaagg gaattttaaa | 7680 |
| acatttgtat tggaacataa gtgctggaac atctctcttt gcaagtgagg tgctttgtgt | 7740 |
| gtacaaccct aagagtttct ttttttttt ttttaattt atttacttca tatttcagac | 7800 |
| agatctcatt tcaggtggtt gtgagccacc atgtggttgc tgggatttga actcaggacc | 7860 |
| tctggaagag cagtcagtgc tcctctgcgc tgagccatct ctccagcccc cctaagagtt | 7920 |
| tcataaagga atagtctgca ttaataaatt cagaaaaggc tcagaatata aagccaatat | 7980 |
| catcaagtag gtttccagtt tatgtattaa caaataatgc aaaaaagatt ttaagcaagc | 8040 |
| gattccttt ataacagcac caagaacaat aaagttagga atgccagtgc tcctaactgc | 8100 |
| tgaaccacct cagcaatgca aacttttaca tcttagcact aagtccagct cctaattcgt | 8160 |
| gaatgtaaga tgtcattcat gtccgtgtcc ctatggttcg tttcagaagt ggtttatggt | 8220 |
| cttcgggtca taggtctttc ccctgctcag ctttgcttat tcctaacttt atttaaagtt | 8280 |
| ctcactgttg ttataaaagg aatcacttgg ggctggcgag atggctcagt gggtaagagc | 8340 |
| acccgactgc tcttccgaag gtcctgagtt caaatcccag caaccacatg gtggctcaca | 8400 |
| accatccgta acgagatctg actccctctt ctggagtgtc ggaagacagc tacagtgtat | 8460 |
| ttacatataa taaataaata aataaataaa tcttcaaaaa aattctaaaa aaatatggaa | 8520 |
| aaaaaaggaa tcacttagtt aaaaatctca ttcctagccg ttgtggtgg cacatacctt | 8580 |
| taatcccagc acttgggtgg cagaggcagg cggatttcta agtttgaggt ctacaaagtg | 8640 |

```
agttccaggt ctctgaaaac cacaaaaaaa aaaaaaaaaa atagcactgg ctgctcttcc      8700
gaaggttctg agttcaaatc cctccaacca catagtggct cacaaccata tgtaatggga      8760
tctgatgccc tcttctggtg tgtctgaaga cagtaacagt gtacttacat ataataaata      8820
aataaatctt tgggtgggag tgagcggggc tggagagaga aggaaaagta tctgaagaca      8880
actacagtgt acttacatat aatagataaa taaatcttta aaaaaatcaa taaatgaaag      8940
atgccaatat tacccagagt tggcacagtg atacctttca taatgccaaa ttttggtggc      9000
aggattgttt gtttattaaa caggaataga aaaatttact ctcaaatttg tatgaaatct      9060
taaatggtca aaatattgga aagagaaact cacttggaaa ccttggggga cttatacttc      9120
ctggtgtcaa aacagtacag aacctccata aagccagata attagaccat tagcccagaa      9180
gtaaactctg aaggatatgg ccaaaggttc ttcaacaagg gtaccatgac cacccaaaag      9240
ggggaaaaaa aacccagtcc ctttaatatg aaaatacatt ggggtaagtg ggtatacata      9300
tgggaatgag aggtatcagg cataatcttg tgctatgatg tgaatttgaa atgttctcat      9360
cacattcatg ttttgagtgc ttggtcccca gcttgtgggg ttttaggagg tagagcctag      9420
ctagccaaag taacacgtgt atacgttcat gcatgtgtgc acacaggtat gagggtactt      9480
gtgtgtagcc cagaggctga cattcagtgt cttccttagg agctctccac cgtatgtttt      9540
tgggaatgga tctctcatta gacccagaat ttaccctctc gggctcgact ggctgggatt      9600
atagggtcat gctgctacac ttggcttttt acatgatagc tggggacagg aactcaggtc      9660
ccagccttgt gtggtgagca cttttctact aagcaccttc ttggtcctgg agctattttg      9720
attgttttag ttttttgggt ctatagggg gagaaaaaaa aaaaaaccac attgtcttcc      9780
cagggccttg aatgaagtaa atgagggtct gagaggcagg cacgcctggt ggatctgtcc      9840
aaaaacccca gagtacggca ttcttggatt ctttagtca gaagtcattt tccttctcca      9900
tttgcccatt gacttaatct tttcttggaa tggtgtggaa ggaaacactt ttcaagggca      9960
ggatgtaaga tttgtatttc ctctggtctt ctttactgtt tcctcttgag aagataaaca     10020
tgatgaattt gactaattta aaagtaaatt gagatgacaa agagatggct ctgtgattaa     10080
gagcacttgc tgatcttgca gaggacccag gtttggttcc tagacttaca tggtagctca     10140
caaccatctg taacttcagt tccaggaatc tgaccctctc ttctgctctc caaagatacc     10200
agacacactc acgatacaca gacacatgca aagtaaaata gaaataaata ttaaaaaaaa     10260
atatattgtg ggttgttgtt aaagtgcgtg aggggcattt tgaagatttt attctaaggt     10320
caaatacaag gcctcatatc tgtccttagg acttgaccct gaaagataat gaattttagg     10380
agacctaaac tgttgggtac caaaaatgag tattactccc attttggaaa atcatgaata     10440
gctgtattag ttgactttaa ctactgtgag taaatgcccg aggaaataaa aagcagaaaa     10500
atgagagcca agaggatctg tagcttctgc acccgtgcgt ggtgaggcag ggcaccatgg     10560
cgggagcatg tgggaaaagc cgcactttct ggtagacagg tggcaagggg tgccgggcag     10620
gggccctgga caagatgcat tcttcaaagc acatctccag tgactcactt ctcccagaga     10680
gggtacagtt ctcagttgct ccttctgtat gaactcaatg tgctgccagt ggtgacgcca     10740
ggactcgaag gatgtggtca ccaggtcccg cagggtgtgg tcacctctaa agactgtcac     10800
cagctggtgt ccaagcctgc aacctgtcag cctcatggtc tggctcccca gactgtccag     10860
tgactgaggc catttgcaga tggttttcag ttcccttgcc actgatttga acaggattcc     10920
catgattttg acttcaaagc attttatgt tggatttgct taagaaatcc ccatttctct     10980 tttcttttc aggttactgt ggactttgtg aagccatcga aagttgggac tttcaaaaaa     11040
```

```
ttgaaaagtt agaggaacac agattacttt taagacgttt agaaccagaa tttaaggcca   11100
cagttgatcc aaatgatatc ctttctgaac tatccgaatg tttgattaat caggaatgtg   11160
aagaaatcag acaggtaaac caatgccagg tactaaattt gaagaaaaat gcagagacat   11220
tggaaatgcc cattttttctg tcttgtttta ggcccaagga taattgaaac ccataaaagc   11280
tctcatctag cagatataat gactagaata gaattttaa agtgaatggg gtaattttg    11340 tgctagacta ttagaaaatt atttaaccta tttgcagtta aagttgcccc cttactttaa   11400
aaaaaatagt ggtttatgca taatgcaaat cacaccaaac agtgcaacaa ttaaaaggaa   11460
aaatatgtca ggctcttggg catagataca tttattacag tctcgcagtc acttaactag   11520
tgatgtgatg ccaggcagtt ctctaagcat ctgtggggtt tttgttgttg ttgttgttgt   11580
tgtttgtttg tttgtttttc atgtctaaag taagaaaatt tatcttttgt tttttgtttt   11640 tttgttttt tagatttctt tatttatt tattatatgt gagtacactg tagctgtctt     11700
cagacactcc agaagagggc gtcagatctt gttacggatg gttgtgagcc actatgtggt   11760
tgctgggatt tgaactcagg accttcggaa gaacagtcgg tgctctcaac ccctgagcca   11820
tctctccagc cccctttgt ttttgttttt gttttgttt ttgtttttt gttgtttgg      11880 ttttttgtc gttgttgttg tttgtttgtt ttgttttttc gagatagggt ttctctgtgt   11940
agccctggct gtcctggaac tcactctgta gaccaggctg ccttgaact cagaaatccg    12000 cctgcctctg cctcccgagt actgggatta aaggcatgca ccaccacgcc cgacgaaaat   12060
gtaccttatt agcactcttt tagggctaaa tgagaggtca tgcacaaaat gtgtatgtca   12120
gcttgatgca tagcagtcta tgcacaatgc atttcagtta tcattagaaa gaaaagtcat   12180
agaacatctg cttagaaaag agacctgctg ctgtgctgtt aggcatttcc aaatggctct   12240
gtgtgccgat acatccttag ggtgaatggt tagcgtctgg gttaacgctt ttaccccagg   12300
attgctcttg gtcagggata taaggattca gaagatgaga acatttgcct tggcatattg   12360
ataacacatt ataaaggaca aaggtgaaga aaggaatatc ttaaaagcta gtgctggaca   12420
gggcaaaaag atgatgctaa ctaagcccta ctcaactata cttcacagtg atttcaatca   12480
gataccgctt ccacaaaagc ttgccagagg aaaggctgag ctgcctgatc agtgtgctgc   12540
atttgtctcc cccagatccg agacactaaa gggagaatgg caggtgcgga gaagatggcc   12600
gaatgtctta tcagatccga caaggaaaac tggccaaagg tcttgcaact tgctttggag   12660
aaagacaaca gcaagtttag tgaattgtgg attgttgata aggtggggt gctccaagaa   12720 agaaccctgg accctgctgc gctcctccca gttctcccca ctttactttc catcagaggc   12780
gctgttcact tcagatacca aaggctatat ccctaggata caagcagtgg aaagctgaat   12840
tctgggagga agggaactac atggcatgga attaacccga ccaggtcaaa gaatctaggg   12900
aaggcttcca gccccaattt gttatcagag aaatagcttg agaattctag acctaaaggt   12960
tcaaactgca agacttacct ccctatcaga gcagaggctg agtgttgggg gtgatagcta   13020
tggactggtg ctcttgcccg gaagccatct ggactccgac agagcaagag taaacgaaga   13080
ttttctgtgt ttaagccaac ctcatttggc ttccggaaac tcacttcttg ctttaaacag   13140
accttgataa atacctgagt ttctagtttc ctttctcacc tagatttcct tagaacataa   13200
attattccag aaactctcta catcgttggt cagagatgga atcctgtctc tttagtgtgc   13260
tcaggaatga cgcccctgcg ttattggcgt gagttccgga gtggggaggg gctccggatg   13320
caaactgctg agagccccgg gttccacact tggagtcgcg tagttccaga tgaaactgga   13380
```

```
attcaattgc caagttgagc ttcaaactca gaataatcct tgcagttgtt ttaagccgtc    13440 aaagtgggc tctctagatg gctcagtgga taaggttcct gccactgatc ctgaagaccc     13500
aaattcaacg tccagggcct acatgataga accaatcccc aaacagtgtc ctcatccctc    13560
ggcacactca ctgtgtcgtg tgtgacacac acagtaaaca aatccatttc aaaaataaat    13620
aaaatgttaa gaaagtgcaa gaccgtgatt gtaagagctc aacggaaatt tagatgttta    13680
gtgttagtgt taggactttt tgggacttcc ccaaccaaaa ccataatcac attgcgcatg    13740
cttttaatcc cagcactcag gaggcagagg caggtggatt tctgagttcg aggccagcct    13800
ggtctacaga gtgagttcca ggacagccag ggctatacag agaaaccctg cctcgaccac    13860 caccccttc caaaaaaaaa aaaaaagat tctaagctgt aagctgttat tgtgtttat       13920 gattgtttgc ttgcctgttt atcacaaagg tttcaaaagg gctgaaagca aggctgatga    13980
ggatgatgga gcggaggcgt ccagcatcca gattttcatt caggaagagc cagagtgtca    14040
gaatctcagt cagaatcccg ggcctccttc aggtaccaag catcgtttgc tctcatccat    14100
gatggtgtcc cccagcactt tgatgccctt tgaaaaaaag tcttttttaaa ggatgattaa   14160 gaaaagaaag aatttgtggg gcaatagga cttcataatt agaatccctg ctcctgtctt     14220
ccatggcctc tgcatggcct tcaacccctcc ccctcctctc ccctccctc cccctccctc    14280 cagtatgtat gccttcatct gtaccgtgtt cccagaactt cagtgtccat gacttctcaa    14340
agcagccttg ctctctaaag aacacttctg ctcactaagc aatggctttg agaatctggg    14400
ctgacagctg gttttcctcg gctgttttg atgatctgtt cttactttgt tccaagtggc     14460
tttgttttga attaggccat tcttgctgtc cttttttcttg ataaagtttc cacgattaag    14520
aaagaattca tggggctgga gagatagatg gttcagcgtt taagagcacc gactgttctt   14580
tcagagatcc cgagttcaat tcctagcaac cacatagtga ctccagcgtc tgggttaatg    14640
tttttacccc atctgtaatg ggctctggtg tactcttctg gtgtgtcaga ggacagcgac    14700
aatgtgtata ttcatataca ttaaataata aataaatctt caaagagaaa agaaggaagg    14760
aagaagtaac agagagagag agagagagag agagagagag agagagagag agagagagag    14820
agagaacaca ctttggccaa gatcccaaac ctcaaacagg ggcattgttg ctagagtcag    14880
aactcatgtc cactgaatgg cagttgcacc atgattcctt gtagcatgaa cccttcgata    14940
actttgtccc ctctatatta cagaagcgtc ttctaataat ttacacagcc cattgaaacc    15000
aagaaattac caactggagc ttgccctgcc tgccaagaaa gggaaaaata caataatatg    15060
tgccactact ggtaagtcag ttgctgtcac tcacagaact ctctggcttc gcttttttctt    15120 ccccctttgg gggctgtaaa aggaggagtt ttccccgtgg cccatgctgc ccatgggaga    15180
gctggtctag cagcttaagg aacctggaca gcgataagga gggagataag tgtcttcttt   15240 agtttgctttt tggttcttgc tacctgagtg cacgttactt aggaagtagc ttggcacttt   15300
tcagccattg tttaaactgt cattgttagt gcggaggagg gattattagt ttatttgtat    15360
cccagtggtc atagagaagc caaaataagt accattctgg aaaaacagct aacacaggtt    15420
atctgttggt ttttttttct tttctttttt tttcttttt cttccctact aaaaggttgt     15480
ggaaaaacct ttgtgtcgct tcttatatgt gaacaccatc ttaaaaaatt cccatgtgga    15540
caaaaaggga aagtggtctt cttcgctaac caaattcctg tctatgagca gcaggcaact    15600
gtgttctcac gatatttga aagacttggg tatgtactac tacaatcaat ctaactgctt     15660 tgattttgg ttttgtttt gtttatgttt gtatttaaa ttctagcccc tttggctggt       15720
tttgggggct tgttgtgtc tggttttggg ggctttgttg tgtctggttt tggggggcttt    15780
```

```
gttgtgtctg gttttggggg ctttgttgtg tgttttctga gacagtgtat cacgtagcct  15840
tgagttgtct ccaacccact gtgtagctga ggttggccta gaagagatga tcttcttgct  15900
tctacaagtg ctgagattac agtgtgcact ggcatgcctg gctgttctct gatttctttt  15960
cttttttttt tttttaagat ttatttattt attatatgta agtacactgt agctgtcttc  16020
agacactcca gaagagggca tcagatctca ttatgggtgg ttgtgagcca ccatgtggtt  16080
gctgggattt gaacttcgga ccttcggaag agcagtcagg tgctcttacc cactgagcca  16140
tctcaccagc cctctctgat tttcaaagct atgattaaag gaaaatcgcc atggacttaa  16200
cttttagagg tagttccttt gtgcaataac atttttggtt taactttacc agaaatgcta  16260
agccctcatg tcatgctctg acagttaatg aacttggtgg ccaaatttaa catgtaggcg  16320
atacacaggt catccttaat gatgttatac ttgattggct attactcttt tcaaaatcat  16380
ttctctctta atgacttgaa agaataaata cactgtgatc agctataacc tcttgcattt  16440
cctgactccc cggctttgtg tcaggcctgt gagaaagttc aaggtactac ccagttgtac  16500
tcttttgggc ttgggctgac ttctttaatt gctgctctga cctagacttc tactttgtct  16560
ccttgttcat tcacatcaag gttgatgata agggatttct gtcattcccc aggtacaaca  16620
ttgcgagcat ttctggggca acatctgata gcgtctcagt gcagcacatc attgaagaca  16680
atgatatcat catcctgaca ccccagattc ttgtgaacaa tctcaacaac ggagccatcc  16740
cctcgttgtc tgtcttcact ctgatgatat ttgatgagtg tcataacact agcaaaaacc  16800
acccatacaa tcagatcatg ttcagatacc tagaccacaa acttggagag tcacgggacc  16860
cactgcctca ggtatttcca atcttctaag aagaaccaca gtttttcaga gtcccactta  16920
gttgctcttt tgtagccaca tttgagcttg ccctcctcgg ggtctcagtc catcggtaca  16980
actcagtggt caatgttggt tcattcattt gaccaacagt tgtcccttgg tgtccagggt  17040
agatgccctt cacaaaaaac aaaatctagg ctgcttaagt ctcttgtatg agatgacatt  17100
gcatttatat ataatctaca cactttcctc ttgcatactt taaatcttct ctagattact  17160
gatattgtac agtatgatga aaattttata taaatagttc tagtactgta atttttaggg  17220
aataaaggtg ggaaattcat acatgtttag tacttatgaa gttttaaaaa atatttttga  17280
tccatggttg tatgaattca catttatata acctctggat ttggagggcc agctgtataa  17340
accatgggct tccatggacc ttgtgcattg ttctaggctc tgggacacca atacagaaga  17400
tatagtcctg gctctcatac agttaagttt gcagggagcc aggaacatag tagtcacagc  17460
ttatcatgag gtatgctgca gagacaggta aagggtgttg tcagaacata aggggtaata  17520
aggcatagaa atgaagggaa ctgacagggg cttgccaggt agatagcttc tggtttctag  17580
taagagggtg ctgtgtgtcc aggggctcag ggaaatggaa gggcctgaca tgccccagaa  17640
ccttaaaact ctacagtatc acttgagggt agagtgtgaa gcagggaaca acagtcaagc  17700
tgattgttat gacagatgac ccagagacac caggagggca gagcgtcagt gggcaagtgg  17760
atggcttagc acagggaaca agcagcagcc ttctgatgtc atatgagaag agtcacttca  17820
gagtcattct tacatgtgac aagaggagta caaattctcc ttctgtctat cataggagag  17880
ggggtgcttt gctgaaagtc aacgatatag aaacaggagg gggctagaga ggatgaggac  17940
ggtttgactc aggcactgat agatgcaata aagaatgacg gtagtgtatc tatcaggggc  18000
cccaagaagc tgtaaaccat gaattatata caattctttt gctccaacaa taacctttttt  18060
aggacgtgca ggttaaagga catttagtac aggacccaca gtttgttatt ctcgagtatc  18120
```

```
gttgctagga agcagatttc ttaccgtcca gctaatcatt taggtgaatg cttactgaag    18180
ggtgttatca tactgaatct acacagctct cttgtacacg actcactgat tgttgaaggt    18240
atttgtccag gcgcacaaaa tgcatgtgat atgaatgagc ctggaatgga cttttcttc     18300 ccattgtgat gtttagtaag agactggggg ataaaaaaaa cagggtagcc ctgcctggaa    18360
aggtttcctc tctgttctgg atgacacgct agatttattt ccgagctttg ctccagggg     18420 gtctttgtgc tggagaatgt cagagagcca gtggtggggt gctccttaca ggtcgttggg    18480
ctgactgcct ccgtcggcgt tggagatgct aagaccgcgg aggaagccat gcaacatatc    18540
tgtaaactct gtgccgccct ggatgcctcc gtgattgcca cagtcagaga caacgttgca    18600
gaactggaac aggtcgttta taagccccag aaaagtaagt ggaggtcagc agcccacacc    18660
tcgcgacttt gtaaccttct gtcccctctg cgtcagagac agtggatgaa gtttgatgct    18720
gtatttgttt ggtaaaagca tagtggttac attgcctatc tttctcccta gtcaacctct    18780
tctccctagc gacgcatgag tctcaaaggt agccagaaag ggacaaacat ccctactctt    18840
taccagcagc tgagtgaagg aggcagtggg aagattcaag cattttgaaa gcctcaatag    18900
ctagtggcgg aatcaggtct ctgtgctccg ggccctaggc aggggctatg tggccatctt    18960
gttcttgtat gtatctgatc attgtagtgg catgacccga atcatgacag ttcaaaaggc    19020
cagaacatgt ttttaaaatg agcttcatta gaagatggtt attacttatt aactacctgt    19080
gtaagcaggg aggtaccgta gttacccacg gctggatctt ggcctgagca ctcgttctgt    19140
gagttgacag caggatcaat ggcagggtca atggcaggat gagcaatggg ggggtggggg    19200
ttgggatggc acaaccctgg ttcttttctga gagtcccccg tggagagtgt gaagaaggtg    19260
cctccccacc cacgcccacc ccttagcaac actcaagggt ttttctacag tttgagccct    19320
tggagcttag tctacttcaa agtcattttg tgtcactttc tccgtctatg caaaccctct    19380
acgagctatt ctgagggtgt gtcccagctc ctgcgcgcct tccttttcc cttattattc     19440 atcttgcggc agcttccccg gagagaatga ggtttcctcc cctctttgag agatgccttc    19500
ctggcctgca cctgcttccc agggctctga tgggcgggtt taggagcaca cctttgtttc    19560 cttttaaggag tgggtgggtt ggggagcagg gggagggggg agggagggga tagggggttt    19620
ttggagggga aaccaggaaa gggaataaca tttgaaatgt aaataacgaa aatatcttta    19680
aagaaaagaa aagaaaagga aagaaagaaa gaacctgcct tctgtgcagc atagggtagc    19740
tcttgtcagc tctctgtcac tgaaacagga catgtgacag gcagttcttt ttctgccaaa    19800
agtacacaaa tgtgaacgat aagctcaatg ggggcactct tgggggctcg gaggtgcgca    19860
ggagaatagg aaatcaggaa aacggggctg gagtatggta tttgccgaaa ccagaaggct    19920
gccagacctg ccacagtaga ggcaccagga aagctgactg agacgctggc ttagactaga    19980
ccaggagaga cactagaatc agaagcagtt ccgaggtcag aggcttctga ccgcctgctg    20040
tgatttgggc cacgtgagct tggagcctgt ggctttaaag gacttaccca ggatggagca    20100
gcttcgggaa atggctgcat aggacctggg tttccttcag cttactcaca tgcctttgac    20160
cccagtttcc aggaaagtgg catcccggac ttcgaacacg tttaaatgca tcatctctca    20220
gctgatgaag gagacagaga gctagccaa ggatgtctcc gaggaacttg gtaagcctgt     20280
gccaagtcct ggagagagaa atctcatgtt tcctgtccct tccatttaga ggtactcatg    20340
gattgctcgt tagtgtcttc agttttgggt gagattatac tcagaggtgg actgacttat    20400
ttattcacac atatttcttt ctgtctctgt atcttcttta tctcttcatt cttttttgcc    20460
atcatttttt tctccattcc ttttaaaaa gatttatttt tatttgatat gtgtagatgt     20520
```

-continued

```
ttttgtctgc atgtatgtat gtatatcaca tgtatcagat acccgggaac tggagttaca    20580
gacagttgtg agctaccaca tctgctggga atcgaaccca tgtcctctag aagggtagct    20640
ggtgcgcata accactgagg agcccccatt tctctagctg ttttttaagac aaggtttttt   20700
tccctgtgtc cctggttggc ctgaaacttg ctatgaagac aaggctggct ttgaacttgc    20760
aggggtcccc ttgcttcagc ttctgagtcc tggggtctct ggcaagcgcc accatacctg    20820
gctcagatat agactttctt aatcctaggt tgtttaggaa ccttatagga gttctttaat    20880
tctctcttgc cttttctttt ttaaatacaa aacacatcca cctggacata catacctgag    20940
aaaatactgtc tttaaatcat cttctaaatt tcctttcttc ctttttttcc cctcttgaga    21000
tagaatctct gtgttcagtg taggctggcc ttgaactggg aactctgccc ctcctcctcc    21060
tcctcctcct cccaagatgt gcatcatcac tgagctgcca ttagagtgcc attgtccctt    21120
ccaagagcag ttcccccagt gacctaacac tctctcactg tcctcagctc ttgaaagtgt    21180
caccacctcc taacctcaca cactgaggac caaccagcct tttgccacat gagcatccag    21240
aaggcactta gacagtagct aaggcacagc actgggggag gagtttgaat aatgaatcca    21300
ctatgggtcc taaagtagta gggtagcaag catgctctct cctctagagt tttgaaaact    21360
ctctgtaagg taaagagtaa agagaccagg tagtcagtac atggctcacc taggaacaag    21420
ataacatggt ctgactaaag tggtggatgg acagacggac aggaatagag ttgtatgact    21480
tactttttg ttttgttttt gtttttaaaa cagtctgtct gtatagctct gactgtcctg    21540
gaactctctt tgctggcctc aaactcacag agatctgcct gcctctgcct ccggaggcat    21600
tcacacttta gaatcttttc ccacctcctc acattgagta tctgtcaata gctgcctcac    21660
ttcttctgga acttggacgt ttttcattgt gaactgggtg tggtggcacc atctctactc    21720
ccagcagctg ggagcctgag tctgaggcca gcttaggcta catactgagc tcctgtcctt    21780
ggggcggagg ctgggaagaa cttgtcactg tttcttgttg gtacccgtcc tgtgttctgt    21840
tattgcaaat gtgagggaag ccatttaaca cacaaatgca tttcacttct ttgaactgta    21900
ctgtgcttgt ctcaagaagc ccaggacaca aaacaataga gcaagcatct ggggctgttc    21960
ccacttcgcc tttccccccc tacccacacc aatcttcccc tgagtctgaa tcgctgtgaa    22020
tcccacagta gaaccaagca gtcaagacat gcacatgcgc acacagatgc ttccgggata    22080
actgtgtttg actccgcctt gtggttggtg ctgcaagtgc tgctctgaga tcaggtgttt    22140
gggcttcata gcaacataga gcatgctggg aagggtcctg gtgctcccat ttttatataa    22200
ctgtctccga tgaagctctt gagacgtgct actctaatgg tatcttcatt ttgaaaggca    22260
aagtgtgtcc ctccttctct tcctcctcct ccttcttcct tacccctctt cttcgttctc    22320
tgttatttct gaactacttt ggctgtcagc cccttaagcc tgcagagcat agacaccaca    22380
gagctaggct tgaattcttg cctcacccac acaatatgag ctttatgaca ttgggggtaa    22440
attagttttc cttttataga agatttattt acttaaaaaa aaattatgtg catgtgcatg    22500
tgcgggatgg tgttgttgcc tccaggggtc agaagagggc gctgaatgcc ctggaactgg    22560
atttacaggt cgttggaagc cacccaatgt gagtgcaggg aactgaactt gggtcctcta    22620
caagggccta actattgagc caccacttct gctccttact caatctttct gaatctgttt    22680
cctcttttttt ttttttaaag atttattttat ttattatatg taagtacact gtagctaagc    22740
tatcttcaga cactccagaa gagggagtcg gatcttgtta cggatggttg tgaaccacca    22800
tgtggttgct gggacttgaa ctcaggacct ttggaagaac agtcggtgtt cttatccact    22860
```

```
gagccatctc tccagcctgt ttcctctttta aaaaaaaaaa ttaaataatg acctcatgaa   22920
attagaaaat ttcaatgcaa ttatgaagct tgattttggg tcatttagta aatagttatt   22980
ttacacactc ctcccccca cccccgcgc acgcacacag gcacacacac acacacacac   23040
acacacacac acacacacac acatagctta agacccagtc tacttcagga taaacatctt   23100
tcttataatg aataagaaag aaaatcagag gaccggtgct tgcaaatctt ttatttatct   23160
atttatgttc ttaccctgta ggaaagcttt ttcaaattca aaacagagaa ttcggcaccc   23220
agaaatatga acagtggatt gtcggcgtcc acaaagcgtg ctcagtgttt cagatggcag   23280
acaaagagga ggagagccgg gtctgcaaag cgctcttcct gtacacatca catttgcggg   23340
tacattgctg ctctccaggg cttattctca tcaccgcgcc tcctgggatc tgtactgagg   23400
cagctgagag aacatcagcg tctcaagtct aagagcttag tgaggaactt ttcccgaaag   23460
tcatcactaa ccttatttgt tttctgaaac ttatcatcaa gtctccaaaa actggattaa   23520
aggctcagag tctatgccac acctccctcc agcttgtgac tggtgaccac catctaactg   23580
agctcaaaaa agtggctcct gtggccatat cctgaagctt tcgtggtctt aattttgtta   23640
taaagtcata tattgaaatc tcaggggctc tggttaacac agagggaagg agtaactgta   23700
agagccctca gctctgtttg ctatgctctg ggaactattt aaagacttac tccacaccat   23760
gggattgtgg gatctaacgc ttaatggact ttcagcatag gtggtaaggg ccatcgttat   23820
gcaaggccca tgtacacttt aagtatgact tggaatttaa ggggaatgtc aaagctaact   23880
tgcttttgtt attgtttctc aagatatgct gtttctcctc tcccaaggtg gagttttata   23940
atccaaagtg aatctacttt taattttcta gctgagccaa aaatagaagc cagcttttgg   24000
ttcagaggtt tttattgtag acccactaag ggccattcgc cattaaaccc tcagctgtac   24060
tgtatgagaa agattttctg caaaccagtt ttgtgctaaa tacagcgagt tgaacttgag   24120
tgtagtgacc atatgcgacc tcagaaatgt attgagaatc acttttcatt tcaaacagaa   24180
atacaacgat gcactcatca tcagtgagga tgcacagatg acagacgctc taaattacct   24240
caaagccttc ttccacgatg tccgagaagc agcattcgat gagaccgagc gagagcttac   24300
tcggaggttt gaaggtgagg gagatttctg aagtcaggag tccctggggt ctggtggctt   24360
ttgtggcagt gtgcacatcg tagttagcat acgtagccat catgttgggt ttaaggtgag   24420
atttgtaggg gctgtgacgg agcatgacct tagcatggct gaaatcccca gcactaaaaa   24480
acgaacctat gctgaaactt tagagccaac caaccgacaa caggagggtt tggcttcaga   24540
gaaatctaat gcctgtggat ggatctgatg cttgccccac ttttcacttg ggaaaatggg   24600
aaacagtggg atttggaaag ggtgcttcct ctaggtggta ggtagtgcta ttctgattaa   24660
ctcagtaatt cagaaggttt aataacaaca gctcgtgtct gatggtgtca agattgtgct   24720
gtatgtatgt ccttccttcc ttccttcctt ccttccttcc ttccttcctt ccttccttcc   24780
ttccttcctt cctccctccc tccctccctc cctcccccct ttctcttctc ttctcttctc   24840
ttctcttctc ttctcttctc ttctcttctc ttctcttctc ttctcttctc ttctcttctc   24900
cttctcttct tcctcctcct tcatcttctt cttcttcct cctcttcctt ctccttcttc   24960
ttcaaaacac agtctgtata gcccggctg tcctgaaact cactttgtac accaggctgg   25020
cctcgaactc agaaatctgc ctgcctctgc ctcctgagtg ctgggattaa aggcgtgtgc   25080
caccatgccc agtttgtgca catatatgtg catatgttta ttataaattt tactgataca   25140
ggagatggca tagcacaaaa cacacaaata ataaacacgg agttcatgtt ccacagaatg   25200
cctttggagg tcttttcagt acccttgtgt ccagagccaa ccagagacag caattaccca   25260
```

```
atatggagtt ctgaaatgaa agtcagtttt atttcctgtt aatggcagaa ataagaacaa    25320
aacgaaacag cagaagcatt ttggaagctt gcttgtttct cagtgatggg agcaacattt    25380
ttctgagcca gataatagtt tttcaaacac gggtgggaca tttctgcatt tttacgtgat    25440
gcataaacag tagctaaatt taatccccat tatatactta gcactttaca aagtctagcc    25500
agacaataaa ggatgaagca agtgctatct tcatttccat ggtatgggta cttctaggat    25560
caccaatctc caaccatcac catgttgctg aacttgtgta aaattgagca gtaacacaca    25620
ctgacatttc taccattcat acactacagg taagtacaca ctcaagagcg tagataatag    25680
taaactgtaa taaaatgagt taggaaatta ataagcgtgg ctatttgtta catttgtttt    25740
tagtcattga gctgcaagca taaagagttg aaattttaat aatagttata tttaaaacca    25800
ggtccacaag tctgaagaac ttaataactg accataatct ggtttgatct ggttctatct    25860
agtacaccac cagtgtgtgt gtgcgtgtgt gctcctatgc atacttatac attaaaaaaa    25920
aaaaagatat cctatgcttc aattttaac ataaaataac cttctgacag ctgggtggtg    25980
gtggtggtgc atgtctttaa ttgcagcact caggaggcag gggcaggtgg gtctctgggt    26040
tcaaggccag tctggtttac agagccagtt ctaggacagc cagggctaca cagagaaacc    26100
ttgtttcaag acaaaacgaa acaaaacaac cacaaataaa aatatatct ttttgatgtt    26160 tccaaatcag caggtgtata taactcttta actttaatag taacagtgta tttacctcag    26220
tttggtagcc tgggatccat tgagctgttt ctcactaagc agtgttttgg ttgttggttt    26280
tttttttttt tttttttttt ttttgtattt agttcatagt ttcaacactg attgtccttg    26340
gaatcttctt cagagttttt tttttttttt tttttaaag atttatttat ttattatttt    26400
atttaagtac actttagctg acttcagaca caccagaaga gggtgtcaga tctcattacg    26460
gatgttagtg agccaccatg tggttgctgg gatttgaact ctggaccttc ggaagaacag    26520
tcggtgctct taaccactga gccatctctc cagccccaga gttttctaaa tagaactatg    26580
agtcaattcc tatctgtgga ttgctgtatc aaagaacatg tgagttttgt attgctgcgc    26640
tgcttttcta aagggattc ctgatgaaac gagtgtttac tgctctgatc tctggtgaac    26700
agtggaaagg ttaaccgaaa tagaaggcca ctgtttgttc taaagcttta acatttgtaa    26760
gccttttgca aaatgctctc tatttgcaga aaaactagag gaattagaaa aagtttccag    26820
ggatcccagc aatgagaatc ctaaactaag agacctctac ttggtcttac aagaagagta    26880
ccacttaaag ccagagacca agaccattct cttcgtgaag accagagcac tcgtggatgt    26940
aagtgtgtgt gtttacagat tagctctagt ttattgaaaa ggttgcccgt tcttcactgc    27000
cttataatca agtatccata catgtgtgga cctgttctga tgatttgttc ttacaccaat    27060
tgtcattgtt tgtattgacc cacagttata agtcttggtc ctatagagga agccctgcat    27120 ccttttttaaa aatttaaaat ttccacttcc agtcatcctg taggttttga ttaatgacta    27180
atgtgtctta tatcctcac agttatcttc atatcatctt ttaaaaataa tttactcaga    27240
ttttaaaaac cagttttaaa attgggcaat gggctggaga tacagctcaa tggtcaaatg    27300
cttgttcagc atgcatgact ttaatcccca gttctggaaa aagatagata tctctctgtt    27360
tatgtagaat gccttgagtc tggccacagc gcctccctct gtttatgtag aatgcctgca    27420
ttgtttctgc tgagtagtag attacccata gagccagagg cagaaaaagt caagctttat    27480
tattttatga gatccgtgga tcaggatctg gaaaggactg gatacttatg cctcaaggtc    27540
tcctgaggcc acagtcagct cggcactcaa ggctgacctc tcggctcctt ttgcaggttg    27600
```

```
ttggcaggct tgtgaagatg agcctccaac atggcagctg cccctgccta cagtgagatg    27660
agagactgag gagaagaggg cctagtagac agacactgcc attttataaa gtccatcttg    27720
gacctgatgt cccaccacat ctcccatatt tcagagataa actacagatt attttagaa     27780 tataggatgt agaagtcatt aagggtcgct tgtcatgtga tctttgctgt cttcttttgt    27840
taatgaatgt gggtgtttac catgtgcgtg tcgtgcccac agagtccagg aaggggggcat   27900 gacatgccct ggaactggag ttaacagaca gttgtaagtt gccatgtagg tgctgggaat    27960
tgaactcagg tcctctggaa gaacaaccag tgctcttaac caccgagcca tctctccagc    28020
cccctttgct gtgttttatt agcattttgt cattttagt atagaggtcc tgcatacatt     28080
ttgttagatt catacctagg tattaatttt agtgttgtca ttccgaaatt gtactttcaa    28140
atatttctca ctgtgggcta ggaagacatc tcagtaaagt gtctaaagta caggcatcag    28200
gacctggctt ccagcaacct ggtaaaaaag ccgagtacag tagagtactc ttgtaatccc    28260
agccctgggg acagagataa gcacaaccct aactggcaat gcccaggtcc cagggagtta    28320
ctcattactc agtcttaggc agaacgaagg tgggtggctg ttaagaaatg atacctaggg    28380
ctggtgagat ggctcagtgg gtaagagcac ctgactgctc ttccgaaggt ccagagttca    28440
aatcccagca accacatggt ggctcacaac catccgtaac gagatctgac tccctcttct    28500
ggtgtgtctg aagacagcta cagtgtactt acatataata aataaataaa tctttaaaaa    28560
aaaaaaaaaa aaaaagaaa tgatacctga ggttgacctc cacatgcatg tacacacaca    28620
cacacacaca cacatgcgtg cgtggacata ctcccctcca acacagtcag ccatgtacac    28680
ctccacacaa cacacagttc ttccaattgc agctgtctgc tgatatttac tgtgtaatta    28740
atttacatgg attgatcttt caccttaaag ccttgctaaa tttcacttac tctatgtctg    28800
aagcttgtct ttttaatcac ttaaaatatc tcctacatta agccataatg aggcagagtt    28860
ctatatcact agcatcaatt gttgtttgga atttaggatt tgccagtctg aaatccattt    28920
ttatctttag ttgtattctc tttttgcata tacatccatt atatcaaatt gatgtgaggt    28980
ttaaagttta caagtggtgt ctaactggcc gttgcttttc acttttaggc tctgaagaaa    29040
tggattgaag aaaatcctgc actaagcttt ctaaagcctg gcatactgac tgggcgtggc    29100
agaacaaacc gggcaacagg tatttatgtc tattgaatta gatttagtat actatgtata    29160
taaaatgtat aaacactaca ttgttttagt gtttctatca gtcagagctc aaccagagaa    29220
ataaagctac tagattatgc atatgtatgt ggtatatatg taagtatgta tgcttatttg    29280
tttgtttgtt tatttatgta cttagagata gggtttctct gtgtaaccct tgctctcctg    29340
gaactcactc tgtggaccag gctggccttg aattcagaaa tccgcctgcc tctgcctccc    29400
gagtgctggg attaaaggtg tgcgccacca ctgcctggcc tatactgtta ttctttaccc    29460
agtagatttt ttttcccat ctactgcctc tttaatagtt ttaaaaaaac agtccaggca    29520
atcctgaact ctagctagtg tggtctaggg aggaaggtta tcatttccca taagaacccct  29580 atgtggctag ctctcatcac agctacgtcc caagtcatat ctcacgactg tatgacctgc    29640
cctcgctgtt cttcctgcca gtgttgttta cactaaacaa gtctccaccc cttctctctc    29700
cgtcctcagg cattgctctt gtactttttcc attgtggaat ttcccgatct cataaacata    29760
gaatggactc aagtgttgaa tgtgtggttt cgagtctaac actaccctaa tgtggctgga    29820
ttttcaaagt tctttgccat ctctccaaca tgaatccaac ttgatttttca agctttgcta   29880 ctgacatata aatcgagcct tgaataatat tttgtgtgct catccatgca tgcatggatc    29940
catggatcca atcatgtgtc caaccactca tcccacccatc cgtgcatgca tccatctttc   30000
```

```
cgtcatgcat ttagacctta ctcagctcct gcttctgtga agaagcagcc atccctgtca   30060
tctaacaccc gaggtgcccc tcccccgcc acgttcccat cttacagatc tcaccccact    30120
tcctccacaa tggcttcctg ctcatcatcc ttatagataa agatggaatc tttaagcgtc   30180
atatttctac ctgctcagcc ataacccata attgctgacc gagtgttgga tggatgaatg   30240
aattggttag gatgattctg ctattgttgt tttctggatg attctttctt gttttatagc   30300
taacctggga aaaaggtgg acttttacaa aaagccacag gttgcttggt gtttggacat    30360
tttcagattc ccttatctgt agcatttta cttcctactt tgagacacat gttgtaatgt    30420
ttatgcctta ctatcttcat ctgtcaaatg aacaataaa tagttgtccc cagctcatag    30480
gttaacgaga atggtgaaac ctgagctttt tttttttttt tttttttttt tgtgaaaatg   30540
actttggcac ttttagatgg ttcaaaatta gtagccagtt tatgagtgag ttgtacagtg   30600
acctctttat ccaacacagg aatgacgctc ccggcacaga agtgtgtgct ggaggcattc   30660
agagccagcg gagataacaa tattctgatt gctacctcgg tcgctgatga aggcattgac   30720
attgctgagt gcaatctcgt cattctctat gagtacgtgg gcaacgtcat caagatgatc   30780
caaaccagag gtgagagcgg ctgatgtcat tcccgcccg cacccgcttt tctccttcc    30840 tcagctgtac catgtgattg acagcacagc tgactctggt actcgaaatc taaaagctga   30900
ctgccttggt caggattggg tggttatagg tttacccata atactccatt gcaactctcc   30960
acaatggtac tgcaattta cccagcgttc aatggcatag tcgtgaaaat atcatatcca    31020
ctaggccaga ggctttgcca gtcggcaagt agacctttga tgggtgtggt gagtagctct   31080
ctgtactcca gagtctggtc ccacctgaac cagagtctga cttcctttcc ctttcttgtt   31140
tccccaagaa cagcccccac attccctttc cggaataacg tctctgtgcc tgtcactcat   31200
cagtcacatc cattttcgt cctcctccac cgcttactgt gcggttcagc cagccagact    31260
ccgcttcctg ctcgtccagt ttctcagata ctgtcgctct acatgttagg tcctatctct   31320
gtctctgcca cacacaacct aattcttcta cctagaacaa gcactccttt aaatgcccac   31380
taccgtttat atctgtctct gcaagagcat gacaattgca ttcctttctc cgcattgcag   31440
aagggtcagg tgcgcgtgca cggtgccact gctgcgggct catgccagat tatctgtaaa   31500
ttagtgttgc tggcagtgca gagcaatcag actatgccat ggagacccc atgaaaactg    31560 ccagagatgg cttatctgtg tgctgagcac actggctaga acctgcattt gagtctactc   31620
ttcggttcag cttccctaga aagtaggatg cagtgaatca agttgaact cgagaaatac    31680 tcctcacatc tctttccagt aacctcagag tttgacatta acacacaaag aaaacgtttt   31740
ctgcaggccg aggaagagca cgagatagca agtgcttcct cctgaccagc agcgctgacg   31800
tgattgaaaa agaaaaggcg aacatgatca aggaaaaaat aatgaatgaa tccatcttaa   31860
gactgcagac atgggatgaa atgaaatttg gaaagacggt aagtctcttt ttctgtgcta   31920
ctcttatgga atctgactag aaataacaaa tgaccatggt tggtcctgag tgtgtgtgtg   31980
tgtgtgtgtg tggtatgtgt ttgtggccat gtgcatttat ttatctttgt gtgctagttt   32040
tggccattca ataaccttt ctgttcgcat gtaggttcac cgcatacagg tgaatgaaaa    32100
actcctcaga gacagtcagc acaaaccaca acctgttcct gacaaagaaa acaagaaact   32160
gctgtgtgga aagtgcaaga attttgcgtg ctacacagct gacattcgag tggttgaggt   32220
gagtggccct ggtgatttag caccggttaa atcttaccat cttccggaga aatggttgta   32280
gcaagaacac tatgttgtgg ggtttcgagt gttgaccatg gtcctgtatt aagaaataaa   32340
```

```
atcctgctag gtggtggtgg cacacgcctt taatcccagt acttgggagg cagaggcagg    32400
cggatttctg agttcgaggc cagcctggtc tacagggtga gttccaggac agccagggct    32460
acacagagaa accctgtctt ggaaaaacca aaaaaaaaaa aaaaaaaaag aaataaaatc    32520
ctgcttctat gtgggaacca gaaaggctga tgttatttaa gtccaaaaca gaaaatggtg    32580
cttaacggcg agaagaggag gggggtctaa ttgtagctgc cccagacagt caggcaggat    32640
ggataaggtt tcccgttcca ctgcacagca gggtgaatac tgcttatagt ttctgattca    32700
ttacaactct tacaaagaat tagacgagag gaattcatag cttcagacat aaagagatga    32760
aaactgtcca ggcagaaggg aatgctaatt actctggcga gatcattaga tacttagaaa    32820
ttatcacact gcacacccta agtgaggaca actgtgtgct ttgaaagaca gtctcactca    32880
gaccaggctg gcttcaactt gagattcttc tgtgactcag cctccccagt gcagggactc    32940
taggcatgca ccaccactct ctccaaagag atagtttttc ccagtgcagg gatagaaaat    33000
gaaggctctg ctagatacag tgttatgtcc ttggttagtt ccaggagga ggaagggcta    33060 ggcataaaaa tctgtcattg atttcttagt tttaacaaat gtgcaactgc attcaaaatg    33120
gaactgggct aaaggcattt gcaaatcttc tgaggcatct ctgtaacttt actgtatgtc    33180
aaagattatg ccaaagaaat gttaaggctc tgattttgaa gtgtacatgg ttctagtata    33240
aacctgccag caaatgaatg gtaaagtggg aaaatactat gaatatgaaa ttataaagat    33300
gcttttgtta tggctacata caacatgagc agtgatatct ttgtcatgac caatgtgggt    33360
ccacctttcc taaggggaa aaaaggctaa tatataaaa tgacatattc tgctagtgaa    33420
ttctctcttc ctgttttgtt ttctaaactt ccttattgga acagagaatg cttttataat    33480
gaaaacaaaa cacctcattt taaaaatat aacacttgta ggttagcttt ctacttttc    33540 accccttaaa cttttttttt ttttttttga gacaggatct ctctctatag cactgggtat    33600
cttgaaactc attatatgga gattcccttg tccctgcctc ccaaacgctg ggacgtaaag    33660
gcatgtacca ttcacaagg tcttcttaaa acttttaact aaggcaaaaa acctccagag    33720
acgaatcttg cagtcatcat tcctgctacc gatggcgggg gcagatggct gtgctagcta    33780
ggggaggggt acagtcctta ttatgagtga catccacttt ctgagtctga ttctttagat    33840
gcagaaggtc ctttcagctc caaattcaag gcttctcctt cccagtggcc tggagaacga    33900
gatgcttggt ctgcgcttgc gtctgtaggg tacactcttt ttttttttaat tggatatttt    33960 ctttatttac ataaagaaca ccttcagttc ccctacactg gggcatctaa gccttcatag    34020
gaccaaggac ctctcttccc attgatgcat gacaaggcca tcctctgcaa cgcacgcagc    34080
tggagccatg tgtactcctt tgtggatggc ttagtcgctg ggagctcttg ggggactggt    34140
tggttgatat tgttttctc cctgtggggt tccttcagtt gtagggtact ctcttaagtc    34200
aagtctaagt ggggtctgtg gacagcatgg ctcctgagcc tgttcacaca cataccctgt    34260 gaccctggg tgtcaccagc cctgtgcttt ggtgccttcc tggcctctgg tgaacttgaa    34320
ctttgtatgt gaactcctct ttgcttctga gttggaaagc tgggtttcct cctttctcag    34380
gtgccagacg cccaggaaat gggtcctaat cggcctgggg aagactgtct atatagtttt    34440 ttttttcttcc aacttgtaaa ataaatggga tcccactcat tcctgacttt tagctactga    34500
gtggcttcta agtcattttc agacccgttt ctaacattgt gcgctccatc tcttcctcct    34560
agacgtccca ctacactgtc cttggagacg ctttttaagga gcgctttgtg tgtaagccac    34620
accctaaacc aaagatctat gacaattttg agaagaaagc aaagatattc tgcgccaaac    34680
agaactgtag ccacgactgg ggaatttttg tgagatacaa gacgttcgag attccagtca    34740
```

```
taaaaattga aagtttcgtc gtggaagata ttgtgagcgg agttcagaac cggcactcaa   34800
agtggaagga ctttcatttt gaaaggatac agttcgatcc tgcagaaatg tccgtatgac   34860
ctcaggcttc tccgtctcgt gccgcaggga gccgtgcctt aagcatggag ttgatgagcc   34920
aatgctttct tacccaagct tgcacaatcc tttcttacac aagcctgcac tgtgttgaat   34980
gccagataac ctgactggtt ggtttcaagc tggtgctgtc cacacaaagc acacacgcct   35040
gaactgcggc gccgaatagt ttcttcacca ataactcata gcgtagccct tggccatggt   35100
ggggaggggt taaacttgtc cctttttacac ttttcagaac tgcccgacag gaacgtgca    35160
gccactcggt acaccgagac gcatgatggc tggcgtgctg gaagggttcc cgttctctgt   35220
ctgctcgatc tgctgtaagc tgcctttgcc cttaatgaca gtgcccttaa gaacagtgac   35280
ttagttcttt ttcaggccac cagactgact gccagatccc ttctgtccct tctgtccctt   35340
gcactgattc ctttccggat ttgaccctgc caccctgtca ccctctgcag agtctcctgg   35400
tttctgtctc ttccttggtt tctttgctga ctcaaatttg gtagttgcaa ggttcagtat   35460
gcacacatat atatttaaaa tgacatataa tttaaaatgt aaaagactat agttgacagc   35520
tatgcttact gagatggtat ttctgttctg ttcattacta tacatcttac ccttgctctc   35580
atctgttctt ttaacttggg ccatttcccg tctttgaata gacatctcaa accctgtctg   35640
tatgtctgtc tgtttcccac ctgtttgaga cagggtctct ctgtagacca gaaactccat   35700
atgtagacta tgctggcctt gaactcacag atcccctgc ctctcaagtg ttgaaattaa    35760
aatctttcac catgcctggc tctagctatt ttcaataaag gctcatgttt aaagtttgaa   35820
ctacttccaa ttcattccct gacgtggctt gttgttgttg tttactttg gagacactgt    35880
tcctctctgt agccctggct gtgtagacca ggctgcccct tggtcacagag atctgccagc  35940
ttctgcctcc ggagcactga gattgaaggc ctgcatcacc atgcctggct tgcccttct    36000
tcttaaacat tatatattca aatggcattt ccgtgtttct tctcaaggtg tgccagtgct   36060
tcagagagct tagtttgggg ttcttcagat caagagacaa gtgtctgagc gctgttactg   36120
ccaacagagc aaagtactct tcagttcagg gaaggaacag tgctggtttt gtaggcagta   36180
cagtggtttt aacaccttcc tagaacttac ttgtaattca tcagttgtag accatcaatg   36240
gcctaaacca aactgcagag atcatctgac cacataactc cccttccagg acatttacat   36300
ttgaagacta tcccaagccc acccagagca cagtgggtta cccaaactcc ccaggtcaac   36360
cctggaggtc aacagtatga catgggatag cacaccactt ctcacagatg cctagagaaa   36420
ttacccagca acataactct ttggggaaaa acaccctata gggattaggc tttaattga    36480
tagaataggt agaaaaaaag atatgtagta gttcttgata gtggttactg gtaaaattct   36540
tagtgcaata aaatgaattt gccgagagct gactttctt tttttcttgt tttttgaga    36600
cagggtttct ctgtatagct ttggctgtcc tggaatgcac tctgtagtcc aggctggcct   36660
tcgaactcag aaatccgcct tcctctgcct cccaagtgtt gggattaaag gcgtgcgcca   36720
ccacgcctgg ctgagagctg actttcattt atgtctttta gtctatgttg cctttctttg   36780
ctgctacagt ttaagaactc tacagcttgt ataagatacc tactggaaat tatttgagaa   36840
aaaaaacttg taaacattac aataatttaa ttaattaaaa atttatgtat tttatgtata  36900
tgggtgtttt tttctgcaag tctgtgtgca cattagaaga gggcattgga tcctctctat   36960
tgttatagtt ttatgctgct gctgttgttg ctgtgtgtgt gtgtgtgtgt gtgtgctatg   37020
aattgaactc aggacctctg gaagagcagt cagtgctctt aactgctgag ctatctctcc   37080
```

-continued

```
agtcctggca atgataaatc agttgaagtg aaatagtcct cccccccctt tttttttttt    37140
gccaatgggg aaaagcagac taaatctgag accaaatgaa gttttgagtt gtacactgac    37200
ttaagccact gccaagcata ccctggaatg gagcaaaccc tgggttacta agtactgaat    37260
gaatacaaca ggaaggtttt gagagatggg aaaatgcttg tctttggact tccctgatgg    37320
aagttgcatc tggactctcc catgagcaca tcaccagtcc ccactagagt cctcacaggt    37380
tgccatccat gtgtccttt tgaggctgag atacaacttg ttctgcaacc acagaccttg     37440
ctgttttgtg gtcagtattg gtatcatagc attttcatcc tgacctggag ccttcagtca    37500
aaggcctcat tgtgcagtaa ggacgctgga ctcctgactc ctatacttaa aacagacttg    37560
gtaatttcaa acaagtcaac cagatgccag tatttctgca tgcatgtctt gtgggatggt    37620
gttgtgaggt cccctgacag atgcactgag tggccaggga gactttttgta cccttttcca   37680 ttttaacagc ccacgggtca ctgtgttgct tccatcatat taacatcaac ttgaaccagt    37740
ggttcctgaa acacttcagt tcattggacc ttgctaatta gcatcctgta aaaacccacc    37800
aacaaatatc aactagacag gtagaatcca agtgaactgt acactcctgg atcatgccag    37860
taactgtttt aataatacac cataaaatat aactacgact tcattttaca aatctgtgtt    37920
taataaacag gtacaggctt gttgggtgcg aacttttaaa actcctaata aaaatgccag    37980
ctatgattat ctttgtttat g                                              38001
```

<210> SEQ ID NO 12
<211> LENGTH: 3435
<212> TYPE: DNA
<213> ORGANISM: Rattus norvegicus
<220> FEATURE:
<221> NAME/KEY: CDS
<222> LOCATION: (370)..(1815)

<400> SEQUENCE: 12

```
cgtttgtagt gtcagccatc ccaattgcct gttccttctc tgtgggagtg gtgtctagac      60
agtccaggca gggtatgcta ggcaggtgcg ttttggttgc ctcagatcgc aacttgactc     120
cataacggtg accaaagaca aaagaaggaa accagattaa aaagaaccgg acacagaccc     180
ctgcagaatc tggagcggcc gtggttgggg gcggggctac gacggggcgg actcgggggc     240
gtgggagggc ggggccgggg cggggcccgg agccggctgc ggttgcggtc cctgcgccgg     300
cggtgaaggc gcagcggcgg cgagtggcta ttgcaagcgt ttggataatg tgagacctgg     360 gatgcaggg atg tcg act atc tgc ccc cca cca tct cct gct gtt gcc aag    411
           Met Ser Thr Ile Cys Pro Pro Pro Ser Pro Ala Val Ala Lys
             1               5                  10 aca gag att gct tta agt ggt gaa tca ccc ttg ttg gcg gct acc ttt      459
Thr Glu Ile Ala Leu Ser Gly Glu Ser Pro Leu Leu Ala Ala Thr Phe
 15                  20                  25                  30 gct tac tgg gat aat att ctt ggt cct aga gta agg cac att tgg gct      507
Ala Tyr Trp Asp Asn Ile Leu Gly Pro Arg Val Arg His Ile Trp Ala
                 35                  40                  45 cca aag aca gac caa gta ctc ctc agt gat gga gaa atc act ttt ctt      555
Pro Lys Thr Asp Gln Val Leu Leu Ser Asp Gly Glu Ile Thr Phe Leu
             50                  55                  60 gcc aac cac act ctg aat gga gaa att ctt cgg aat gcg gag agt ggg      603
Ala Asn His Thr Leu Asn Gly Glu Ile Leu Arg Asn Ala Glu Ser Gly
         65                  70                  75 gca ata gat gta aag ttt ttt gtc tta tct gaa aag ggc gtc att att      651
Ala Ile Asp Val Lys Phe Phe Val Leu Ser Glu Lys Gly Val Ile Ile
     80                  85                  90
```

```
gtt tca tta atc ttc gac ggg aac tgg aac gga gat cgg agc act tac      699
Val Ser Leu Ile Phe Asp Gly Asn Trp Asn Gly Asp Arg Ser Thr Tyr
 95             100                 105                 110 gga cta tca att ata ctg ccg cag acg gag ctg agt ttc tac ctc cca      747
Gly Leu Ser Ile Ile Leu Pro Gln Thr Glu Leu Ser Phe Tyr Leu Pro
            115                 120                 125 ctg cac aga gtg tgt gtt gac agg cta acg cac atc att cga aaa gga      795
Leu His Arg Val Cys Val Asp Arg Leu Thr His Ile Ile Arg Lys Gly
        130                 135                 140 agg ata tgg atg cac aag gaa aga caa gaa aat gtc cag aaa att gtc      843
Arg Ile Trp Met His Lys Glu Arg Gln Glu Asn Val Gln Lys Ile Val
    145                 150                 155 ttg gaa ggc acc gag agg atg gaa gat cag ggt cag agt atc atc cct      891
Leu Glu Gly Thr Glu Arg Met Glu Asp Gln Gly Gln Ser Ile Ile Pro
160                 165                 170 atg ctt act ggg gag gtc atc cct gtg atg gag ctg ctt gcg tct atg      939
Met Leu Thr Gly Glu Val Ile Pro Val Met Glu Leu Leu Ala Ser Met
175                 180                 185                 190 aga tca cac agt gtt cct gaa gac ctc gat ata gct gat aca gta ctc      987
Arg Ser His Ser Val Pro Glu Asp Leu Asp Ile Ala Asp Thr Val Leu
                195                 200                 205 aat gat gat gac att ggt gac agc tgt cat gaa ggc ttt ctt ctc aat     1035
Asn Asp Asp Asp Ile Gly Asp Ser Cys His Glu Gly Phe Leu Leu Asn
            210                 215                 220 gcc atc agc tca cat ctg cag acc tgc ggc tgt tct gtg gtg gta ggc     1083
Ala Ile Ser Ser His Leu Gln Thr Cys Gly Cys Ser Val Val Val Gly
        225                 230                 235 agc agt gca gag aaa gta aat aag ata gta aga aca ctg tgc ctt ttt     1131
Ser Ser Ala Glu Lys Val Asn Lys Ile Val Arg Thr Leu Cys Leu Phe
    240                 245                 250 ctg aca cca gca gag agg aag tgc tcc agg ctg tgt gaa gcc gaa tcg     1179
Leu Thr Pro Ala Glu Arg Lys Cys Ser Arg Leu Cys Glu Ala Glu Ser
255                 260                 265                 270 tcc ttt aaa tac gaa tct gga ctc ttt gta caa ggc ttg cta aag gat     1227
Ser Phe Lys Tyr Glu Ser Gly Leu Phe Val Gln Gly Leu Leu Lys Asp
                275                 280                 285 gcg act ggc agt ttt gta cta cct ttc cgg caa gtt atg tat gcc cct     1275
Ala Thr Gly Ser Phe Val Leu Pro Phe Arg Gln Val Met Tyr Ala Pro
            290                 295                 300 tat ccc acc aca cac atc gat gtg gat gtc aac act gtc aag cag atg     1323
Tyr Pro Thr Thr His Ile Asp Val Asp Val Asn Thr Val Lys Gln Met
        305                 310                 315 cca ccg tgt cat gaa cat att tat aat caa cgc aga tac atg agg tca     1371
Pro Pro Cys His Glu His Ile Tyr Asn Gln Arg Arg Tyr Met Arg Ser
    320                 325                 330 gag ctg aca gcc ttc tgg agg gca act tca gaa gag gac atg gct cag     1419
Glu Leu Thr Ala Phe Trp Arg Ala Thr Ser Glu Glu Asp Met Ala Gln
335                 340                 345                 350 gac acc atc atc tac aca gat gag agc ttc act cct gat ttg aat att     1467
Asp Thr Ile Ile Tyr Thr Asp Glu Ser Phe Thr Pro Asp Leu Asn Ile
                355                 360                 365 ttc caa gat gtc tta cac aga gac act cta gtg aaa gcc ttt ctg gat     1515
Phe Gln Asp Val Leu His Arg Asp Thr Leu Val Lys Ala Phe Leu Asp
            370                 375                 380 cag gtc ttc cat ttg aag cct ggc ctg tct ctc agg agt act ttc ctt     1563
Gln Val Phe His Leu Lys Pro Gly Leu Ser Leu Arg Ser Thr Phe Leu
        385                 390                 395 gca cag ttc ctc ctc att ctt cac aga aaa gcc ttg aca cta atc aag     1611
Ala Gln Phe Leu Leu Ile Leu His Arg Lys Ala Leu Thr Leu Ile Lys
    400                 405                 410
```

```
tac ata gag gat gac acg cag aag ggg aaa aag ccc ttt aag tct ctt      1659
Tyr Ile Glu Asp Asp Thr Gln Lys Gly Lys Lys Pro Phe Lys Ser Leu
415                 420                 425                 430 cgg aac ctg aag ata gat ctt gat tta aca gca gag ggc gac ctt aac      1707
Arg Asn Leu Lys Ile Asp Leu Asp Leu Thr Ala Glu Gly Asp Leu Asn
                435                 440                 445 ata ata atg gct cta gct gag aaa att aag cca ggc cta cac tct ttc      1755
Ile Ile Met Ala Leu Ala Glu Lys Ile Lys Pro Gly Leu His Ser Phe
            450                 455                 460 atc ttc ggg aga cct ttc tac act agt gtc caa gaa cgt gat gtt cta      1803
Ile Phe Gly Arg Pro Phe Tyr Thr Ser Val Gln Glu Arg Asp Val Leu
        465                 470                 475 atg act ttt taa acatgtggtt tgctccgtgt gtctcatgac agtcacactt          1855
Met Thr Phe
    480 gctgttacag tgtctcagcg ctttggacac atccttcctc cagggtcctg ccgcaggaca    1915 cgttacacta cacttgtcag tagaggtctg taccagatgt caggtacatc gttgtagtga    1975 atgtctcttt tcctagacta gatgtaccct cgtagggact tatgtttaca accctcctaa    2035 gtactagtgc tgtcttgtaa ggatacgaat gaagggatga aaacttcacc acaactgctg    2095 gttggttttg ttgtttttgt ttttgaaac ttataattca tggtttacat gcatcacact     2155 gaaaccctag ttagcttttt acaggtaagc tgtgagttga ctgcctgtcc ctgtgttctc    2215 tggcctgtac gatctgtggc gtgtaggatc acttttgcaa caactaaaaa ctaaagcact    2275 ttgtttgcag ttctacagaa agcaacttag tctgtctgca gattcgtttt tgaaagaaga    2335 catgagaaag cggagtttta ggtgaagtca gttgttggat cttcctttat agacttagtc    2395 ctttagatgt ggtctgtata gacatgccca accatcatgc atgggcactg aatatcgtga    2455 actgtggtat gcttttgtt ggtttattgt acttctgtca agaaagtgg cattggtttt      2515 tataattgtt gccaagtttt aaggttaatt ttcattattt ttgagccaaa ttaaaatgtg    2575 cacctcctgt gcctttccca atcttggaaa atataatttc ttggcagaag gtcagatttc    2635 agggcccagt cactttcgtc tgactttccct ttgcacagtc cgccatgggc ctggcttaga   2695 agttcttgta aactatgcca gagagtacat tcgctgataa aatcttcttt gcagagcagg    2755 agagcttctt gcctctttcc tttcatttct gcctggactt tggtgttctc cacgttccct    2815 gcatcctaag gacagcagga gaactctgac cccagtgcta tttctctagg tgctattgtg    2875 gcaaactcaa gcggtccgtc tctgtccctg taacgttcgt accttgctgg ctgtgaagta    2935 ctgactggta aagctccgtg ctacagcagt gtagggtata cacaaacaca gtaagtgtt    2995 ttatttaaaa ctgtggactt agcataaaaa gggagactat atttatttt tacaaagggg    3055 ataaaaatgg aacctttcc tcacccacca gatttagtca gaaaaaaaca ttctattctg    3115 aaaggtcaca gtggttttga catgacacat cagaacaacg cacactgtcc atgatggctt    3175 atgaactcca agtcactcca tcatggtaaa tgggtagatc cctccttcta gtgtgccaca    3235 ccattgcttc ccacagtaga atcttattta agtgctaagt gttgtctctg ctggtttact    3295 ctgttgtttt agagaatgta agttgtatag tgaataagtt attgaagcat gtgtaaacac    3355 tgttatacat cttttctcct agatggggaa tttggaataa aataccttta aaattcaaaa    3415 aaaaaaaaaa aaaaaaaaa                                                 3435

<210> SEQ ID NO 13
<211> LENGTH: 36
<212> TYPE: DNA
```

<213> ORGANISM: Homo sapiens

<400> SEQUENCE: 13
ggggccgggg ccggggccgg ggccggggcc ggggcc                                    36

<210> SEQ ID NO 14

<400> SEQUENCE: 14

000

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
tgtgacagtt ggaatgcagt ga                                                   22

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
gccacttaaa gcaatctctg tcttg                                                25

<210> SEQ ID NO 17
<211> LENGTH: 21
<212> TYPE: DNA
<213> ORGANISM: Artificial sequence
<220> FEATURE:
<223> OTHER INFORMATION: Probe

<400> SEQUENCE: 17
tcgactcttt gcccaccgcc a                                                    21

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gggtctagca agagcaggtg                                                      20

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
gtcttggcaa cagctggaga t                                                    21

<210> SEQ ID NO 20
<211> LENGTH: 24
<212> TYPE: DNA
<213> ORGANISM: Artificial sequence
<220> FEATURE:

```
<223> OTHER INFORMATION: Probe

<400> SEQUENCE: 20
tgatgtcgac tctttgccca ccgc                                              24

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
tcctgtaatg gaactgcttt ca                                                22

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
ggtatctgct tcatccagct tt                                                22

<210> SEQ ID NO 23
<211> LENGTH: 16
<212> TYPE: DNA
<213> ORGANISM: Artificial sequence
<220> FEATURE:
<223> OTHER INFORMATION: Probe

<400> SEQUENCE: 23
ccccggcccc ggcccc                                                       16

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
caagccaccg tctcactcaa                                                   20

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
gtagtgctgt ctactccaga gagttacc                                          28

<210> SEQ ID NO 26
<211> LENGTH: 28
<212> TYPE: DNA
<213> ORGANISM: Artificial sequence
<220> FEATURE:
<223> OTHER INFORMATION: Probe

<400> SEQUENCE: 26
gtagtgctgt ctactccaga gagttacc                                          28
```

```
<210> SEQ ID NO 27
<400> SEQUENCE: 27

000

<210> SEQ ID NO 28
<400> SEQUENCE: 28

000

<210> SEQ ID NO 29
<400> SEQUENCE: 29

000

<210> SEQ ID NO 30
<211> LENGTH: 20
<212> TYPE: DNA
<213> ORGANISM: Artificial sequence
<220> FEATURE:
<223> OTHER INFORMATION: Slynthetic oligonucleotide

<400> SEQUENCE: 30
agcgggacac cgtaggttac                                                   20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
gtgggcggaa cttgtcgctg                                                   20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
gtcacattat ccaaatgctc                                                   20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
ggtgggcaaa gagtcgacat                                                   20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
atctctgtct tggcaacagc                                                   20
```

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
aagcaatctc tgtcttggca                                          20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
acttaaagca atctctgtct                                          20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
ttgccactta aagcaatctc                                          20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
cccagtaagc aaaagtagct                                          20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
actctaggac caagaatatt                                          20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gccttactct aggaccaaga                                          20

<210> SEQ ID NO 41
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 41
ccaaatgtgc cttactctag                                          20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
tggagcccaa atgtgcctta                                          20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tctgtctttg gagcccaaat                                          20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ccatcactga gaagtacctg                                          20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
atttctccat cactgagaag                                          20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
aaaagttatt tctccatcac                                          20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
tggcaagaaa agttatttct                                          20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gtgtggttgg caagaaaagt                                          20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ctccatttag agtgtggttg                                          20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tgcatttcga aggatttctc                                          20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ccactctctg catttcgaag                                          20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
acaaaaaact ttacatctat                                          20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ccttttcaga caagacaaaa                                          20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
aagattaatg aaacaataat                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtttccatca aagattaatg                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
attgatagtc catatgtgct                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
agtataattg atagtccata                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggaggtagaa actaagttct                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
atgtgttaat ctatcaacac                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tgcatccata ttcttccttt                                               20

<210> SEQ ID NO 61
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 61
ttccttatgc atccatattc                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
cttgtctttc cttatgcatc                                               20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
acattttctt gtctttcctt                                               20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
tctggacatt ttcttgtctt                                               20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
ataatcttct ggacattttc                                               20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ctctgaccct gatcttccat                                               20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
```
ttggaataat actctgaccc                                          20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
cagttccatt acaggaatca                                          20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
cttcaggaac actgtgtgat                                          20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
atctatttct tcaggaacac                                          20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
agtactgtat cagctatatc                                          20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tcattgagta ctgtatcagc                                          20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
tcatcatcat tgagtactgt                                          20

<210> SEQ ID NO 74
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 74
ccaatatcat catcattgag                                                   20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
tcatgacagc tgtcaccaat                                                   20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
aagccttcat gacagctgtc                                                   20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
agaagaaagc cttcatgaca                                                   20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tacttgagaa gaaagccttc                                                   20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
attcttactt gagaagaaag                                                   20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
aaaaattctt acttgagaag                                                   20
```

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
agatggtatc tgcttcatcc                                                   20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
caatctaagt agacagtctg                                                   20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ttaagcaaca gttcaaatac                                                   20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctttaaatag caaatggaat                                                   20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gccatgattt cttgtctggg                                                   20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
gctttaatga gaagtaaaac                                                   20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 87
tctacagtac aacttaatat                                           20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
ataattttgt tctacgccta                                           20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
cactgctgga tggaaaaaga                                           20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
tggtttaagg gcacaaactc                                           20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
ttgcccacgg gtacacagca                                           20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
cagatgagga aataggtgta                                           20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
acacattagg tactattact                                           20

<210> SEQ ID NO 94
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
tttttatgtt ccaggcactg                                               20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
aataggaaat gttagctatg                                               20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
ggcactcaac aaatactggc                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
tacatgtaaa gcaactagta                                               20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
taaaatttca tgaaaatctg                                               20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
aagtgaatac tttatacttt                                               20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
```
catcatgagc ctaaaggaaa                                           20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
ggctcttagg ttaaacacac                                           20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
tgcttctgat tcaagccatt                                           20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
atacaggact aaagtgcttc                                           20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
caaatgggat ttaaaatgat                                           20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
tgacatgtag agagattaag                                           20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ttattgaaat accatcattt                                           20

<210> SEQ ID NO 107
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 107
tagtcagtat aatatcattt                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
gcattgagaa gaaagccttc                                              20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
aagacctgat ccaggaaggc                                              20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
tgagctgatg gcattgagaa                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
acaacggaac agccacaggt                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
ttagtgtcaa ggcttttctg                                              20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
gacggctgac acaccaagcg                                              20
```

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tgatggcatt gagaagaaag                                           20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
tttactttct ctgcactgct                                           20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
tcttatttac tttctctgca                                           20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ggcataatgt tctgactatc                                           20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
ataacctgga gcattttctc                                           20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
ccctgactca tatttaaatg                                           20

<210> SEQ ID NO 120
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 120
ccagttgaat cctttagcag                                           20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
catacatgac ttgccggaaa                                           20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gacatccaca tctatgtgtg                                           20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
tgttcatgac agggtggcat                                           20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
ttataaatat gttcatgaca                                           20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
cagctcggat ctcatgtatc                                           20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
ctccagaagg ctgtcagctc                                           20

```
<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
gtatcctgag ccatgtcttc                                                    20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
aatcaggagt aaagctttcg                                                    20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
aaaatattca aatcaggagt                                                    20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
tctctgtgta agacatcttg                                                    20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
gagtgtctct gtgtaagaca                                                    20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
cactagagtg tctctgtgta                                                    20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 133
gctttcacta gagtgtctct                                               20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
gatccaggaa ggctttcact                                               20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
aaagtacttc tgagagataa                                               20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
aactgtgcaa ggaaagtact                                               20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
gtcaaggctt ttctgtgaag                                               20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
agagatttaa agggctttt                                                20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
atcttcaggt tccgaagaga                                               20

<210> SEQ ID NO 140
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 140
ccctctgctg ttaaatcaag                                              20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
tgttaagatc gccctctgct                                              20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
attattatgt taagatcgcc                                              20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
agagccatta ttatgttaag                                              20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
ataaaagagt gtaggcctgg                                              20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
acactagtgt agaaaggtct                                              20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
```
gttcttgcac actagtgtag                                                     20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
taaaaagtca ttagaacatc                                                     20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
tattaagtta cacatttaaa                                                     20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
ctttaccagc gatcatgatt                                                     20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
ttctggagta tgatccaggg                                                     20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
acttaactgc aattgctgag                                                     20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
tgtagtgtaa cttacttaac                                                     20

<210> SEQ ID NO 153
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 153
atgcacctga catcccctca                                               20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
cccaaaagca taaatctagg                                               20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
atatttatta tattgtaaac                                               20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
agcaataata tttattatat                                               20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
agatagcaat aatatttatt                                               20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
aaagatagca ataatattta                                               20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159 ttaaagata gcaataatat                                                20
```

```
<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
atctttaaaa gatagcaata                                                      20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
atatctttaa aagatagcaa                                                      20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
attatatctt taaaagatag                                                      20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
tattattata tctttaaaag                                                      20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
caagtttaca tcctattatt                                                      20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
aaaacagtag ttgtggtcaa                                                      20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide
```

-continued

<400> SEQUENCE: 166
aaaaaacagt agttgtggtc                                                   20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
tgaatcatgt atttcaaaaa                                                   20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
gccaactcag atttcacctt                                                   20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
ctacacacca aagaatgcca                                                   20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
agttttcagt tgattgcaga                                                   20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
catcctatgt tcaagctcac                                                   20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
taaacatctg cttgatcaat                                                   20

<210> SEQ ID NO 173

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
aatccacaaa gtaggatcta                                               20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
attagacatt tctacagact                                               20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
ctcaactaca tagaatatca                                               20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
ttggcaacaa ttactaaaac                                               20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
tcaaaaataa tgaaaattaa                                               20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
caatttggct caaaaataat                                               20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
```
ggcacaggag gtgcacattt                                               20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
tagattttct aaggagaaaa                                               20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
actgaccagt gaaatctgaa                                               20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
ggtaagactt agcaagaaga                                               20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
tctcagagtt gcaatgattg                                               20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
agatcttatt agttagtata                                               20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
agtactcaag gaactatttt                                               20

<210> SEQ ID NO 186
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 186
ggcaaacagc aacaacttca					20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
gcacttcagt aaaatttctc					20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
ggtccaaacg cattaagaaa					20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
gaattatatt aatcagttat					20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
tgtgtttgtg taactacaat					20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
atattacttc cagaatttta					20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
ggcagaaggg ctctattacc					20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
cattcgaaca tgtcattttg         20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
ctgattcatg atgggaaagc         20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
gtggttgtct aaaacatcaa         20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
atgactgagc tacagtacaa         20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
gggacactac aaggtagtat         20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
ttaaataaga atctaccatg         20

<210> SEQ ID NO 199
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 199
gctttaataa cttatttcac                                           20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
aggagaaaag atatataaca                                           20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
ccatttagga gaaaagatat                                           20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
ttcaccctca gcgagtactg                                           20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
aggctgcggt tgtttccctc                                           20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
gccagatccc catcccttgt                                           20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
tcacttcctt taagcaagtc                                           20

```
<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
agtgatgccc aagtcacaat                                                    20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
agtcaagtga tgcccaagtc                                                    20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
ccatcagtca agtgatgccc                                                    20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
gattaccatc agtcaagtga                                                    20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
caactgatta ccatcagtca                                                    20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
gcagtttcca actgattcag                                                    20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 212
cgttcttgtt tcagatgtac    20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
gccaaacaaa atattttatc    20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
taggtaggct aacctagtcc    20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
tcccagccca aagagaagca    20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
ggatcatagc tctcggtaac    20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
aatcataaag ccctcacttc    20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
ctgattggta tttagaaagg    20

<210> SEQ ID NO 219
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 219
atgcagacat gattacatta                                              20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
ttcatcatta aactgaaaat                                              20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
cttttaggtt aaaaaggtgg                                              20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
atacagagcc tggcaaaaca                                              20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
ttctatttac agagcattag                                              20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
gccttcacat taattcacca                                              20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
tgtgttattg cccctaaaaa                                              20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
tgtattcact atactatgcc                                              20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
aagttattta aagtatagca                                              20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
gacattgaag tatcaagaca                                              20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
tgttaagtaa tcttagaaaa                                              20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
ggcatacatt tagaaattca                                              20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
accttatgca tccatattct                                              20

<210> SEQ ID NO 232
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 232
gaattctctt gggaaccatt                                                    20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
atattcaact acaggattta                                                    20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
atgtgttctt tagatacatc                                                    20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
ccttatacag atacatgctg                                                    20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
tagatgcaat tactattttc                                                    20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
tgtacttccc aaacttgaac                                                    20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
ctgaagctca acaacaccaa                                                    20
```

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
gtctatagaa tcaaactgaa                                              20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
ttgaatcaat acctaacctc                                              20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
tgcctctttt agaaaagatc                                              20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
atggaatcat tggtttatcg                                              20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
aaagctcact tttattcttt                                              20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
ggtgccgcca ccatgcccgg                                              20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
gagagaagct gggcaataaa                                              20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
tctgaccctg cacaataaag                                              20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
atagtgtgtg attcaaaacg                                              20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
actgtatcag ctatctaaaa                                              20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
ttatttgtat aggaacctac                                              20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
tgtgagctga tggcactgta                                              20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
ccttatttac tttctctgca                                              20

<210> SEQ ID NO 252

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
ggaataaggt cactagttcg                                          20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
atttgcaaca atttttaaat                                          20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
ataaactacc aatgatatcc                                          20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
tacctgatcc aggaaggctt                                          20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
ttcccgaagc ataaatctag                                          20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
ttgagaagca tgaaattcca                                          20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
```
gcgggacacc gtaggttacg                                               20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
ctttcctagc gggacaccgt                                               20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
gcacctctct ttcctagcgg                                               20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
tgtttgacgc acctctcttt                                               20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
cttgtcgctg tttgacgcac                                               20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
gggcggaact tgtcgctgtt                                               20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gcagcaggga cggctgacac                                               20

<210> SEQ ID NO 265
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 265
agaagcaacc gggcagcagg                                         20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
cccaaaagag aagcaaccgg                                         20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
accccgcccc caaaagagaa                                         20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cttgctagac cccgccccca                                         20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
cacctgctct tgctagaccc                                         20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
taaacccaca cctgctcttg                                         20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
ctcctaaacc cacacctgct                                         20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
acacacacct cctaaaccca                                                  20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
aaacaaaaac acacacctcc                                                  20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ggtgggaaaa acaaaaacac                                                  20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
ctgtgagagc aagtagtggg                                                  20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
agcgagtact gtgagagcaa                                                  20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
tcaccctcag cgagtactgt                                                  20

<210> SEQ ID NO 278
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 278
tcaggtcttt tcttgttcac                                           20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
aatctttatc aggtcttttc                                           20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
ttctggttaa tctttatcag                                           20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
ttgttttctt ctggttaatc                                           20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
ttccctcctt gttttcttct                                           20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
gcggttgttt ccctccttgt                                           20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
tacaggctgc ggttgtttcc                                           20

```
<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
gagcttgcta caggctgcgg                                                 20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
gagttccaga gcttgctaca                                                 20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
cgactcctga gttccagagc                                                 20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
cccggcccct agcgcgcgac                                                 20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
gccccggccc cggcccctag                                                 20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
accacgcccc ggccccggcc                                                 20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 291
ccgccccgac cacgccccgg                                                 20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
ccccgggccc gccccgacca                                                 20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
cgccccgggc ccgccccegg                                                 20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
cgcagccccg ccccgggccc                                                 20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
accgcaaccg cagccccgcc                                                 20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
gcgcaggcac cgcaaccgca                                                 20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
ggcgcaggca ccgcaaccgc                                                 20

<210> SEQ ID NO 298
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 298
cgcctccgcc gccgcgggcg                                               20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
accgcctgcg cctccgccgc                                               20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
cactcgccac cgcctgcgcc                                               20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
ccactcgcca ccgcctgcgc                                               20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
ggtccccggg aaggagacag                                               20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
aacaactggt gcatggcaac                                               20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
```

```
gtttcagatg tactatcagc                                           20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
aaggtgaagt tcatatcact                                           20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
ggtaacttca aactcttggg                                           20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
ggttcatgag aggtttccca                                           20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
tactgaattg cttagtttta                                           20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
ctaacagaat aagaaaaaaa                                           20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
gagcattaga tgagtgcttt                                           20

<210> SEQ ID NO 311
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 311
tgcattccta agcaatgtgt                                              20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
tctaggcctt cacattaatt                                              20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
cctgtctatg cctaggtgaa                                              20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
tagcacatac aattattaca                                              20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
gaggagaaga acataaacgc                                              20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
taccacaagt ctggagccat                                              20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
gatactggat tgttgaaact                                              20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
tagtatgact ggagatttgg                                              20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
atcaaaaccc caaatgattt                                              20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
atccaaatgc tccggagata                                              20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
tcgacatcac tgcattccaa                                              20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
caacagctgg agatggcggt                                              20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
atttgccact taaagcaatc                                              20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 324
gtacctgttc tgtctttgga                                                 20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
caagaaaagt tatttctcca                                                 20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
gaaggatttc tccatttaga                                                 20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
ttacatctat agcaccactc                                                 20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
tcactccctt ttcagacaag                                                 20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
agtttccatc aaagattaat                                                 20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
atagtccata tgtgctgcga                                                 20

<210> SEQ ID NO 331
```

-continued

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
aactaagttc tgtctgtgga                                         20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
caacacacac tctatgaagt                                         20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
ttcctttccg gattatatgt                                         20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
tttccattac aggaatcact                                         20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
atcagcctat atctatttcc                                         20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
tcaatgacca ggcggtcccc                                         20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337 cttttttatgg aaaaggaaaa                                              20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
tgtttcccca aaaatttctg                                              20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
agatatccac tcgccaccgc                                              20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
ccggccccgg ccccggcccc                                              20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
cccggccccg gccccggccc                                              20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
ccccggcccc ggccccggcc                                              20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
gccccggccc cggccccggc                                              20

<210> SEQ ID NO 344
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 344
ggccccggcc ccggccccgg                                              20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
cggccccggc cccggccccg                                              20

<210> SEQ ID NO 346
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 346
cggccccggc cccggcccc                                               19

<210> SEQ ID NO 347
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 347
ccggccccgg ccccggccc                                               19

<210> SEQ ID NO 348
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 348
cccggccccg gccccggcc                                               19

<210> SEQ ID NO 349
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 349
ccccggcccc ggccccggc                                               19

<210> SEQ ID NO 350
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 350
gccccggccc cggccccgg                                               19
```

<210> SEQ ID NO 351
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 351
ggccccggcc ccggcccg                                                  19

<210> SEQ ID NO 352
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 352
ggccccggcc ccggcccc                                                  18

<210> SEQ ID NO 353
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 353
cggccccggc cccggccc                                                  18

<210> SEQ ID NO 354
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 354
ccggccccgg ccccggcc                                                  18

<210> SEQ ID NO 355
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 355
cccggccccg gccccggc                                                  18

<210> SEQ ID NO 356
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 356
ccccggcccc ggccccgg                                                  18

<210> SEQ ID NO 357
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 357
gccccggccc cggcccg                                            18

<210> SEQ ID NO 358
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 358
gccccggccc cggcccc                                            17

<210> SEQ ID NO 359
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 359
ggccccggcc ccggccc                                            17

<210> SEQ ID NO 360
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 360
cggccccggc cccggcc                                            17

<210> SEQ ID NO 361
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 361
ccggccccgg ccccggc                                            17

<210> SEQ ID NO 362
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 362
cccggccccg gccccgg                                            17

<210> SEQ ID NO 363
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 363
ccccggcccc ggcccg                                             17

```
<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
ccccggcccc ggcccc                                                         16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
gccccggccc cggccc                                                         16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
ggccccggcc ccggcc                                                         16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
cggccccggc cccggc                                                         16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
ccggccccgg ccccgg                                                         16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
cccggccccg gccccg                                                         16
```